(12) United States Patent
Lipkens et al.

(10) Patent No.: US 9,745,548 B2
(45) Date of Patent: *Aug. 29, 2017

(54) ACOUSTIC PERFUSION DEVICES

(71) Applicant: FloDesign Sonics, Inc., Wilbraham, MA (US)

(72) Inventors: Bart Lipkens, Hampden, MA (US); Rudolf Gilmanshin, Framingham, MA (US); Louis Masi, Wilbraham, MA (US); Benjamin Ross-Johnsrud, Wilbraham, MA (US); Erik Miller, Belchertown, MA (US); Walter M. Presz, Jr., Wilbraham, MA (US); Thomas J. Kennedy, III, Wilbraham, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,073

(22) Filed: Jan. 30, 2017

(65) Prior Publication Data

US 2017/0137774 A1    May 18, 2017

Related U.S. Application Data

(63) Continuation-in-part of application No. 15/139,187, filed on Apr. 26, 2016, which is a continuation-in-part
(Continued)

(51) Int. Cl.
*B01D 37/00* (2006.01)
*C12M 1/00* (2006.01)
(Continued)

(52) U.S. Cl.
CPC ........... *C12M 47/02* (2013.01); *B01D 21/283* (2013.01); *C07K 1/14* (2013.01); *C12M 29/10* (2013.01);
(Continued)

(58) Field of Classification Search
CPC ...... B01D 29/115; B01D 37/00; B01D 29/52; B01D 29/865; B01D 2201/0415;
(Continued)

(56) References Cited

U.S. PATENT DOCUMENTS 2,473,971 A    6/1949   Ross
2,667,944 A    2/1954   Crites
(Continued)

FOREIGN PATENT DOCUMENTS

DE    30 27 433 A1    2/1982
DE    32 18 488 A1    11/1983
(Continued)

OTHER PUBLICATIONS

Alvarez et al.; Shock Waves, vol. 17, No. 6, pp. 441-447, 2008.
(Continued)

*Primary Examiner* — Walter D Griffin
*Assistant Examiner* — Cameron Allen
(74) *Attorney, Agent, or Firm* — Richard M. Klein; Fay Sharpe, LLP

(57) ABSTRACT

Methods are disclosed for separating beads and cells from a host fluid. The method includes flowing a mixture containing the host fluid, the beads, and the cells through an acoustophoretic device having an ultrasonic transducer including a piezoelectric material driven by a drive signal to create a multi-dimensional acoustic standing wave. A drive signal is sent to drive the at least one ultrasonic transducer to create the multi-dimensional acoustic standing wave. A recirculating fluid stream having a tangential flow path is located substantially tangential to the standing wave and separated therefrom by an interface region. A portion of the cells pass through the standing wave, and the beads are held back from the standing wave in the recirculating fluid stream at the interface region. Also disclosed is an acoustophoretic
(Continued)

device having a coolant inlet adapted to permit the ingress of a cooling fluid into the device for cooling the transducer.

23 Claims, 67 Drawing Sheets

Related U.S. Application Data of application No. 14/975,307, filed on Dec. 18, 2015, which is a continuation-in-part of application No. 14/175,766, filed on Feb. 7, 2014, now Pat. No. 9,416,344, which is a continuation-in-part of application No. 14/026,413, filed on Sep. 13, 2013, now Pat. No. 9,458,450, which is a continuation-in-part of application No. 13/844,754, filed on Mar. 15, 2013.

(60) Provisional application No. 62/307,934, filed on Mar. 14, 2016, provisional application No. 62/296,685, filed on Feb. 18, 2016, provisional application No. 62/288,500, filed on Jan. 29, 2016, provisional application No. 62/256,952, filed on Nov. 18, 2015, provisional application No. 62/243,211, filed on Oct. 19, 2015, provisional application No. 62/211,057, filed on Aug. 28, 2015, provisional application No. 62/093,491, filed on Dec. 18, 2014, provisional application No. 61/761,717, filed on Feb. 7, 2013, provisional application No. 61/708,641, filed on Oct. 2, 2012, provisional application No. 61/754,792, filed on Jan. 21, 2013, provisional application No. 61/708,641, filed on Oct. 2, 2012, provisional application No. 61/611,440, filed on Mar. 15, 2012, provisional application No. 61/611,159, filed on Mar. 15, 2012.

(51) Int. Cl.
  *B01D 21/28* (2006.01)
  *C12M 1/34* (2006.01)
  *G10K 15/04* (2006.01)
  *G10K 9/122* (2006.01)
  *C12M 1/26* (2006.01)
  *C12N 13/00* (2006.01)
  *C07K 1/14* (2006.01)

(52) U.S. Cl.
  CPC ............ *C12M 33/08* (2013.01); *C12M 41/12* (2013.01); *C12M 47/10* (2013.01); *C12N 13/00* (2013.01); *G10K 9/122* (2013.01); *G10K 15/043* (2013.01)

(58) Field of Classification Search
  CPC ..... B01D 2201/0446; B01D 2201/127; C12M 25/00; C12M 1/12
  See application file for complete search history.

(56) References Cited

U.S. PATENT DOCUMENTS

| | | | |
|---|---|---|---|
| 3,372,370 A | 3/1968 | Cyr | |
| 3,555,311 A | 1/1971 | Weber | |
| 4,055,491 A | 10/1977 | Porath-Furedi | |
| 4,065,875 A | 1/1978 | Srna | |
| 4,118,649 A | 10/1978 | Shwartzman et al. | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,254,661 A | 3/1981 | Kossoff et al. | |
| 4,320,659 A | 3/1982 | Lynnworth et al. | |
| 4,344,448 A | 8/1982 | Potts | |
| 4,398,325 A | 8/1983 | Piaget et al. | |
| 4,552,669 A | 11/1985 | Sekellick | |
| 4,666,595 A | 5/1987 | Graham | |
| 4,673,512 A | 6/1987 | Schram | |
| 4,699,588 A | 10/1987 | Zinn et al. | |
| 4,743,361 A | 5/1988 | Schram | |
| 4,759,775 A | 7/1988 | Peterson et al. | |
| 4,800,316 A | 1/1989 | Ju-Zhen | |
| 4,821,838 A | 4/1989 | Chen | |
| 4,836,684 A | 6/1989 | Javorik et al. | |
| 4,860,993 A | 8/1989 | Goode | |
| 4,878,210 A | 10/1989 | Mitome | |
| 4,983,189 A | 1/1991 | Peterson et al. | |
| 5,059,811 A | 10/1991 | King et al. | |
| 5,062,965 A | 11/1991 | Bernou et al. | |
| 5,085,783 A | 2/1992 | Feke et al. | |
| 5,164,094 A | 11/1992 | Stuckart | |
| 5,225,089 A | 7/1993 | Benes et al. | |
| 5,371,429 A | 12/1994 | Manna | |
| 5,395,592 A | 3/1995 | Bolleman et al. | |
| 5,431,817 A | 7/1995 | Braatz et al. | |
| 5,443,985 A | 8/1995 | Lu et al. | |
| 5,452,267 A | 9/1995 | Spevak | |
| 5,475,486 A | 12/1995 | Paoli | |
| 5,484,537 A | 1/1996 | Whitworth | |
| 5,527,460 A | 6/1996 | Trampler et al. | |
| 5,560,362 A | 10/1996 | Sliwa, Jr. et al. | |
| 5,594,165 A | 1/1997 | Madanshetty | |
| 5,604,301 A | 2/1997 | Mountford et al. | |
| 5,626,767 A | 5/1997 | Trampler et al. | |
| 5,688,405 A | 11/1997 | Dickinson et al. | |
| 5,711,888 A | 1/1998 | Trampler et al. | |
| 5,831,166 A | 11/1998 | Kozuka et al. | |
| 5,834,871 A | 11/1998 | Puskas | |
| 5,902,489 A | 5/1999 | Yasuda et al. | |
| 5,912,182 A | 6/1999 | Coakley et al. | |
| 5,947,299 A | 9/1999 | Vazquez et al. | |
| 5,951,456 A | 9/1999 | Scott | |
| 6,090,295 A | 7/2000 | Raghavarao et al. | |
| 6,166,231 A | 12/2000 | Hoeksema | |
| 6,205,848 B1 | 3/2001 | Faber et al. | |
| 6,216,538 B1 | 4/2001 | Yasuda et al. | |
| 6,273,262 B1 | 8/2001 | Yasuda et al. | |
| 6,332,541 B1 | 12/2001 | Coakley et al. | |
| 6,391,653 B1 | 5/2002 | Letcher et al. | |
| 6,475,151 B2 | 11/2002 | Koger et al. | |
| 6,482,327 B1 | 11/2002 | Mori et al. | |
| 6,487,095 B1 | 11/2002 | Malik et al. | |
| 6,592,821 B1 | 7/2003 | Wada et al. | |
| 6,641,708 B1 | 11/2003 | Becker et al. | |
| 6,649,069 B2 | 11/2003 | DeAngelis | |
| 6,699,711 B1 | 3/2004 | Hahn et al. | |
| 6,727,451 B1 | 4/2004 | Fuhr et al. | |
| 6,763,722 B2 | 7/2004 | Fjield et al. | |
| 6,881,314 B1 | 4/2005 | Wang et al. | |
| 6,929,750 B2 | 8/2005 | Laurell et al. | |
| 6,936,151 B1 | 8/2005 | Lock et al. | |
| 7,008,540 B1 | 3/2006 | Weavers et al. | |
| 7,010,979 B2 | 3/2006 | Scott | |
| 7,061,163 B2 | 6/2006 | Nagahara et al. | |
| 7,081,192 B1 | 7/2006 | Wang et al. | |
| 7,093,482 B2 | 8/2006 | Berndt | |
| 7,108,137 B2 | 9/2006 | Lal et al. | |
| 7,150,779 B2 | 12/2006 | Meegan, Jr. | |
| 7,186,502 B2 | 3/2007 | Vesey | |
| 7,191,787 B1 | 3/2007 | Redeker et al. | |
| 7,322,431 B2 | 1/2008 | Ratcliff | |
| 7,331,233 B2 | 2/2008 | Scott | |
| 7,340,957 B2 | 3/2008 | Kaduchak et al. | |
| 7,373,805 B2 | 5/2008 | Hawkes et al. | |
| 7,541,166 B2 | 6/2009 | Belgrader et al. | |
| 7,601,267 B2 | 10/2009 | Haake et al. | |
| 7,673,516 B2 | 3/2010 | Janssen et al. | |
| 7,837,040 B2 | 11/2010 | Ward et al. | |
| 7,846,382 B2 | 12/2010 | Strand et al. | |
| 7,968,049 B2 | 6/2011 | Takahashi et al. | |
| 8,075,786 B2 | 12/2011 | Bagajewicz | |
| 8,080,202 B2 | 12/2011 | Takahashi et al. | |
| 8,134,705 B2 | 3/2012 | Kaduchak et al. | |

(56) References Cited

U.S. PATENT DOCUMENTS

| | | |
|---|---|---|
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 * | 11/2013 | Lipkens ............... C12N 13/00 435/173.7 |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181828 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn, et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Wienand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Rietman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0321129 A1 | 11/2015 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 * | 8/2016 | Lipkens ............... B01D 17/04 |
| 2016/0237395 A1 * | 8/2016 | Lipkens ............... C12M 47/02 |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |

(56) References Cited

U.S. PATENT DOCUMENTS

| | | | |
|---|---|---|---|
| 2016/0314868 A1 | 10/2016 | El-Zahab et al. |
| 2016/0319270 A1 | 11/2016 | Lipkens et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 87/07178 A1 | 12/1987 |
| WO | WO 89/11899 A1 | 12/1989 |
| WO | WO 90/05008 | 3/1990 |
| WO | WO 97/34643 | 9/1997 |
| WO | WO 98/17373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

Annex to Form PCT/ISA/206—Communication Relating to the Results of the Partial International Search Report, dated Jul. 18, 2013.

European Search Report of European Application No. 11769474.5, dated Sep. 5, 2013.

European Search Report of European Application No. 13760840.2, dated Feb. 4, 2016.

European Search Report of European Application No. 13721179.3 dated Feb. 23, 2016.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2012/051804 dated Nov. 16, 2012.

(56) References Cited

OTHER PUBLICATIONS

International Search Report and Written Opinion of International Application No. PCT/US2013/037404 Dated Jun. 21, 2013.
International Search Report and Written Opinion of International Application No. PCT/US2013/032705 dated Jul. 26, 2013.
International Search Report and Written Opinion of International Application No. PCT/US2013/050729 Dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report mailed Jul. 30, 2015 for International Application No. PCT/US2015/030009.
International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
phys. org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

\* cited by examiner

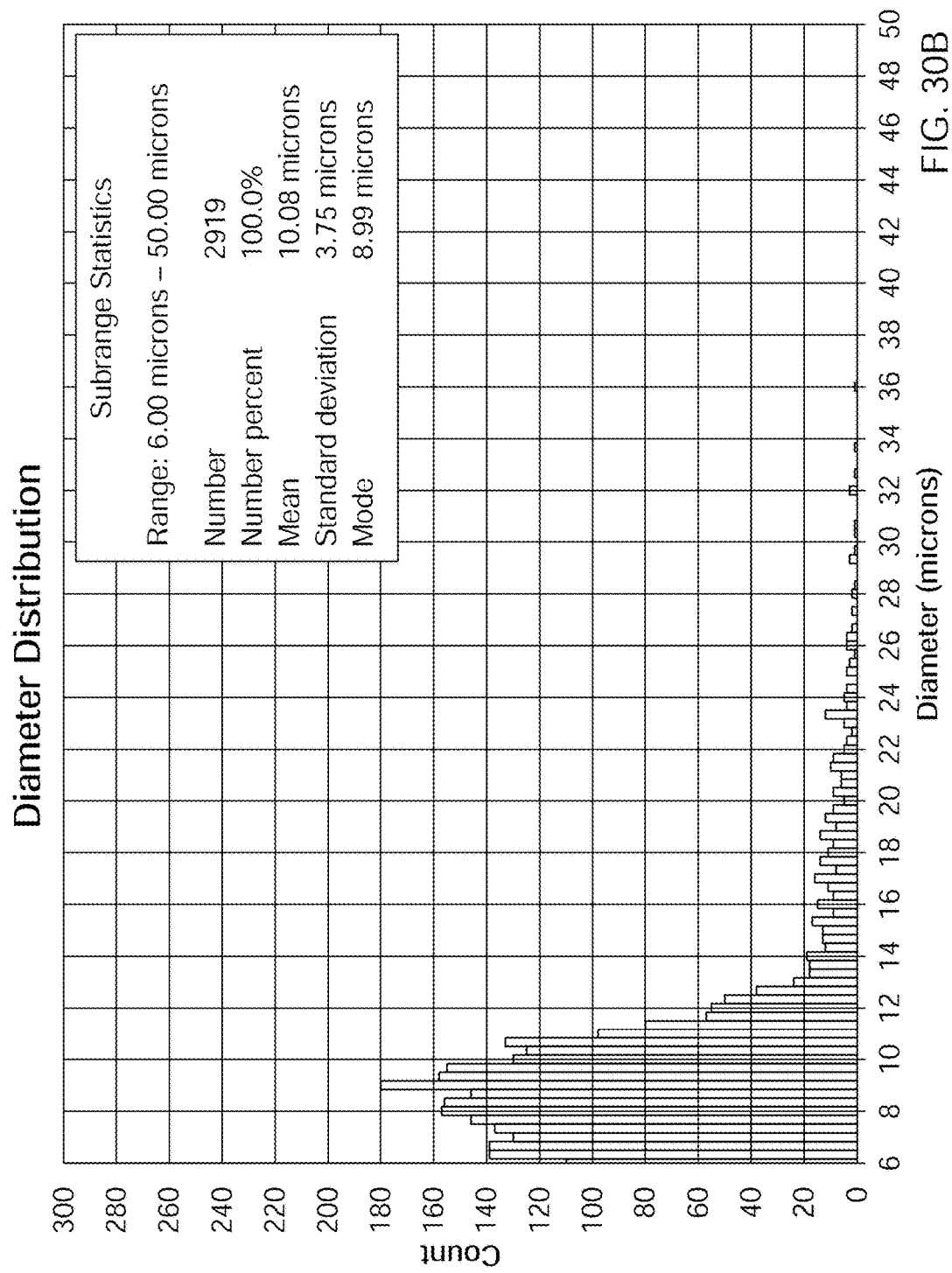

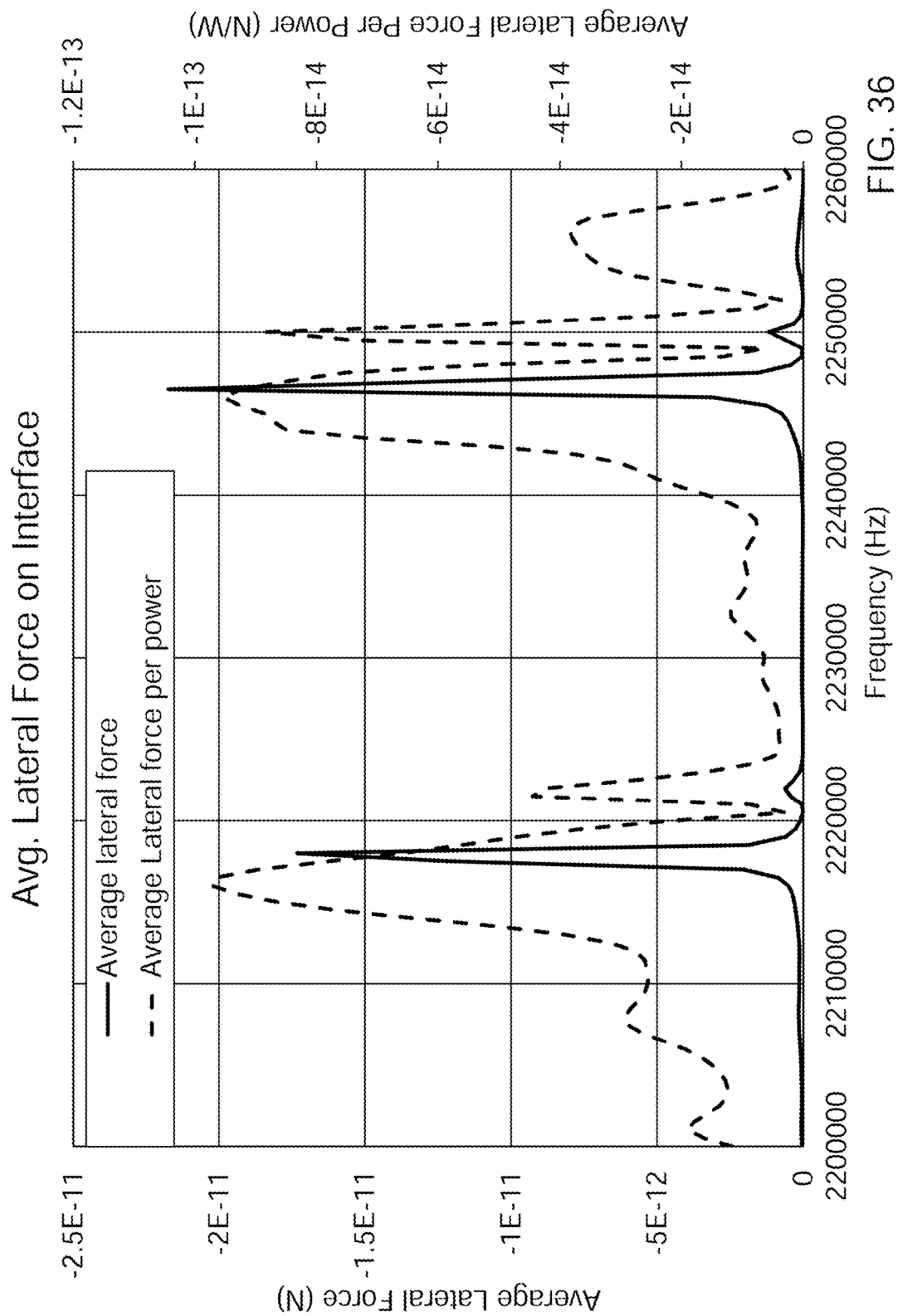

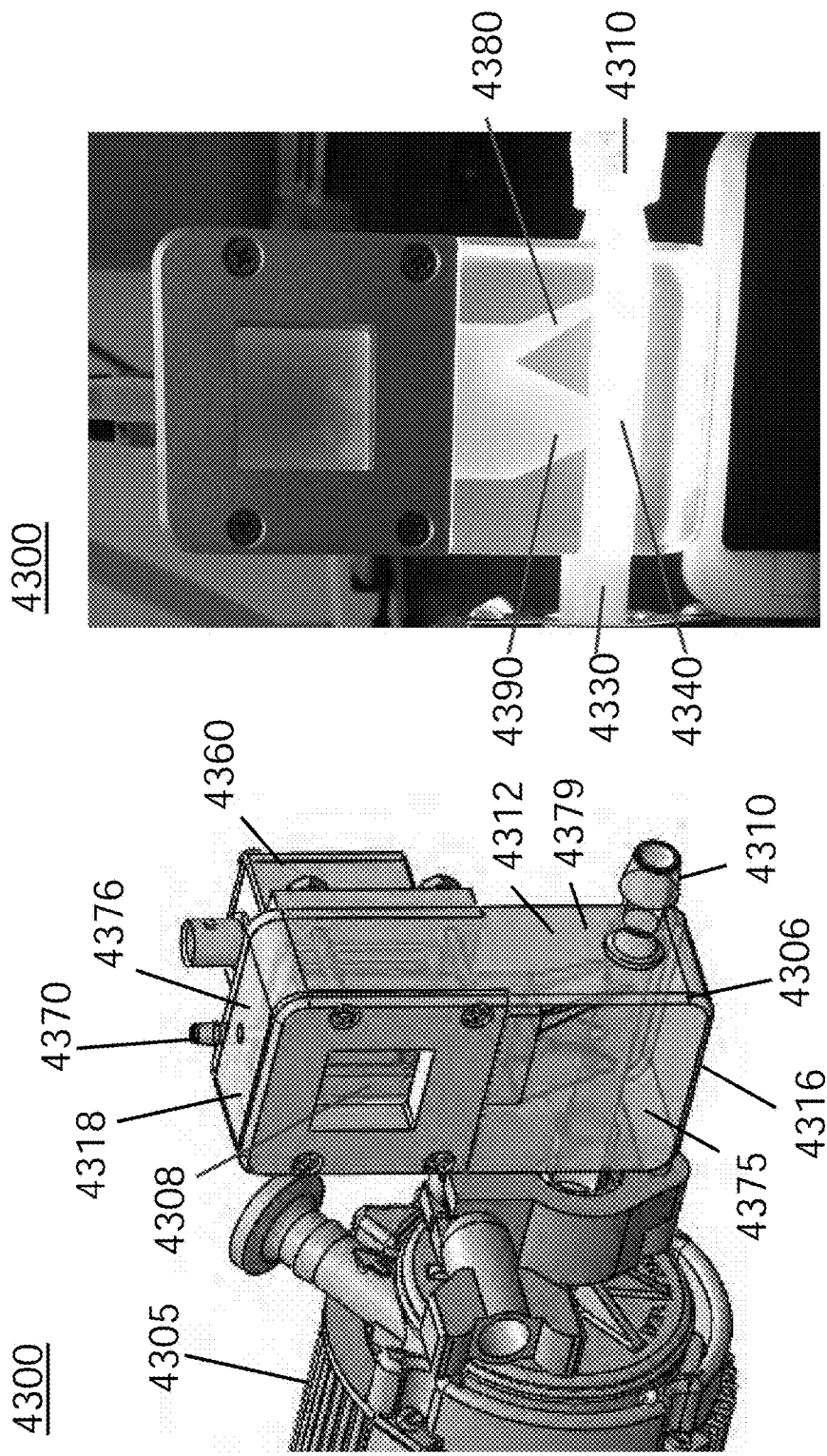

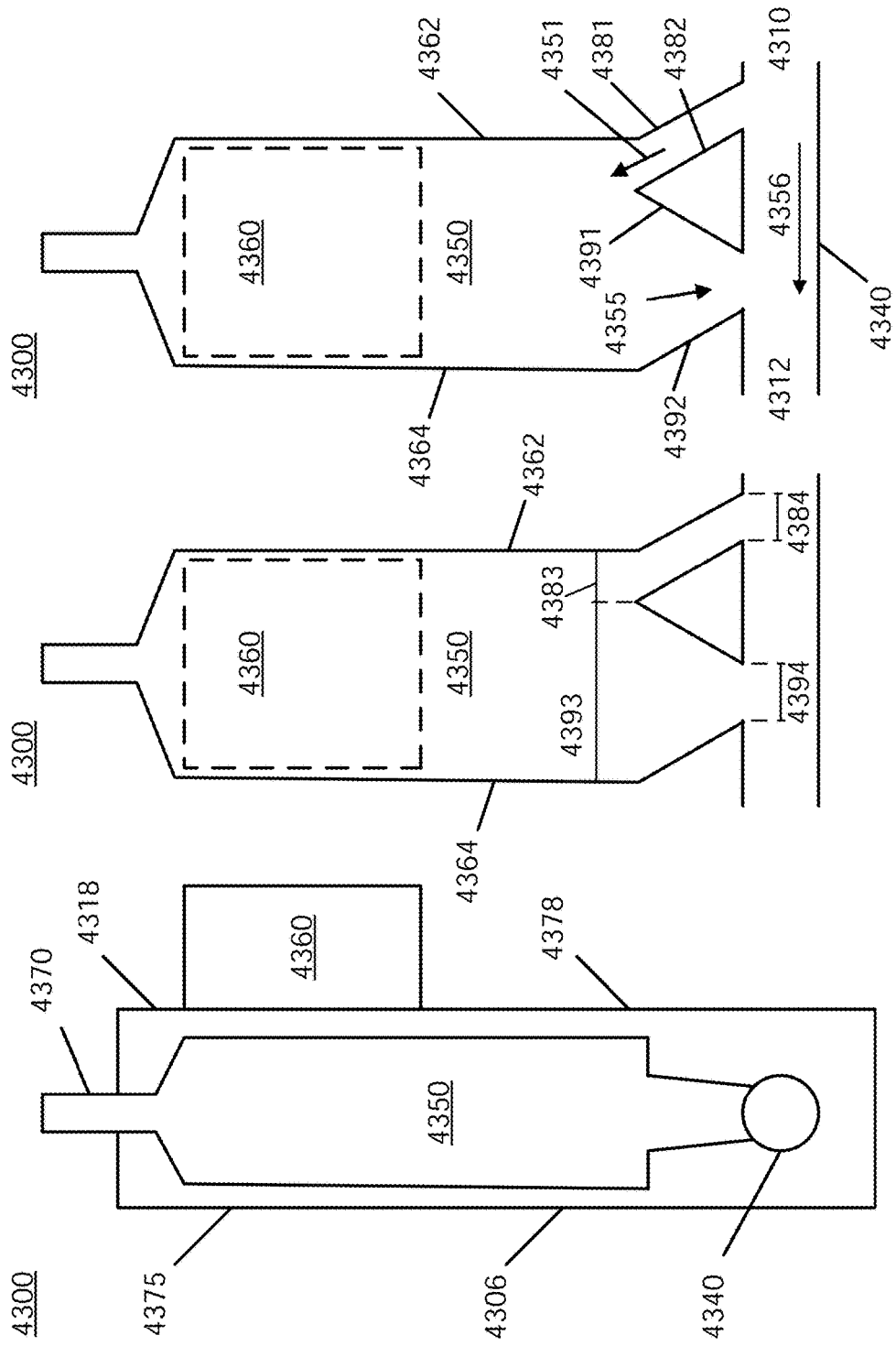

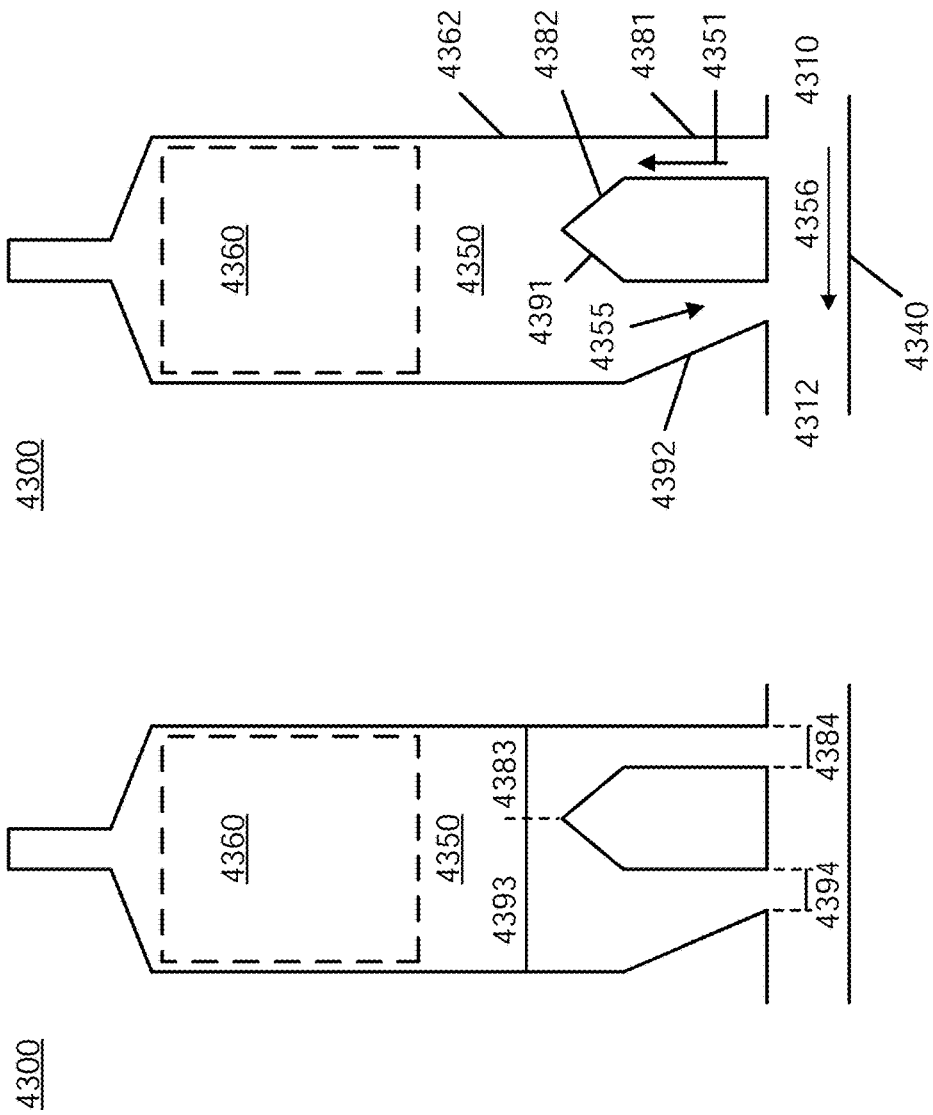

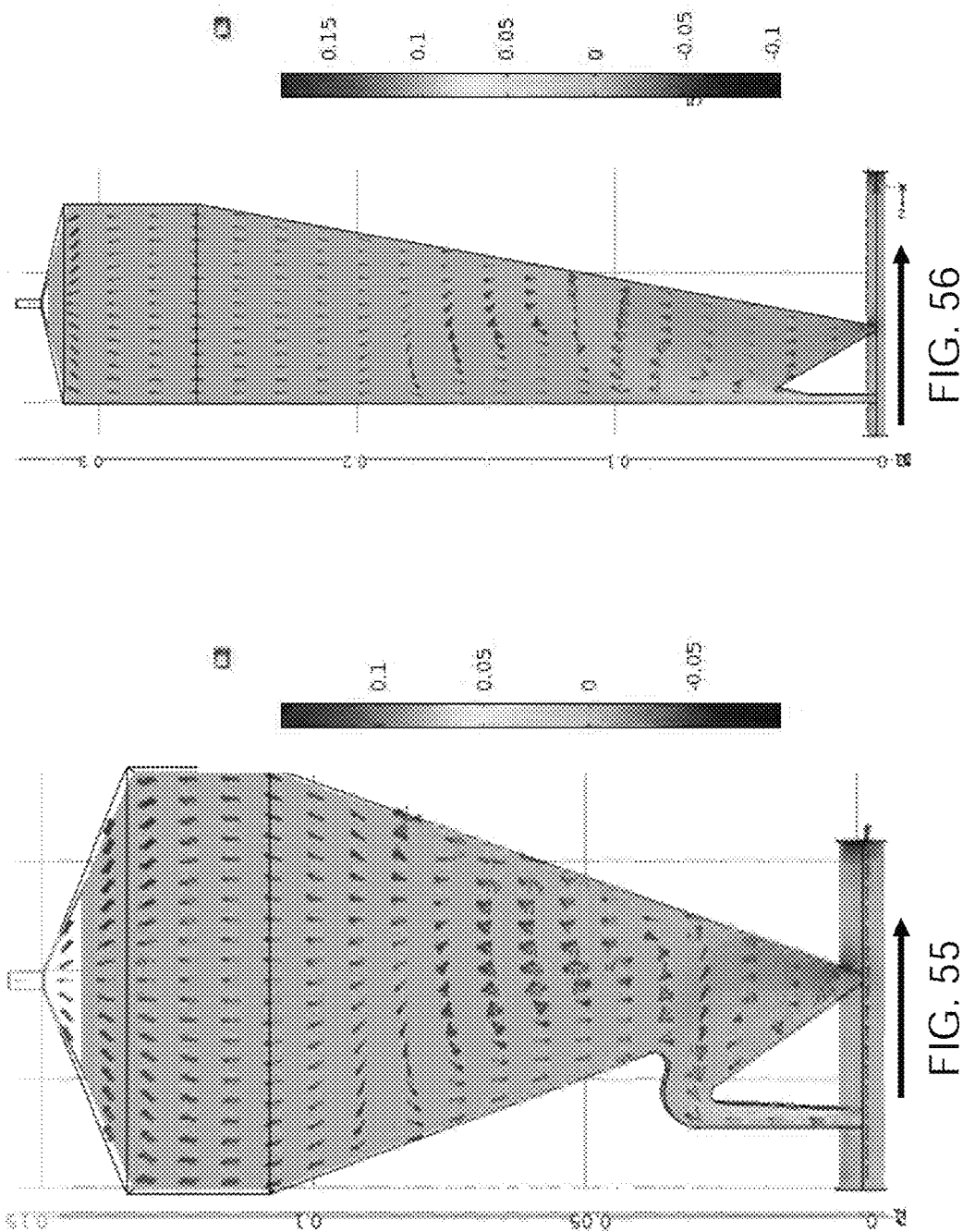

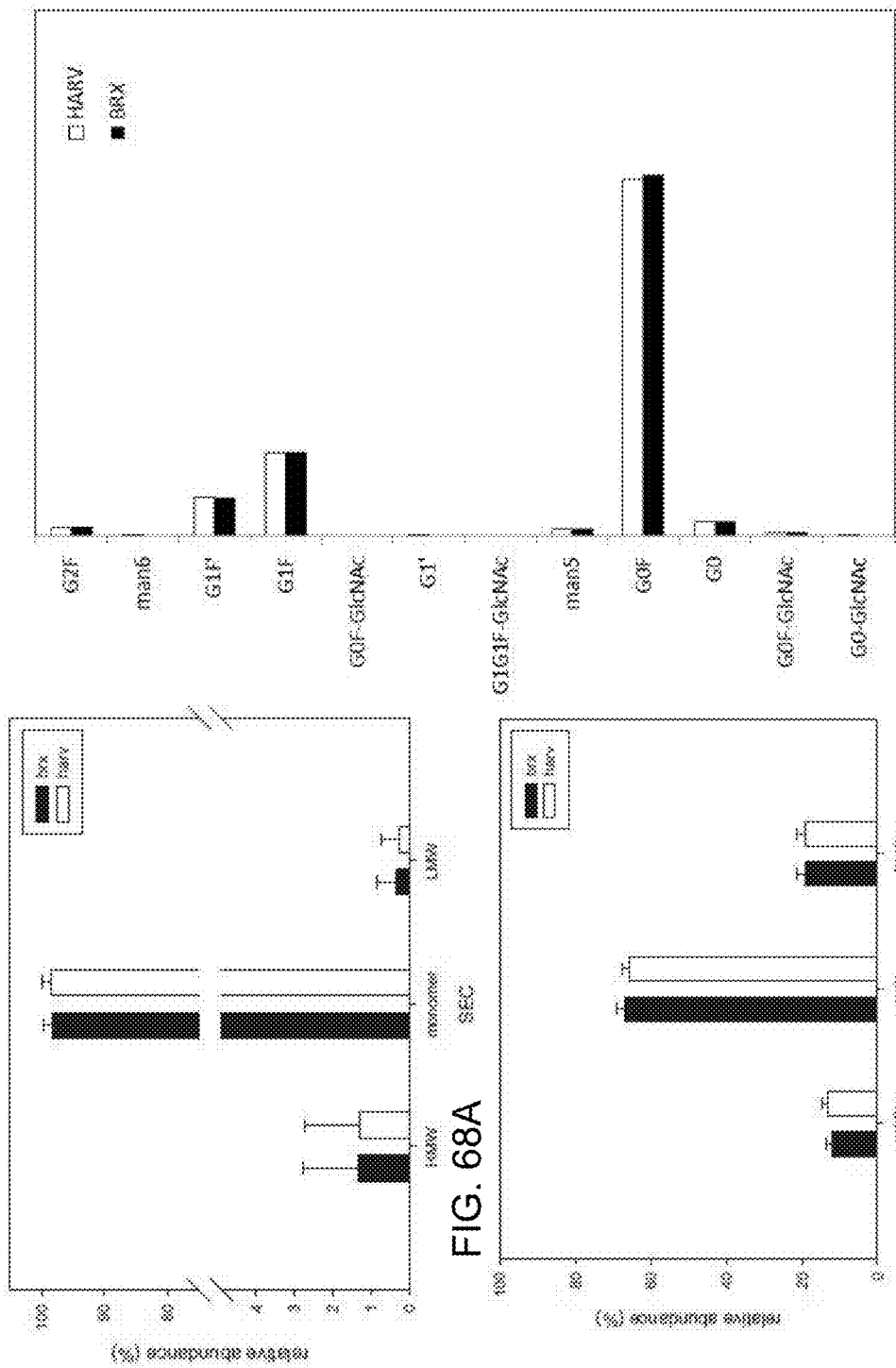

ACOUSTIC PERFUSION DEVICES

CROSS-REFERENCE TO RELATED APPLICATIONS

This application claims priority to U.S. Provisional Patent Application Ser. No. 62/288,500, filed Jan. 29, 2016, and to U.S. Provisional Patent Application Ser. No. 62/296,685, filed Feb. 18, 2016, and to U.S. Provisional Patent Application Ser. No. 62/307,934, filed Mar. 14, 2016. This application is also a continuation-in-part of U.S. patent application Ser. No. 15/139,187, filed Apr. 26, 2016, which is a continuation-in-part of U.S. patent application Ser. No. 14/975,307, filed Dec. 18, 2015, which claims priority to U.S. Provisional Patent Application Ser. No. 62/256,952, filed on Nov. 18, 2015, and to U.S. Provisional Patent Application Ser. No. 62/243,211, filed on Oct. 19, 2015, and to U.S. Provisional Patent Application Ser. No. 62/211,057, filed on Aug. 28, 2015, and to U.S. Provisional Patent Application Ser. No. 62/093,491, filed on Dec. 18, 2014. U.S. patent application Ser. No. 14/975,307 is also a continuation-in-part of U.S. patent application Ser. No. 14/175,766, filed on Feb. 7, 2014, which claims priority to U.S. Provisional Patent Application Ser. No. 61/761,717, filed on Feb. 7, 2013, and is also a continuation-in-part of U.S. patent application Ser. No. 14/026,413, filed on Sep. 13, 2013, which claims the benefit of U.S. Provisional Patent Application Ser. No. 61/708,641, filed on Oct. 2, 2012. U.S. patent application Ser. No. 14/026,413 is also a continuation-in-part of U.S. Ser. No. 13/844,754, filed Mar. 15, 2013, which claims the benefit of U.S. Provisional Patent Application Ser. No. 61/611,159, filed Mar. 15, 2012, and of U.S. Provisional Patent Application Ser. No. 61/611,440, filed Mar. 15, 2012, and of U.S. Provisional Patent Application Ser. No. 61/754,792, filed Jan. 21, 2013, and of U.S. Provisional Patent Application Ser. No. 61/708,641, filed on Oct. 2, 2012. These applications are incorporated herein by reference in their entireties.

STATEMENT REGARDING FEDERALLY SPONSORED RESEARCH

This invention was made with government support under Grant No. IIP-1330287 (Amendment 003, Proposal No. 1458190) awarded by the National Science Foundation. The government has certain rights in the invention.

BACKGROUND

The field of biotechnology has grown tremendously in the last 20 years. This growth has been due to many factors, some of which include the improvements in the equipment available for bioreactors, the increased understanding of biological systems and increased knowledge as to the interactions of materials (such as monoclonal antibodies and recombinant proteins) with the various systems of the human body.

A perfusion bioreactor processes a continuous supply of fresh media that is fed into the bioreactor while growth-inhibiting byproducts are constantly removed. The nonproductive downtime can be reduced or eliminated with a perfusion bioreactor process. The cell densities achieved in perfusion culture (30-100 million cells/mL) are typically higher than for fed-batch modes (5-25 million cells/mL). These improvements have led to lower contamination in the harvest and better yields without significant increase in cost. A perfusion bioreactor may use a cell retention device to prevent escape of the culture when byproducts are being removed. These cell retention systems may add a level of complexity to the perfusion process, where further management, control, and/or maintenance operations may be implemented. Operational issues such as malfunction or failure of the cell retention equipment has previously been a problem with perfusion bioreactors, which has limited their attractiveness in the past.

In the biotechnology and biopharma fields, it is desirable to separate many different types of materials from a primary fluid stream based on size, surface active materials, density, and other characteristics. Tangential flow filtration has been widely adopted to separate and concentrate diverse array of microbes and other materials from a fluid stream. These materials have been filtered utilizing different physical polymer membranes such as polyvinylidene difluoride (PDF) and polyether sulfone (PES).

Issues that arise with tangential flow filtration include the cost of the membrane materials, the formation of a gel layer or filtrate-suppressing layer on the filter membranes, the consistency of the polymer membranes, and the entire efficiency of the process. There is also the possibility of product loss due to clogging of the polymer membranes and the need to replace these clogged membranes.

There is therefore a need to improve the continuous processing of materials throughout the tangential flow process, decrease the cost, increase the efficiency, and improve the overall ability of the separation process to perform primary, secondary, tertiary and beyond separation of materials from a primary fluid stream.

BRIEF DESCRIPTION

The present disclosure relates, in various embodiments, to acoustic devices which are used for perfusion biomanufacturing. More particularly, the devices are coupled to an associated bioreactor. Within the bioreactor, biomolecules, such as recombinant proteins or monoclonal antibodies, and other materials are produced. Materials may include viruses, virus-like particles, exosomes, oncozomes, materials from cell free protein synthesis, cell vesicles, proteins, monoclonal antibodies, recombinant proteins and other materials. The acoustic device is used for separating desirable products from the bioreactor contents on a continuous basis, and the cells or other materials are continuously returned to the bioreactor for further culturing. Generally, a fluid mixture containing the cells and the desired products are passed or flowed through the acoustic device and separated therein by multi-dimensional standing wave(s). The fluid mixture generally also contains other materials, such as cell debris and fines. The fluid mixture can be continuously flowed into the device, with desired products being continuously removed. The acoustic perfusion device returns healthy viable cells to the bioreactor while desired products are harvested and flowed downstream for further processing, e.g., additional filtering, chromatography, etc. Additionally, the cell culture media in the bioreactor is clarified as cell fragments are also allowed to pass into the harvest stream and thereby out of the fluid mixture being recycled to the bioreactor. This arrangement results in lower overall cell culture media usage, corresponding to a predicted cost savings of up to $20,000 per day for large bioreactors.

Disclosed in various embodiments are acoustic perfusion devices, comprising: an acoustic chamber; an inlet port, an inlet flow path leading from the inlet port to the acoustic chamber; an outlet port for recirculating fluid flowing through the device back to its source (e.g. a bioreactor), and an outlet flow path leading from the acoustic chamber to the outlet port; at least one collection or harvest port for collecting a product stream of fluid exiting the acoustic chamber; and at least one ultrasonic transducer in the acoustic chamber below the at least one harvest port, the at least one ultrasonic transducer including a piezoelectric material driven by a drive signal to create an acoustic standing wave across a collection or harvest flow path leading from the acoustic chamber to the at least one collection or harvest port. The acoustic standing wave may be planar or multi-dimensional, or a combination of such waves may be present within the acoustic chamber (generally from multiple transducers). The acoustic standing wave can be thought of as a "force field" that holds back whole cells but permits smaller materials such as the desired biomolecules (e.g. recombinant proteins and/or monoclonal antibodies) and cell fragments, to pass through and be removed from the fluid that is returned to the bioreactor.

The outlet port is generally below the inlet port, and is generally located at a bottom end of the device.

As mentioned above, the device may have one or more collection or harvest ports at the top of the device. In some more specific embodiments, the device may have a total of two harvest ports spaced apart from each other on the top end of the device.

In particular embodiments, the inlet port is at a first end of the device at a first height, the at least one ultrasonic transducer is at a second height above the first height, and a bottom wall extends from the inlet port to the outlet port. The outlet port may be located at a second end of the device opposite the first end. The bottom wall may be concave, relative to a line between the inlet port and the outlet port. The device may include an upper wall above the inlet flow path. The inlet port, the outlet port, and the at least one harvest port are sometimes all located on a front wall of the device. The front wall itself may be planar (i.e. flat).

The device can further comprise a reflector located in the acoustic chamber opposite the at least one ultrasonic transducer. Alternatively, the device can have a total of two ultrasonic transducers located on opposite sides of the harvest flow path at the same height and facing each other, or additional ultrasonic transducers can be located on multiple sides of the collection/harvest flow path. A reflector may be located between the two ultrasonic transducers. There may also be a plurality of transducer/reflector pairs located as appropriate to form planar, multi-dimensional, or combinations of such acoustic standing wave(s).

In particular embodiments, the acoustic standing wave results in an acoustic radiation force having an axial force component and a lateral force component that are of the same order of magnitude.

In other embodiments of the device disclosed herein, the inlet flow path leads from the inlet port downwards towards a bottom end of the device and past the outlet port, and then upwards to the acoustic chamber. Sometimes, the inlet port and the at least one harvest port are both located on a top wall of the device, and the outlet port is located on a front wall of the device. The at least one ultrasonic transducer may be mounted in a rear wall or a front wall of the device. The bottom wall of this acoustic chamber can be a sloped planar surface. The reflector may be made of a transparent material.

The inlet flow path may be shaped to generate a tangential flow path below an acoustic field generated by the acoustic standing wave. In still additional versions seen herein, the inlet flow path enters the acoustic chamber on a first side of the device, and the outlet port is located (i) on the first side of the device or (ii) on a second opposite side. The inlet port can be located on a front side of the device, and the at least one harvest port can be located on a top wall of the device. The at least one transducer can be located on a front side or a rear side of the device. In more particular embodiments, there can be two transducers, one on the front side and one of the rear side. In yet other particular embodiments, there is an ultrasonic transducer on the front or rear side, and a reflector located on the respective rear or front side opposite the transducer.

In additional embodiments, the perfusion device further comprises a recirculation flow path between the inlet port and the outlet port that does not enter the acoustic chamber, and the recirculation flow path is located below the acoustic chamber. In some particular embodiments, the inlet flow path travels through a different passage than the outlet flow path. In yet other embodiments, the inlet flow path and the outlet flow path travel through a common passage.

The device may be attached to a mounting piece having holes for attachment.

Also disclosed are methods for separating cells from a fluid mixture containing the cells. The fluid mixture is flowed through an acoustic perfusion device of the structure described above, having at least one ultrasonic transducer. The at least one ultrasonic transducer is driven to create the acoustic standing wave. A fluid enriched in cells can be collected from the outlet port and a clarified fluid, depleted in cells, can be collected from the at least one harvest port.

In particular embodiments, the flow rate through the collection/harvest flow path is at least one order of magnitude smaller than a flow rate through the inlet flow path. In specific embodiments, a flow rate of the fluid mixture entering the device through the inlet port is about 1 liter per minute and a flow rate of the fluid depleted in cells exiting the device through the at least one collection/harvest port is about 10 milliliters per minute. Alternatively, the ratio of the flow rate entering through the inlet port to the flow rate exiting through the at least one collection/harvest port is such that the acoustic standing wave is not overcome by the main body of cells, or in other words so that a large volume of cells do not begin exiting the device through the collection/harvest port(s).

The methods may further comprise pulling the fluid mixture through the device using a first pump attached to the at least one harvest port of the device and a second pump attached to the outlet port of the device.

Also disclosed herein are flow devices adapted to (i) receive a flowing mixture containing a primary fluid and cells; and (ii) to use a first acoustic standing wave to continuously draw off a harvest fluid stream depleted in cells from the flowing mixture, thereby changing the cell concentration of the flowing mixture. A pressure rise may be generated on the upstream interface region of the acoustic standing wave, along with an acoustic radiation force acting on the incoming suspended particles. This "interface effect", which may also be termed "edge effect", acts as a barrier and is typically located at the upstream bounding surface of the volume of fluid that is ensonified by the transducer (i.e. the flow mixture crosses the interface region to enter the ensonified volume of fluid). The frequency of the acoustic standing wave may be modified such that different contrast factor materials may be held back or allowed through the acoustic standing wave, or such that particles of one given size range are retained and particles of a second given range are allowed to flow through the standing wave.

The device may further comprise a secondary flow chamber in which the harvest fluid stream depleted in cells passes through a second acoustic standing wave having a frequency different from, or equal to the first acoustic standing wave. For example, the second acoustic standing wave may have a higher or lower frequency than the first acoustic standing wave. The ratio of the frequency of the two standing waves is, in some embodiments, at least 2:1 (i.e. one of the frequencies is at least twice the other frequency, e.g. 3 MHz and 6 MHz).

Also disclosed herein are flow devices that comprise: at least one inlet for receiving a flowing mixture of a primary fluid and cells, an ultrasonic transducer that produces a first ultrasonic acoustic standing wave and uses a pressure rise and an acoustic radiation force generated on an upstream interface region of the first ultrasonic acoustic standing wave to separate the flowing mixture into a primary high cell concentration fluid stream and a secondary harvest fluid stream; an outlet port for the primary high cell concentration fluid stream; and at least one collection port for the secondary harvest fluid stream. A bleed port can also be present for extracting a concentrated fluid/cell mixture. The fluid mixture may comprise particles such as mammalian cells, bacteria, cell debris, fines, proteins, exosomes, vesicles, viruses, and insect cells.

The device may further comprise a secondary flow chamber in which the secondary harvest fluid stream passes through a second acoustic standing wave having a frequency different from, or equal to, the first ultrasonic acoustic standing wave.

Also disclosed herein are methods for separating microspheres, microbeads, nano beads, microcarriers and other micro and nano particulates (collectively known as beads), and cells from a host fluid. The methods comprise flowing a mixture containing a host fluid, the beads, and the cells through an acoustophoretic device; sending a voltage signal to drive an ultrasonic transducer to create the multi-dimensional acoustic standing wave, wherein a recirculating fluid stream having a tangential flow path is located substantially tangential to the multi-dimensional acoustic standing wave and separated therefrom by an interface region; and wherein at least a portion of the cells (e.g., at least 95% of the cells, including up to about 99% of the cells) pass through the multi-dimensional acoustic standing wave, and the beads are held back from the multi-dimensional acoustic standing wave in the recirculating fluid stream at the interface region. The acoustophoretic device may be constructed as described herein, namely comprising a flow chamber having at least one inlet and at least one outlet; at least one ultrasonic transducer located in the flow chamber, the at least one ultrasonic transducer including a piezoelectric material driven by a voltage signal to create a multi-dimensional acoustic standing wave in the flow chamber; and a reflector located in the flow chamber opposite from the at least one ultrasonic transducer.

In particular embodiments, the beads are non-functionalized. Other embodiments include functionalizing the beads such that the beads attach to the cells. The beads can be functionalized with various materials, such as antigens, on the surface that will allow for affinity binding of materials (e.g., viruses, virus-like particles, exosomes, oncozomes, materials from cell free will protein synthesis, proteins, monoclonal antibodies, recombinant proteins) to the beads. The functionalized beads may, in some embodiments, have a positive contrast factor. The functionalized beads having a positive contrast factor may be selected from the group consisting of polystyrene beads and glass beads. In other embodiments, have a negative contrast factor. The functionalized beads having a negative contrast factor may be selected from the group consisting of microbubbles and micro-glass spheres. The beads may, in certain embodiments, be polymeric, glass, hollow, or gas-filled. The beads can be spherical, toroidal, cylindrical, or conical.

In certain embodiments of the method, the mixture can include microvesicles (e.g., exosomes, oncosomes, viruses, proteins, recombinant proteins, and monoclonal antibodies). A pressure rise and an acoustic radiation force on cells can be generated at the interface region to clarify the host fluid as it passes through the multi-dimensional acoustic standing wave. In particular embodiments, the method further comprises collecting the cells after passing through the multi-dimensional acoustic standing wave for a first time and recirculating the collected cells are back through the device for separation by the multi-dimensional acoustic standing wave for a second time. The method can further comprise collecting the cells after passing through the multi-dimensional acoustic standing wave for the second time.

Also disclosed herein are acoustophoretic devices including a flow chamber having at least one inlet port and at least one outlet; at least one ultrasonic transducer coupled to the flow chamber and at least one reflector coupled to the flow chamber opposite the at least one ultrasonic transducer, wherein the at least one ultrasonic transducer includes a piezoelectric material driven by a voltage signal to create a multi-dimensional acoustic standing wave in the device; and a coolant inlet adapted to permit the ingress of an associated cooling fluid into the device for cooling the at least one ultrasonic transducer.

In certain constructions, the at least one inlet port includes a first inlet port on a front wall of the device, a second inlet port on a rear wall of the device opposite the front wall thereof, and the at least one outlet includes a permeate outlet on the first sidewall of the device, a wastewater outlet on the first sidewall of the device, and a drain outlet on a first sidewall of the device.

The cooling fluid can be the same or different from the primary fluid that flows through the flow chamber carrying particles (e.g., cells and beads). For example, the cooling fluid can be water, air, alcohol, ethanol, ammonia, or some combination thereof. The cooling fluid can, in certain embodiments, be a liquid, gas, or gel. The cooling fluid can be an electrically non-conductive fluid to prevent electric short-circuits.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

In FIG. 29B, the y-axis is the particle count from 0 to 200 in intervals of 10. The x-axis is the particle diameter in microns from 6 to 50 in intervals of 2. The total number of particles is 5539, the mean particle size is 16.78 microns, standard deviation of 6.76 microns, and mode particle size of 10.56 microns.

FIG. 30B is a graph of the particle diameter distribution of the perfusate, showing a unimodal distribution at much lower sizes. In FIG. 30B, the y-axis is the particle count from 0 to 300 in intervals of 20. The x-axis is the particle diameter in microns from 6 to 50 in intervals of 2. The total number of particles is 2919, the mean particle size is 10.08 microns, standard deviation of 3.75 microns, and mode particle size of 8.99 microns.

FIG. 35A is at a frequency of 2.218 MHz. FIG. 35B is at a frequency of 2.2465 MHz. FIG. 35C is at a frequency of 2.3055 MHz. For all three graphs, the left-side scale is indicated with text at the top of the scale reading "×10$^{-6}$" or "×10$^{-7}$", and is in units of inches. The right-side scale is indicated with text at the top of the scale reading "×10$^6$", and is in units of Pascals. The y-axis runs from −0.8 to 1.6 in intervals of 0.2. The x-axis runs from −0.5 to 1.5 in intervals of 0.5.

FIG. 36 is a graph showing the average lateral force (N) and the average lateral force normalized by power (N/W) acting on suspended CHO cells at several frequencies of operation.

FIG. 43 is a perspective view of a fifth exemplary embodiment of an acoustic perfusion device of the present disclosure. This embodiment includes a direct recirculation flow path between the inlet port and the outlet port. An inflow passageway and an outflow passageway join the recirculation flow path to the acoustic chamber, and create a tangential sweeping flow underneath the acoustic field.

FIG. 44 is a front view picture of the device of FIG. 43. The inflow passageway and the outflow passageway are clearly visible, along with the recirculation pipe.

FIG. 45 is a diagrammatic side view of the device of FIG. 43.

FIG. 46A and FIG. 46B are a diagrammatic front view of the device of FIG. 43, showing one internal structure. The figures are duplicated due to the number of reference numerals.

FIG. 46C and FIG. 46D are a diagrammatic front view of the device of FIG. 43, showing an alternative internal structure, where the inflow passageway and the outflow passageway have a different flow geometry. The figures are duplicated due to the number of reference numerals.

FIG. 55 is a CFD model showing the velocity distribution for another internal structure for the device of FIG. 43. The scale runs from −0.05 to 0.1 m/s in intervals of 0.05.

FIG. 56 is a CFD model showing the velocity distribution for another internal structure for the device of FIG. 43. The scale runs from −0.1 to 0.15 m/s in intervals of 0.05.

FIG. 66A shows the mAb titer on the y-axis versus the culture day on the x-axis. The production of the mAb titer is higher for the AWS than it is for the TFF where the cells are bled away. FIG. 66B is a graph comparing the transmission of monoclonal antibody (mAb) versus culture day. The y-axis is % transmission, and the x-axis is the culture day. The dotted line indicates 100% transmission. Higher % transmission is better. The mAb transmission is higher for the AWS versus the TFF with or without cell bleed. FIG. 66C shows relative mAb residence time on the y-axis versus culture day on the x-axis. The relative residence time for the mAb separated by AWS is lower than the relative residence time for the TFF with or without cell bleed.

FIG. 68A is a graph showing the relative abundance of high molecular weight (HMW) species, monomer species, and low molecular weight (LMW) species of a monoclonal antibody (mAb) after size exclusion chromatography (SEC). The darker bars represent the bioreactor, and the lighter bars represent the harvest. FIG. 68B is a graph showing the relative abundance of acidic, main peak, and basic species of a mAb after ion exchange chromatography (IEX). Again, the darker bars represent the bioreactor, and the lighter bars represent the harvest. FIG. 68C is a bar graph showing glycosylation of proteins, showing the proteins sent through the acoustic perfusion device do not differ from proteins sent through a TFF device. BRX refers to the bioreactor, and HARV indicates the harvested material.

FIG. 69A shows the relative abundance of HMW species, monomer species, and LMW species of a mAb after size exclusion chromatography (SEC). FIG. 69B shows the relative abundance of acidic, main peak, and basic species of a mAb after IEX.

DETAILED DESCRIPTION

Figure 1:
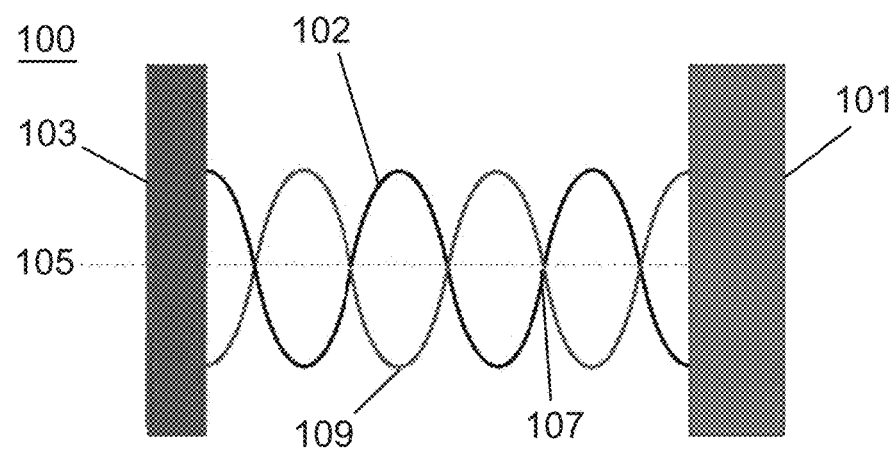
FIG. 1 illustrates a single standing acoustic wave generated by an ultrasonic transducer and a reflector.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The present application refers to "the same order of magnitude." Two numbers are of the same order of magnitude if the quotient of the larger number divided by the smaller number is a value of at least 1 and less than 10.

The term "beads" is used herein to refer to microspheres, microbeads, nano beads, microcarriers and other micro and nano particulates that are in the micrometer and nanometer size range, which may be functionalized or non-functionalized, and are composed of any one or more of a variety of materials and may be of one or more various shapes.

Bioreactors are useful for making biomolecules such as recombinant proteins or monoclonal antibodies. Very generally, cells are cultured in a bioreactor vessel with media in order to produce the desired product, and the desired product is then harvested by separation from the cells and media in an acoustic perfusion device, such as the device of the present disclosure. The acoustic filtering device permits the withdrawal of some desired product, a small portion of the media, and cellular fragments/debris smaller than the cells, with the remainder being recycled back to the bioreactor (particularly the cells). The use of mammalian cell cultures including Chinese hamster ovary (CHO), NSO hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies used in various applications such as pharmaceuticals or vaccines. Two general types of bioreactor processes exist: fed-batch and perfusion.

While fed-batch reactors are the norm currently, due mainly to the familiarity of the process to many scientists and technicians, perfusion technology is growing at a very fast rate. Many factors favor the use of a perfusion bioreactor process, primarily because it is conducive to continuous production. The capital and start-up costs for perfusion bioreactors are lower, there is a smaller demand on upstream and downstream capacity, throughput can be higher, the process is continuous, and the process uses smaller volumes and fewer seed steps than fed-batch methods. A perfusion bioreactor process also lends itself better to development, scale-up, optimization, parameter sensitivity studies, and validation.

A perfusion bioreactor may also be utilized to generate cells that would be utilized in a cell therapy process. In this type of perfusion bioreactor, biological cells such as CAR T-cells, Jurkat T-cells and the like are cultured in a perfusion bioreactor. The acoustic standing wave used in the perfusion devices of the present disclosure can be used to separate viable and nonviable cells after the transfection process. This separation ability allows for improved efficacy of the inoculation of the patient with this T-cell therapy, since viable cells may be primarily utilized. The nonviable cells and cell fragments are separated out through the perfusion process, with these materials going into the secondary flow and exiting the bioreactor.

A perfusion bioreactor may also be used for production of exosomes, microvesicles, or vesicles by cells. The acoustic perfusion device can then be used to harvest the exosomes, or other desired cell products, or other targets in a host fluid. In a similar fashion, a perfusion bioreactor can be used to produce viruses, such as lentivirus, which are used in cell and gene therapy to transfect cells. The acoustic perfusion device can then be used to harvest the virus. In all cases, the device is a cell retention device.

Recent developments in perfusion bioreactor technology also favor its use. Control technology and general support equipment is improving for perfusion bioreactors, increasing the robustness of perfusion processes. The perfusion process can now be scaled up to bioreactors having a volume up to 1000 liters (L). Better cell retention systems for perfusion bioreactors result in lower cell loss and greater cell densities than have been seen previously. Cell densities greater than 50 million cells/mL are now achievable, compared to fed-batch cell densities of around 20 million cells/mL. Lower contamination and infection rates have improved the output of perfusion bioreactors. Higher product concentrations in the harvest and better yields without significant increase in cost have thus resulted for perfusion processes.

Perfusion bioreactors are particularly attractive because of the continuous production of the biomolecules from the expressing cell culture, and shorter residence time of said biomolecules in the process prior to harvest. The target cells are held back by a filtration process, such as tangential flow filtration (TFF) or alternating tangential flow filtration (ATF) while the expressed biomolecules are extracted from the perfusion bioreactor. The cells are returned to the bioreactor to receive the nutrition and oxygen to maintain the production of the overall cell culture. In the perfusion reactor process, the cells continue to multiply, and some cells may be removed or bled off from the cell culture population throughout the perfusion production process.

The TFF and ATF processes of filtration have several issues, such as clogging/fouling and loss of biomolecule product (particularly at high cell densities), all directly related to the nature of the hollow fiber membranes used in the filtration. It is therefore desirable to find a new filtration process that does not clog and minimizes loss of the desired biomolecule product. In addition, TFF and ATF will retain all cellular debris and fines within the bioreactor, which is not desirable. A process capable of distinguishing between cell retention while allowing for the passing of cell debris and fines may therefore be favorable.

Briefly, the present disclosure relates to acoustic perfusion devices capable of generating multi-dimensional acoustic standing wave(s) from one or more piezoelectric transducers, where the transducers are electrically excited such that they move in a multi-mode displacement pattern rather than a "piston" mode of vibration. Through this manner of acoustic standing wave generation, a higher lateral trapping force is generated than if the piezoelectric transducer is excited in a "piston" mode where one large standing wave is generated. Thus, with the same input power to a piezoelectric transducer, the multi-dimensional acoustic standing waves can have a higher lateral trapping force compared to a planar acoustic standing wave. The input power is tunable for a controlled flow. This tunability can be used to facilitate proteinaceous fluid purification of a fluid stream coming from a bioreactor. Alternatively, the acoustic standing wave may also be a planar standing wave where the piezoelectric transducer is excited in the piston mode, generating a planar wave. The acoustic standing wave(s) may also be a combination of planar and multi-dimensional acoustic standing waves. All of these standing waves generate an "interface effect" such that the cells from the bioreactor are held back and the biomolecule product expressed from the cells, cell fragments and small debris are allowed to pass through.

Acoustophoresis is a low-power, no-pressure-drop, no-clog, solid-state approach to particle separation from fluid dispersions (i.e., it is used to achieve separations that are more typically performed with porous filters, but it has none of the disadvantages of filters). In particular, the acoustic perfusion devices of the present disclosure are suitable for use with macro-scale bioreactors for separations in flowing systems with high flow rates. The acoustic perfusion device is designed to create a high intensity multi-dimensional ultrasonic standing wave that results in an acoustic radiation force that can overcome the combined effects of fluid drag and buoyancy or gravity at certain flow rates. As a result, the radiation force acts as a filter that prevents targeted particles (e.g., biological cells) from crossing through the standing wave. As explained above, the trapping capability of a standing wave may be varied as desired, for example by varying the flow rate of the fluid, the acoustic radiation force, and the shape of the acoustic filtering device to maximize cell retention through trapping and settling. This technology offers a green and sustainable alternative for separation of secondary phases with a significant reduction in cost of energy. Excellent particle separation efficiencies have been demonstrated for particle sizes as small as one micron.

Generally, an acoustic standing wave generates pressure minima at locations on the standing wave where the amplitude is minimum and maximum. These are called, respectively, nodes and anti-nodes. These pressure minima nodes and anti-nodes may be utilized to capture materials that are differentiated from the surrounding environment by size, density and compressibility (i.e., the speed of sound through the material). Those materials that collect at the pressure minima nodes are known as having a positive contrast factor. Those materials that collect at the pressure minima anti-nodes are known as having a negative contrast factor.

In a typical experiment, the system is driven such that the particles are trapped in the ultrasonic standing wave, i.e., remain in a stationary position. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that contributes to trapping the particle. The forces acting on the particle may be greater than the combined effect of fluid drag force and gravitational force.

Generally, the scattering of the acoustic field off the particles results in a three-dimensional acoustic radiation force, which acts as a three-dimensional trapping field. The acoustic radiation force is proportional to the particle volume (e.g., the cube of the radius) when the particle is small relative to the wavelength. The force is proportional to frequency and the acoustic contrast factor. The force also scales with acoustic energy (e.g., the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the lateral and axial acoustic forces on the trapped particles results in formation of tightly packed clusters through concentration, clustering, clumping, agglomeration and/or coalescence of particles that, when reaching a critical size, settle continuously through enhanced gravity for particles heavier than the host fluid or rise out through enhanced buoyancy for particles lighter than the host fluid. Additionally, secondary inter-particle forces, such as Bjerkness forces, aid in particle agglomeration. Relatively large solids of one material can thus be separated from smaller particles of a different material, the same material, and/or the host fluid through enhanced gravitational/buoyancy separation.

Most biological cell types present a higher density and lower compressibility than the medium in which they are suspended, so that the acoustic contrast factor between the cells and the medium has a positive value. As a result, the axial acoustic radiation force (ARF) drives the cells towards the standing wave pressure nodes. The axial component of the acoustic radiation force drives the cells, with a positive contrast factor, to the pressure nodes, whereas cells or other particles with a negative contrast factor are driven to the pressure anti-nodes. The radial or lateral component of the acoustic radiation force is the force that traps the cells. The radial or lateral component of the ARF is larger than the combined effect of fluid drag force and gravitational force. For small particles or emulsions, the drag force $F_D$ and Stokes' drag $F_{SD}$ can be expressed as:

$$\vec{F}_D = 4\pi\mu_f R_P (\vec{U}_f - \vec{U}_P) \left[ \frac{1 + \frac{3}{2}\hat{\mu}}{1 + \hat{\mu}} \right], \vec{F}_{SD} = 6\pi\mu_f R_P \vec{V}_s \quad (1)$$

where $U_f$ and $U_p$ are the fluid and particle velocity, $R_p$ is the particle radius, $\mu_f$ and $\mu_p$ are the dynamic viscosity of the fluid and particle, respectively, $\hat{\mu} = \mu_p/\mu_f$ is the ratio of dynamic viscosities, and $\vec{V}_s$ is the particle settling velocity given by:

$$V_S = \frac{2(\rho_p - \rho_f) g R_P^2}{9\mu_f} \quad (2)$$

where $\rho_f$ is the fluid density, $\rho_p$ is the particle density, and g is the universal gravitational constant.

The gravity/buoyancy force $F_B$ is expressed as:

$$F_B = 4/3\pi R_p^3 g(\rho_f - \rho_p) \quad (3)$$

For a particle to be trapped in the ultrasonic standing wave and develop into a particle cluster, the force balance on the particle can be assumed to be zero, and therefore an expression for lateral acoustic radiation force $F_{LRF}$ can be found, which is given by:

$$F_{LRF} = F_D + F_B \quad (4)$$

For a particle of known size and material property, and for a given flow rate, this equation can be used to estimate the magnitude of the lateral acoustic radiation force.

The theoretical model that is used to calculate the acoustic radiation force is the formulation developed by Gor'kov, where the primary acoustic radiation force $F_A$ is defined as a function of a field potential U, $F_A = -\nabla(U)$, where the field potential U is defined as $$U = V_O \left[ \frac{\langle p^2(x,y,z) \rangle}{2\rho_f c_f^2} f_1 - \frac{3\rho_f \langle v^2(x,y,z) \rangle}{4} f_2 \right] \quad (5)$$

and $f_1$ and $f_2$ are the monopole and dipole contributions defined by $$f_1 = 1 - \frac{1}{\Lambda \sigma^2} \quad f_2 = \frac{2(\Lambda-1)}{2\Lambda+1} \quad (6)$$

where $$\sigma = \frac{c_p}{c_f} \quad \Lambda = \frac{\rho_p}{\rho_f} \quad \beta_f = \frac{1}{\rho_f c_f^2} \quad (7)$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o = \pi R_p^3$ is the volume of the cell, and $\langle \rangle$ indicates time averaging over the period of the wave.

For a one dimensional standing wave, the acoustic pressure is expressed as $$p = A \cos(kx)\cos(\omega t) \quad (8)$$

where A is the acoustic pressure amplitude, k is the wavenumber, and $\omega$ is the angular frequency. In this case, the axial component of the acoustic radiation force $F_{ARF}$ is found to be $$F_{ARF} = V_O k X \frac{A^2}{4\rho_f c_f^2} \sin(2kx) \quad (9)$$

where X is the contrast factor given by $$X = \left( \frac{5\Lambda - 2}{1 + 2\Lambda} - \frac{1}{\sigma^2 \Lambda} \right) \quad (10)$$

Particles with a positive contrast factor will be driven to the pressure nodal planes, and particles with a negative contrast factor will be driven to the pressure anti-nodal planes. In this way, the generation of a multi-dimensional acoustic standing wave in a flow chamber results in the creation of tightly packed clusters of particles in the flow chamber, typically corresponding to the location of the pressure nodes or anti-nodes in the standing wave depending on acoustic contrast factor.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces without any restriction as to particle size relative to wavelength was therefore used. The models that were implemented are based on the theoretical work of Yurii Ilinskii and Evgenia Zabolotskaya as described in AIP Conference Proceedings, Vol. 1474-1, pp. 255-258 (2012) and "Acoustic radiation force of a sphere without restriction to axisymmetric fields," Proceedings of Meetings on Acoustics, Vol. 19, 045004 (2013). These models also include the effect of fluid and particle viscosity, and therefore are a more accurate calculation of the acoustic radiation force. With these models, the acoustic radiation force is defined by $$\vec{F}_{Az} = \quad (11)$$

$$\frac{i}{4} K k^2 \sum_{n=0}^{n_{max}} \sum_{m=-n}^{n} \sqrt{\frac{(n+m+1)(n-m+1)}{(2n+1)(2n+3)}} [A_n^* + A_{n+1} + 2A_n^* A_{n+1}]$$

$$a_{n,m}^* a_{(n+1,m)} + c.c.$$

where $a^*_{n,m}$ and $a_{(n+1,m)}$ are the expansion coefficients of external field potential with respect to spherical functions $j_n(kr)Y_{n,m}(\theta,\phi)$, $Y_{n,m}(\theta,\phi)$ are spherical harmonies, $A_n$ is the scattering coefficient for mode (m,n), K is bulk modulus, and k is the wavenumber in the liquid.

Cells that have a low contrast factor compared to the fluid in which they are transported are more difficult to separate using an acoustic standing wave. Through specialized perturbations of a piezoelectric material, higher order modes of vibration in the piezoelectric material may be generated. When this piezoelectric material that is perturbed in a multimode fashion is coupled with a reflector, a specialized type of acoustic standing wave, known as a multi-dimensional acoustic standing wave, is generated. In this way, target biological cells having low cell concentrations (e.g., T cells) may be separated from a fluid medium utilizing a multi-dimensional acoustic standing wave. The target biological cells are generally at lower concentrations than, for example, a CHO cell population with 30 million cells per mL versus a concentration of 1 million cells per mL for Jurkat T cells. Thus, the low contrast cells, such as Jurkat T cells, in a low population concentration are separated continuously from the fluid media within which they are entrained by utilizing a multi-dimensional acoustic standing wave.

Desirably, the ultrasonic transducer(s) generates a multi-dimensional standing wave in the fluid that exerts a lateral force on the suspended particles to accompany the axial force. The multi-dimensional standing wave generates acoustic radiation forces in both the axial direction (e.g., in the direction of the standing wave, between the transducer and the reflector, which may be at an angle across the flow direction, and in some instances may be perpendicular to the flow direction) and the lateral direction (e.g., in the flow direction or transverse to the direction between the transducer and the reflector). As the mixture flows through the acoustic chamber, particles in suspension experience a strong axial force component in the direction of the standing wave. Since this acoustic force is across (e.g. perpendicular to) the flow direction and the drag force, it quickly moves the particles to pressure nodal planes or anti-nodal planes, depending on the contrast factor of the particle. The lateral acoustic radiation force acts to move the concentrated particles towards the center of each planar node, resulting in clustering, agglomeration or clumping. The lateral acoustic radiation force component can overcome fluid drag for such clumps of particles, to continually grow the clusters, which can exit the mixture due to gravity or buoyancy. The drop in drag per particle as the particle cluster increases in size, as well as the drop in acoustic radiation force per particle as the particle cluster grows in size, may separately or collectively influence operation of the acoustic separator device. In the present disclosure, the lateral force component and the axial force component of the multi-dimensional acoustic standing wave are of the same or different order of magnitude. In some particular embodiments, the ratio of the lateral force component to the axial force component is about 0.5 or less. In this regard, it is noted that in a multi-dimensional acoustic standing wave generated by a single transducer, the axial force is stronger than the lateral force, but the lateral force of such a multi-dimensional acoustic standing wave is much higher than the lateral force of a planar standing wave, usually by two orders of magnitude or more. Typical results published in literature state that the lateral force is two orders of magnitude smaller than the axial force. In contrast, the technology disclosed in this application provides for a lateral force to be of the same order of magnitude as the axial force. However, in certain embodiments described further herein, the device use both transducers that produce multi-dimensional acoustic standing waves and transducers that produce planar acoustic standing waves. For purposes of this disclosure, a standing wave where the lateral force is not the same order of magnitude as the axial force is considered a "planar acoustic standing wave." The lateral force component of the total acoustic radiation force (ARF) generated by the ultrasonic transducer(s) of the present disclosure is significant and is sufficient to overcome the fluid drag force at linear velocities of up to 1 cm/s, and to create tightly packed clusters, and is of the same order of magnitude as the axial force component of the total acoustic radiation force.

The average size of microvesicles, such as exosomes (i.e., about 150 nanometers in diameter or smaller), makes it difficult to separate the same using normal acoustophoretic techniques. Through the use of beads, the acoustic footprint or contrast factor of the exosomes may be increased dramatically by functionalizing the surface of the bead such that it will attach to the exosomes and create a moiety that is subject to acoustophoresis through its high contrast factor. The beads may have either a positive or negative contrast factor. Positive contrast factor materials include polystyrene beads, glass beads and other materials whose density is greater than that of the host fluid that contains the exosomes. Negative contrast factor materials of interest include microbubbles, micro-glass spheres and other low-density beads that may be functionalized to attract exosomes and thus increase their contrast factor footprint. The functionalization of the beads may be by, for example, attachment of CD 9, CD 63, CD 81, or EP CAM.

The acoustophoresis separation processes of the present disclosure may be coupled with other techniques, such as field flow fractionation where the ultrasonic wave is utilized to fractionate the materials entrained in a fluid stream, such as the exosome moieties or the beads that are carrying the exosomes through affinity binding. The acoustophoresis separation processes of the present disclosure may also be coupled with tangential flow filtration in a flow field that is bounded by the acoustic standing wave.

In the case of exosomal separation, an efficient and cost effective platform for complete isolation and segregation of extracellular vesicle populations from cell culturing, without the potential for lysis to occur, is possible with the acoustic tangential flow filtration processes described herein, whereas the detrimental processes of rupture and deactivation would happen with physical filtration and/or centrifugation. With emphasis on yielding pure exosome or oncosome populations that are morphologically and functionally intact, the acoustic tangential flow filtration process offers a great improvement. The acoustic tangential flow filtration process technology is readily adapted to enable automated workflows and reduce human intervention, enable closed loop systems, and to obtain the enriched distinct preparations of exosomes and oncosomes used to provide diagnostic determinations and selective therapeutic product.

Figure 40:
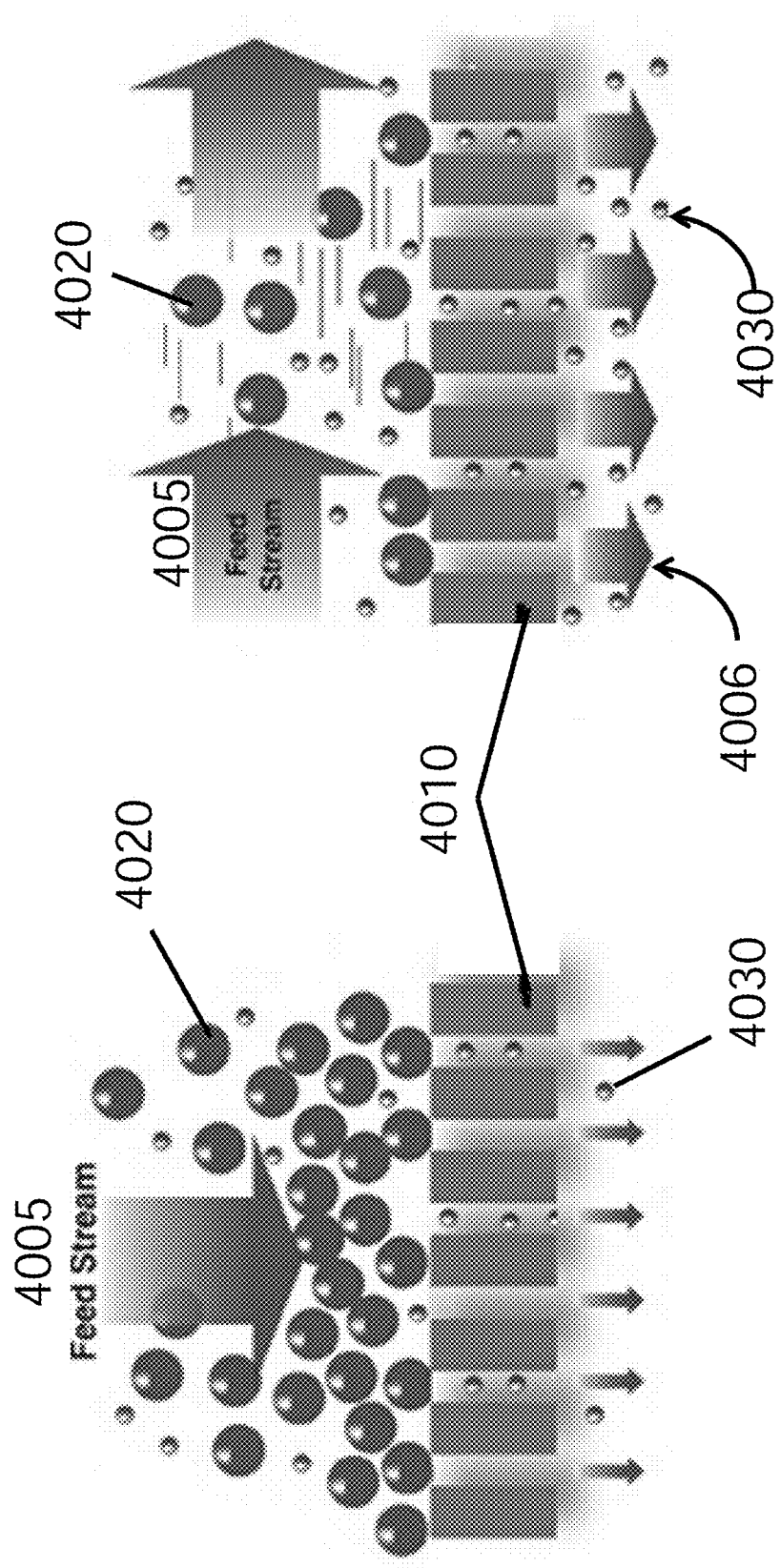
FIG. 40 is a prior art illustration showing direct flow filtration (DFF) and tangential flow filtration (TFF).

It may be helpful to contrast the technology of the present disclosure with that of prior filtration technology. FIG. 40 shows two prior art filtration methods. The left-hand side of FIG. 40 illustrates direct flow filtration (DFF). In DFF, the entire feed stream 4005 of fluid and particles is directed towards the filter. The filter 4010 holds back the particles 4020 that are larger than the filter's pore size, whereas smaller particles 4030 and the fluid pass through the filter. The right-hand side of FIG. 40 illustrates tangential flow filtration (TFF). In TFF, the feed stream is not directed towards the filter. Rather, the feed stream is directed tangentially to the filter, such that a majority of the feed stream passes tangentially over the filter surface. Typically, this feed stream is recirculated to pass by the filter more than once. A much smaller filtrate stream 4006 is pulled through the filter membrane containing the smaller particles 4030. One advantage of TFF over DFF is that the tangential stream reduces the clogging and fouling of the filter and the formation of a gel layer that sits on top of the filter.

In the devices of the present disclosure, during startup, the fluid ensonified by the acoustic standing wave is clarified by the process of trapping cells and growing them into tightly packed clusters, such that continuous gravitational separation of the clusters of cells takes place. Since there is a limited amount of new cells flowing into this volume, this results in a rapid clarification of the fluid subjected to the acoustic standing wave. When this state is reached, the system can be described as including two fluids: a first fluid containing the desired product and small cell fragments/debris (which have passed through the acoustic standing wave), and a second fluid containing the bioreactor fluid and all of the cells (which are held back by the acoustic standing wave). The two fluids may be of different effective acoustic properties, such as density and speed of sound, with a well-defined interface between these two fluids. The acoustic standing wave is a three-dimensional acoustic field, which, in the case of excitation by a rectangular transducer, can be described as occupying a roughly rectangular prism volume of fluid. Typically, two opposing faces are the transducer and reflector, an adjacent pair of opposing faces are the walls of the device, and the final opposing pair of faces, the upstream and downstream faces of the cube, extend through the fluid. The interface between the two fluids is generally located near the upstream face of the acoustic standing wave field, generating an "acoustic barrier or edge effect". This location is also referred to as an upstream interface region. The first fluid (i.e., the fluid that has been clarified and contains the product, some cells, and cell fragments) is downstream of the interface and represents the harvest flow and occupies the volume of fluid ensonified by the acoustic standing wave field. The second fluid (i.e., the fluid containing the bioreactor fluid and most of the cells) is upstream of the interface. These two different fluids can be seen in the photo on the right in FIG. 33. During operation at increased flow rates, the interface effect location may move downstream and is then located within the volume of fluid ensonified by the transducer.

The acoustic standing wave field exerts an acoustic radiation pressure (i.e. a pressure rise) and an acoustic radiation force on the cells at the interface region between the two fluids, thereby keeping the upstream cells from entering the acoustic field. The occurrence of the radiation pressure and the force on the interface allows for the first fluid containing the product to pass through the interface while retaining the cells in the upstream fluid. The cells that are held back by the effect of the acoustic radiation force at the interface between the two fluids can be continuously returned to the bioreactor to ensure they receive the nutrition and oxygen to maintain the production of the overall cell culture.

The circulating motion of the flow field underneath the interface transports the cells that are retained by the acoustic field back to the bioreactor. The circulating flow motion is driven by the primary recirculation stream and can be optimized with acoustic chamber geometry variations for maximum system efficiency. This process or configuration is discussed further below with respect to FIG. 33.

Figure 41:
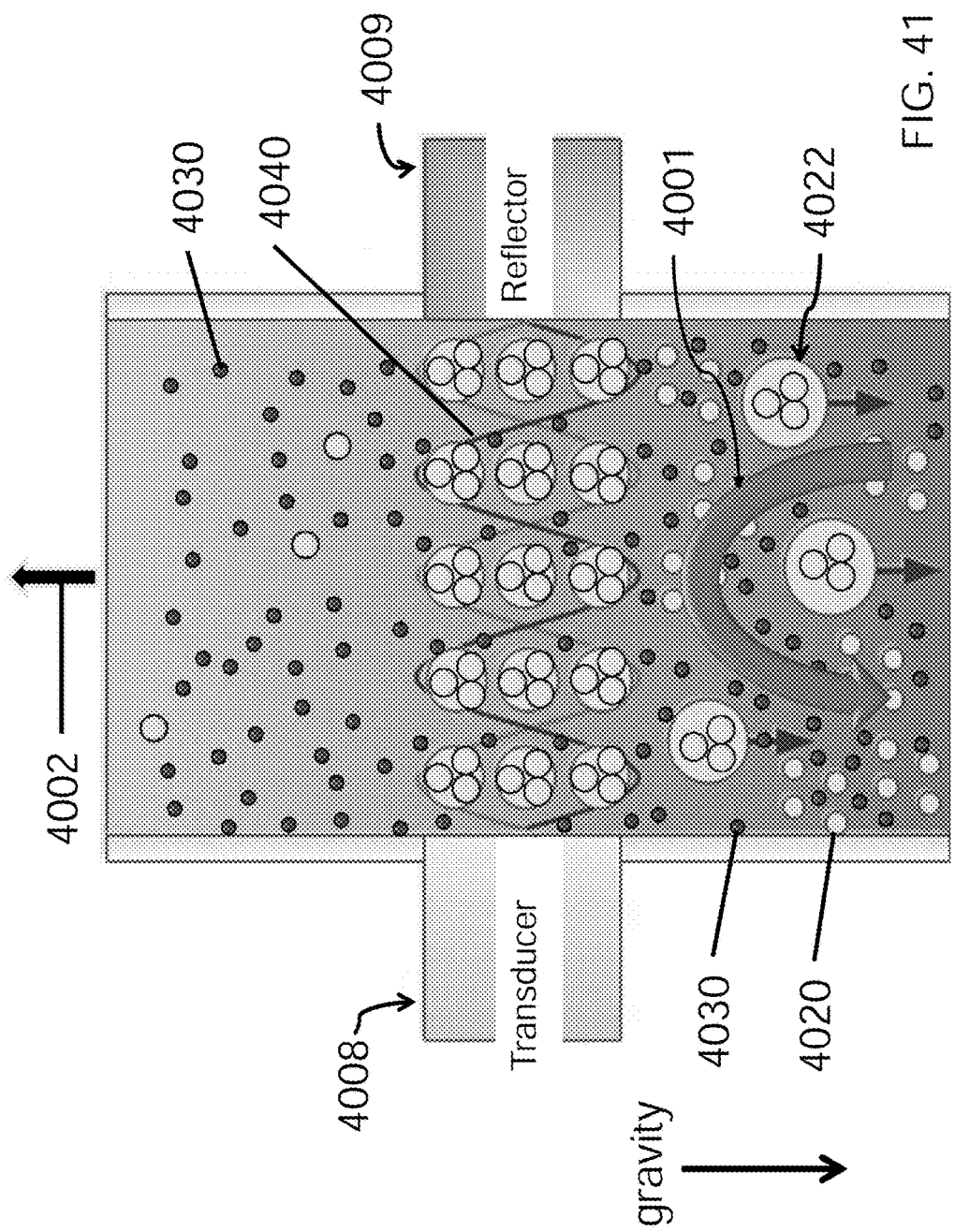
FIG. 41 is a picture illustrating a first mode of operation during perfusion, in which cells are trapped, clustered, and separated from a harvest stream. The device is operated vertically, with an arrow indicating the direction of gravity.

During perfusion, the acoustic perfusion devices of the present disclosure have multiple possible modes of operation. One of these modes may be dominant in the device or they may occur concurrently depending on the distribution of cells and fluid within the device. In a first mode of operation illustrated in FIG. 41 (Mode 1), the fluid containing larger particles 4020 (light color) enters the acoustic standing wave field 4040, which is produced here between transducer 4008 and reflector 4009. A multi-dimensional acoustic standing wave traps the particles at specific points, packs the particles into tightly packed clusters 4022, and continuously separates the clusters through enhanced gravitational settling. The particle clusters settle out, enter the tangential flow path (indicated by arrow 4001) and are redirected to the bioreactor by the recirculation stream. Smaller particles 4030 (darker color) are not trapped by, and pass through, the acoustic standing wave, to be harvested. The harvest flow direction is indicated by arrow 4002. The orientation of this device is significant, and the direction of gravity is also indicated. In particular embodiments, the larger particles 4020 can be cells and the smaller particles 4030 can be cell debris and/or fines. In other embodiments, the larger particles 4020 can be beads and the smaller particles 4030 can be cells or exosomes (or more generally the desired target material). In other embodiments, the larger particles 4020 can be beads with attached antibodies and the smaller particles 4030 can be cells that are not targeted by the functionalized beads.

Figure 42:
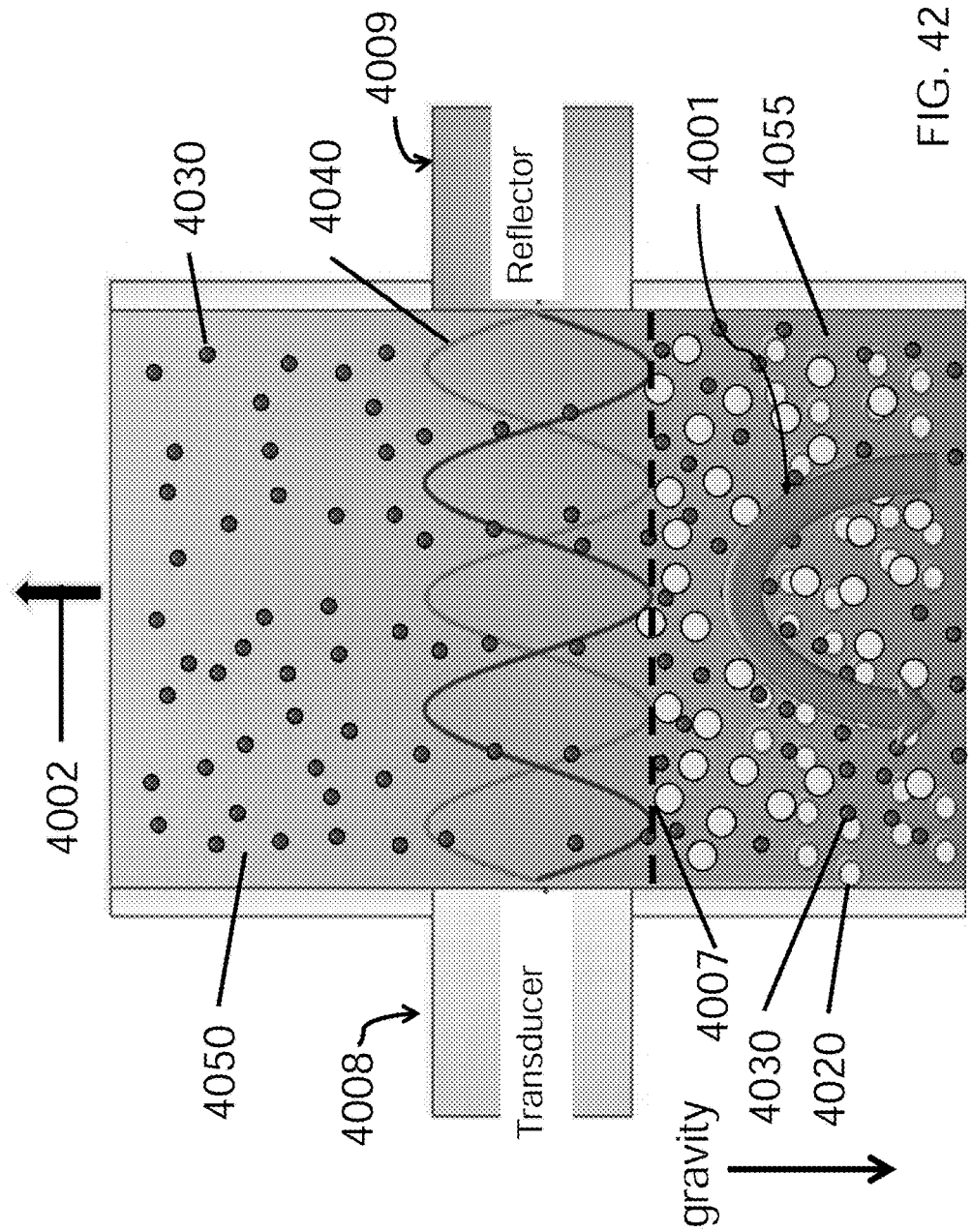
FIG. 42 is a picture illustrating a second mode of operation during perfusion, in which cells are prevented from entering an acoustic standing wave field while smaller particles are permitted to pass through the field and into the harvest stream. The device is operated vertically, with an arrow indicating the direction of gravity.

The second mode of operation (Mode 2) is illustrated in FIG. 42, where the acoustophoretic system creates a strong barrier for cells at the interface between the two fluids and prevents cells from entering the acoustic field. Here, a barrier of cells is established between the two fluids through the interface effect of the acoustic standing wave. A first clarified fluid stream 4050 contains the smaller particles/desired byproducts 4030 within the acoustic standing wave field and the harvest stream. A second fluid stream 4055 contains the retained cells 4020 upstream of the acoustic standing wave field. The harvest flow direction is indicated by arrow 4002. In this mode of operation, an acoustic interface effect is realized, as indicated by dotted line 4007 (representing the interface region between the two fluids, clarified fluid downstream and flow mixture and cells on the upstream side). Very generally, the acoustic interface effect holds the cells back and prevents them from entering the acoustic field while a portion of the fluid stream containing the produced biomolecules and cell fragments is permitted to pass through this barrier. The tangential flow path underneath the acoustic interface (arrow 4001) collects the retained cells and flows them back into the main recirculation stream and back to the bioreactor. This recirculation is discussed further below with respect to FIG. 32 and FIG. 61. Again, the direction of gravity is indicated in the figures. Alternatively, the second fluid stream 4055 can contain desired target material which is retained within the perfusion device, and the first fluid stream 4050 can be returned to the bioreactor.

Figure 32:
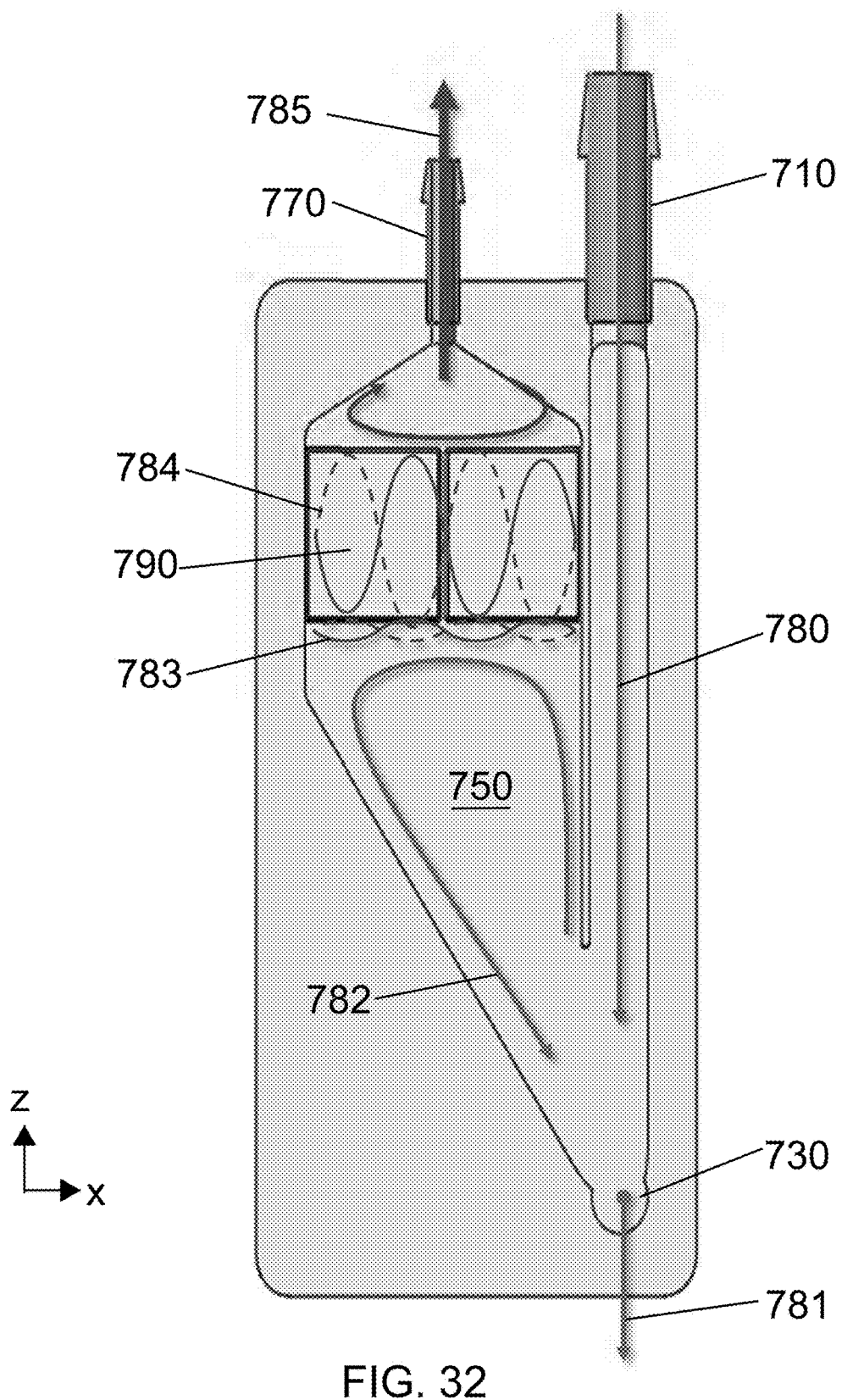
FIG. 32 is a front view of the device of FIG. 27, showing the flow paths, acoustic field, and acoustic interface effect.
Figure 61:
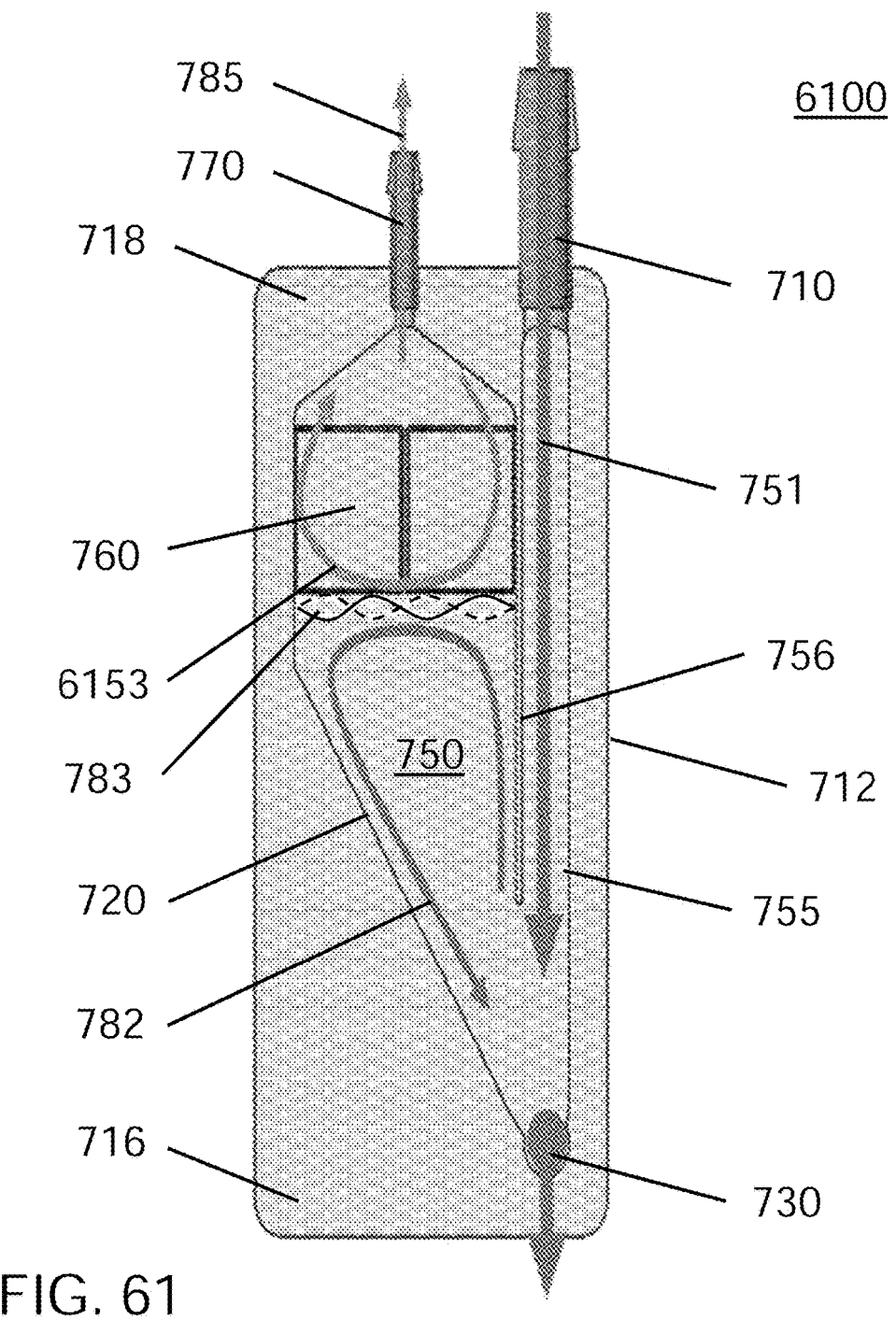
FIG. 61 is a front cross-sectional view of a seventh exemplary embodiment of an acoustic perfusion device of the present disclosure.
Figure 62:
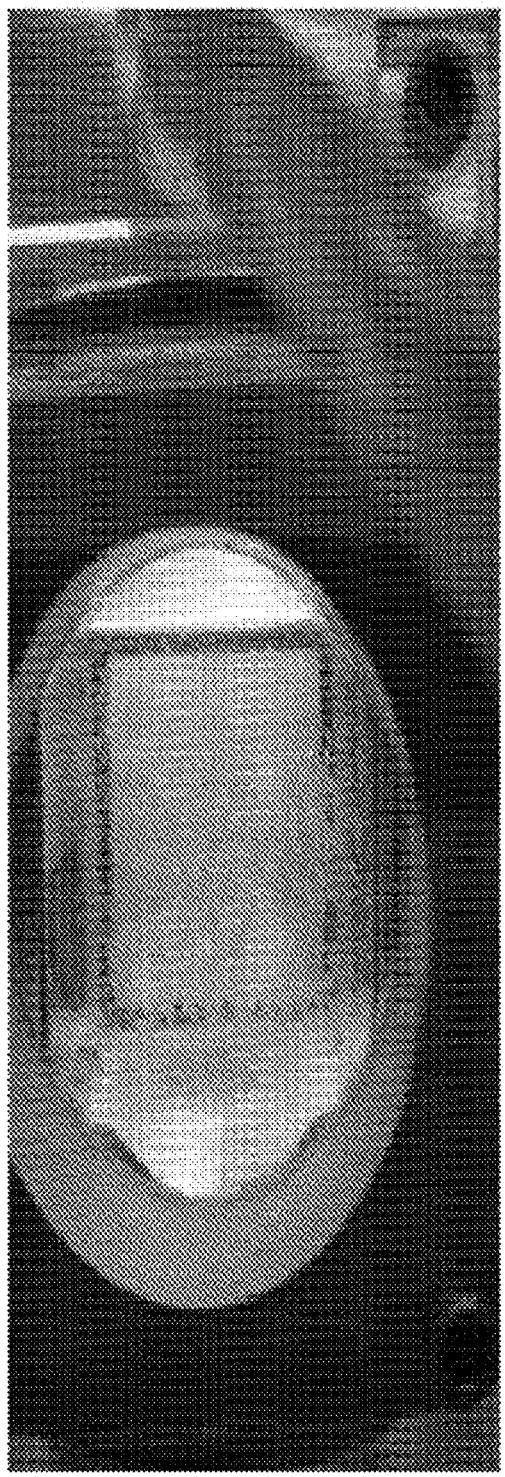
FIG. 62 is a front view photograph of a working 1 inch by 1 inch by 1 inch separator system using a 1 inch by 1 inch crystal to separate beads from a yeast mixture.

In perfusion applications, the setup of the acoustophoretic device is similar to that of TFF. A feed stream containing the cells, cell debris, fines, and product, i.e., protein, flows from the bioreactor into the perfusion system. A portion of the stream flows in a tangential fashion along the upstream/lower interface region of the acoustic standing wave and is recirculated back to the bioreactor. A smaller portion of the feed stream is harvested, i.e., diverted and flows through the acoustic standing wave. Here the acoustic standing wave functions very similarly to the filter in TFF, preventing the cells from entering the acoustic field. The harvest stream contains smaller particles such as cell debris and fines as well as the desired biomolecule product. The cells that are retained by the acoustic standing wave are transported by the recirculation stream back to the bioreactor. FIG. 32 and FIG. 61, which are discussed further herein, also illustrate perfusion devices that use a tangential flow stream.

Perfusion applications typically entail high cell densities, e.g., >50 million cells/mL, and lower harvest velocities contrary to cell clarification or oil/water applications. The two fluid streams also have different effective acoustic properties, i.e., speed of sound and density of the media/cell mixture. As cell density increases, the difference in acoustic properties of the two fluid streams are more pronounced. The acoustic standing wave field exerts an acoustic radiation pressure, i.e., a pressure rise, on the second fluid stream, enriched with cells, as well as acoustic radiation forces on the cells suspended in the fluid. This radiation pressure and radiation force act at the interface between the two fluids which coincides with the upstream bounding surface of the acoustic field. When this "acoustic interface" effect of acoustic radiation force is sufficiently strong, it can prevent the cells from entering the acoustic field. Equally important is a tangential flow path to collect the retained cells and transport them back to the bioreactor.

The acoustic interface effect may also be referred to as an acoustic wall effect and results from the interface of the acoustic field exerting a strong lateral force (i.e., in the opposite direction to the harvest flow and perpendicular to the axis of the acoustic standing wave) on the suspended particles, thereby keeping the relatively larger sized particles from entering the acoustic field and allowing clarified fluid (i.e., the fluid containing the smaller-sized product) to enter the acoustic field, thereby creating an acoustic perfusion cell retention device. In this way, the clarified fluid can escape and the cells are held down by the radiation force. This force is never positive, meaning that it always holds the cells down at the interface, i.e., the force is acting in the upstream flow direction, not allowing the cells to pass through the acoustic interface. The multiple peaks in the power curve (see discussion of FIG. 36 below) show the existence of multiple modes of operation including planar resonance modes and multi-dimensional modes of operation, indicating that this type of operation can be generated through utilization of planar and multi-dimensional standing waves alike. In systems having 1"×1" dimensions, there exists a planar resonance about every 30 kHz. FIG. 36 shows evidence of additional peaks indicating the existence of the multi-dimensional modes. Per unit power, these modes can be equally or even more effective as the planar resonance modes. As explained above, the cells that are held back by the acoustic radiation force may then picked up by the scrubbing motion of the fluid flow field (i.e., the recirculating flow underneath the interface), and be continuously returned to the bioreactor to ensure they receive the nutrition and oxygen to maintain the production of the overall cell culture.

The clarified fluid contains both the desired products and cell fragments, all of which are smaller than whole viable cells. In this way, the media that is returned to the bioreactor is clarified of cell fragments. Cell fragments absorb media without producing desired product, making the perfusion process less efficient. Thus, there is an efficiency gain and a cost savings obtained by removing these cell fragments using the acoustic perfusion devices of the present disclosure. Further clarification of the clarified fluid may be achieved downstream using a second device or a secondary flow chamber that contains another transducer-reflector pair that operates at a different frequency. This arrangement traps, clumps, clusters, or agglomerates particles having a size of about 10 microns or less that may have passed through the original acoustic standing wave, in the same manner as described before. A third transducer-reflector pair operating at another frequency, 3 MHz to 20 MHz, or higher, may be utilized to trap, clump, cluster, or agglomerate and drop out the small cell fragments and debris that passed through the initial acoustic standing wave and the "interface effect". This triple-clarified fluid containing the desired biomolecules can then directly enter a sterile filter. For example, the original acoustic perfusion device may operate at frequencies up to about 4 MHz. It is contemplated that the frequency of this second and third acoustic standing wave field would be from about 6 MHz to about 20 MHz, and possibly higher, to trap smaller sized cell fragments.

Figure 33:
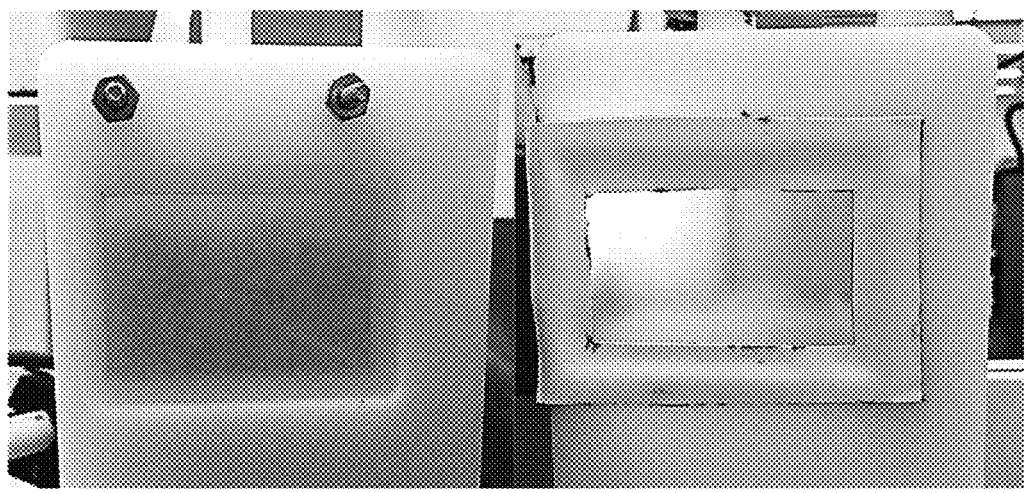
FIG. 33 is a composite photograph showing the acoustic perfusion device of FIG. 27 in two operating modes. On the left, the device is in startup or cell settling mode. On the right, the device is in steady cell retention mode.

During startup of a bioreactor at low cell density, e.g., 2 million cells/mL, the first described mode of operation dominates (FIG. 33, left image). As cell density in the bioreactor increases over time, the mode of operation gradually switches from mode 1 to mode 2, and both modes may coexist at the same time.

When an acoustic standing wave is employed for perfusion in a bioreactor with an already high cell density, e.g., 50 million cells/mL, the device typically starts in the first mode of operation (FIG. 33, left image), until the volume of fluid within the acoustic standing wave is clarified, at which point the operation gradually switches to the second described mode of operation (FIG. 33, right image). At times, during operation, an instability, usually manifested as a perturbation or oscillation of the interface between the two fluids, may grow sufficiently strong such that cells enter the volume of fluid within the acoustic standing wave, at which point, for a short period of time, the device acts in a combined mode of operation, where both modes are active (i.e., the interface effect prevents cells from entering the acoustic field as explained above, while the acoustic field clarifies the cells that have entered the volume of fluid within the acoustic standing wave field). Once the tightly packed cell clusters have settled out (i.e., once the volume of fluid within the acoustic standing wave has been sufficiently clarified), the mode of operation is then again that of the second described mode of operation, namely, the acoustic interface effect. It is important to note that the device can operate in both/either of the modes of operation, as described above, without external switching. In other words, the properties of the fluid streams, e.g., cell concentrations in the streams, and acoustic field dictate which mode dominates.

The acoustic standing wave(s) perfusion devices of the present disclosure are operated differently compared to prior acoustic filter usages, previously described in literature. Previously, acoustophoresis was operated such that the protein-producing materials, such as Chinese hamster ovary cells (CHO cells), the most common host for the industrial production of recombinant protein therapeutics, were trapped within a planar ultrasonic standing wave (i.e., remain in a stationary position). Cells were retained in an acoustic field by causing individual cells to migrate towards the pressure nodal planes of the planar acoustic standing wave. There, as the cells were retained in the standing wave, there was also a physical scrubbing of the cell culture media flowing past, whereby more cells were trapped as they came in contact with the cells that were already held within the standing wave. The standing wave and harvest fluid flow were then intermittently shut off to allow the cells to drop out of the standing wave and return to the bioreactor.

In contrast, in the present disclosure, the ultrasonic standing waves are used as a blanket or selector or "force field" in the perfusion device. The perfusion device is configured to permit fluid flows that are against gravity forces. The flows against gravity contribute to the biological cells sinking. The standing wave is created near the top of the filtering device and acts like a filter to prevent the cells from entering the acoustic field and exiting through the top of the filtering device (i.e., acting similar to a force field holding the cells back from entering the acoustic field). Thus, two output streams are created, one output stream retaining the cells and exiting through a port at the bottom of the device, and the other output stream being depleted in cells and exiting through a port at the top of the device (the cell concentration in the two output streams being compared to each other). In this mode of operation, there is almost no reliance on clustering, clumping, or agglomeration of the cells within the acoustic field to achieve separation. The combination of fluid dynamics and acoustic field to block cells is particularly advantageous in certain applications. Because the cells are not retained in the acoustic field for a period of time, the filtering device is more easily operated in a continuous arrangement.

Described another way, the acoustic perfusion device has two fluid streams flowing at different rates. The main fluid stream, carrying the expressing cell culture, culture media, product, and other bioreactor constituents, enters the device and is partially diverted into a secondary, lower volume, lower flow fluid stream. This secondary fluid stream passes through the multi-dimensional acoustic standing wave, where the multi-dimensional acoustic standing wave (or generally the interface effect created by the acoustic standing wave) holds back the main cell culture and allows the expressed biomolecules, the monoclonal antibodies and recombinant proteins, along with other small particles such as submicron and micron-sized cell debris, to pass through and be further collected and processed outside/downstream of the bioreactor. The main fluid stream, containing the main cell culture, is then recycled back to the bioreactor. The acoustic standing wave and its "interface effect" can be considered to act as a filter, preventing large cells, other particles or bodies, from exiting the bioreactor.

In another application, the acoustic perfusion devices can act as a retention device and cell washing device for cell therapy applications. In continuous cell-culture applications, such as autologous and allogeneic cell therapy, cells may be initially harvested at a very low cell-density. The cells may be purified, isolated and proliferated in the cell culture. Relatively few cells may be used to seed a bioreactor. The bioreactor may be used to increase the number of cells in the cell culture. Further processing steps such as concentrating, washing, and media exchange are all needed for various applications. The commonality in all these applications is the need to continuously circulate, add, and/or remove media while retaining cells in a bioreactor (which may be traditional or single-use) with no effect to their viability. The acoustic cell retention systems described herein operate over a range of cell recirculation rates, efficiently retain cells over a range of perfusion (or media removal rates), and can be tuned to fully retain or selectively pass some percentage of cells through fluid flow rate, transducer power or frequency manipulation. Power and flow rates can all be monitored and used as feedback in an automated control system. Specialty flow paths may also be used such that a small volume of the main fluid flow is "sipped" off and the expressed biomolecules are separated from the main cell culture.

One advantage of acoustophoresis is that the acoustic radiation force does not harm or negatively affect the biological cells or the desired biomolecule product. Moreover, perfusion is continuous, such that the cell culture is kept viable and desired products can be continually recovered therefrom.

In a perfusion bioreactor system, it is desirable to be able to filter and separate the viable biological cells from the expressed materials that are in the fluid stream (i.e., cell culture media) and cellular debris. As previously mentioned, such biological cells may include Chinese hamster ovary (CHO) cells, whose cell genome is manipulated to express large biomolecules. Such biomolecules can include recombinant proteins or monoclonal antibodies, and are the desired product to be recovered.

The acoustic perfusion devices of the present disclosure are designed to maintain a high intensity multi-dimensional acoustic standing wave that can act as a filter, permitting smaller particles (such as recombinant proteins or cellular debris) to pass through while excluding larger particles (such as viable cells). Generally, the device is driven by an oscillator and amplifier (not shown), and the device performance is monitored and controlled by a computer (not shown). The parameters of the energy or signal applied to the transducer, such as, for example, frequency or voltage amplitude, may be controlled and/or modulated. In some instances it may be desirable to control the applied signal to compensate for effects such as acoustic streaming. This control may be achieved by amplitude modulation and/or by frequency modulation. The duty cycle of the propagation of the standing wave may also be utilized to achieve certain results (i.e. the acoustic beam may be turned on and shut off at different time periods or rates).

Figure 63:
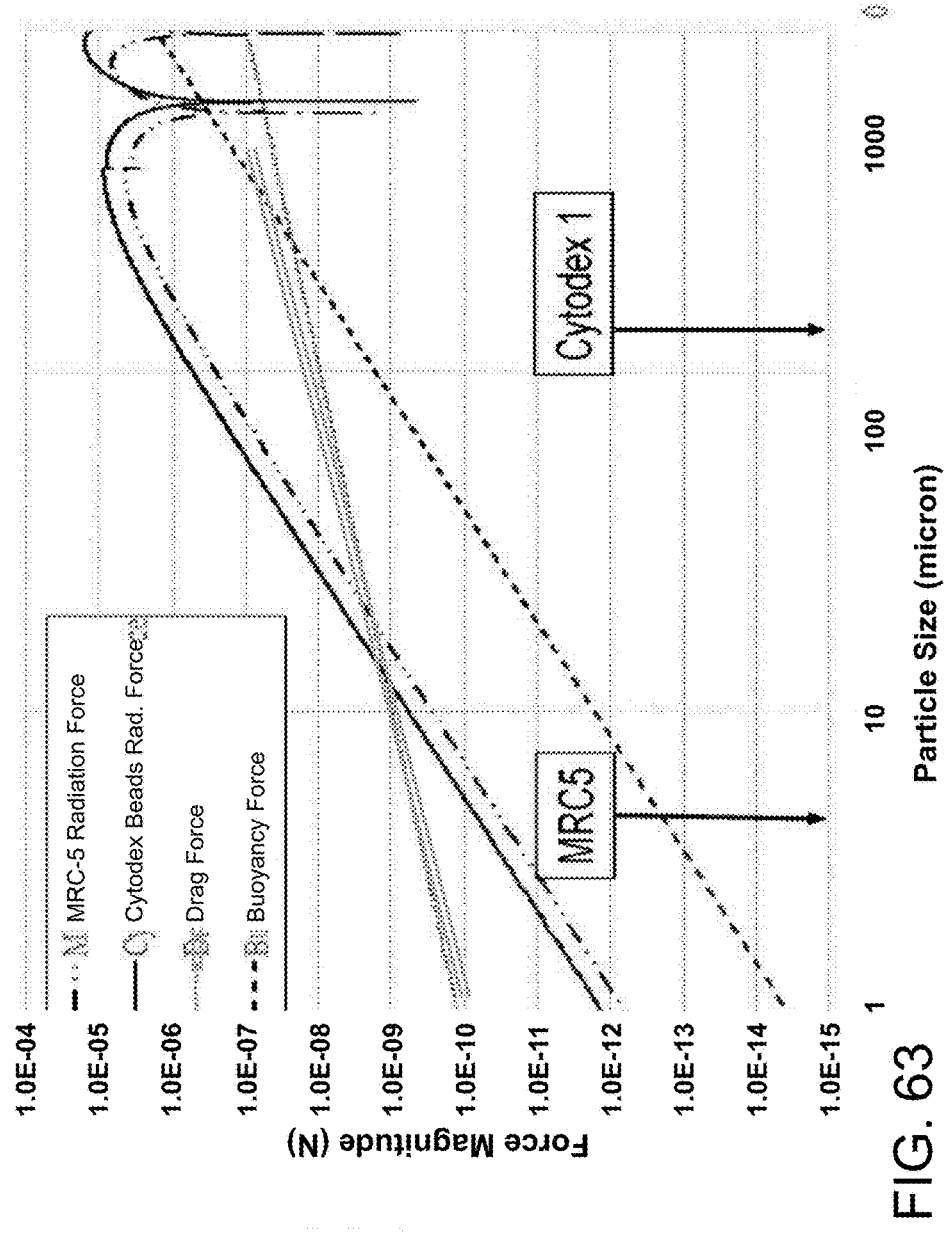
FIG. 63 is a log-log graph showing the relationship of the MRC-5 radiation force, the Cytodex beads radiation force, gravity/buoyancy force, and Stokes' drag force to particle size. The horizontal axis is in microns (μm) and the vertical axis is in Newtons (N).

FIG. 63 is a log-log graph (logarithmic y-axis, logarithmic x-axis) that shows the scaling of the radiation forces of cells (MRC-5) and microcarriers (Cytodex beads), fluid drag force, and buoyancy force with particle radius. The graph provides an explanation for the separation of microvesicles, cells or microcarriers from a host fluid based on parameter settings. For example, the frequency, flow rate (drag force) and power can be controlled and/or modulated to prevent or permit passage of microvesicles, cells or microcarriers. If the fluid flow is increased from that illustrated in the graph in FIG. 63, the drag force intersection with the radiation force curves rises along the curves and can pass the point where particles the size of Cytodex beads are repelled, so that microvesicles, cells and beads are all passing through the acoustic field. At the operating point illustrated in the graph, cells and microvesicles are passed, while the beads are repelled. Lowering the fluid flow until the intersection of the drag force line intersection with the radiation force curves is below the cell (MRCS) size causes microvesicles (which are smaller than cells and not shown on the graph) to pass, while cells and beads are repelled or retained by the acoustic field. Similar effects can be achieved by modulating and/or controlling frequency or power of the acoustic field. Thus, the perfusion systems disclosed herein can discriminate based on size with a relatively high level of distinction.

FIG. 1 illustrates a single standing wave system 100 that is comprised of a reflector plate 101 and an ultrasonic transducer 103 that is set to resonate so as to form a standing wave 102. Excitation frequencies typically in the range from 100 kHz to 100 MHz are applied by the transducer 103. One or more multi-dimensional standing waves are created between the transducer 103 and the reflector 101. An ideal standing wave is the sum of two propagating waves that are equal in frequency and intensity and that are traveling in opposite directions, i.e. from the transducer to the reflector and back. The propagating waves constructively interfere with each other and thus generate the standing wave. A dotted line 105 is used to indicate the zero-amplitude of the wave. A node is a point where the wave has minimum amplitude, and is indicated with reference numeral 107. An anti-node is a point where the wave has maximum amplitude, and is indicated with reference numeral 109. The standing wave is illustrated as beginning and ending with local maxima, however, other implementations are possible. For example, the standing wave can be offset at the transducer or the reflector so that local minima or maxima are spaced from the transducer or from the reflector. The reflected wave (or wave generated by an opposing transducer) can be in- or out-of-phase with the transducer generated wave. The characteristics of the standing wave can be modified and/or controlled by the drive signal applied to the transducer, such as by modifying and/or controlling the phase, amplitude, or frequency of the drive signal. Acoustically transparent or responsive materials may also be used with the transducer or reflector to modify and/or control the standing wave.

Figure 2:
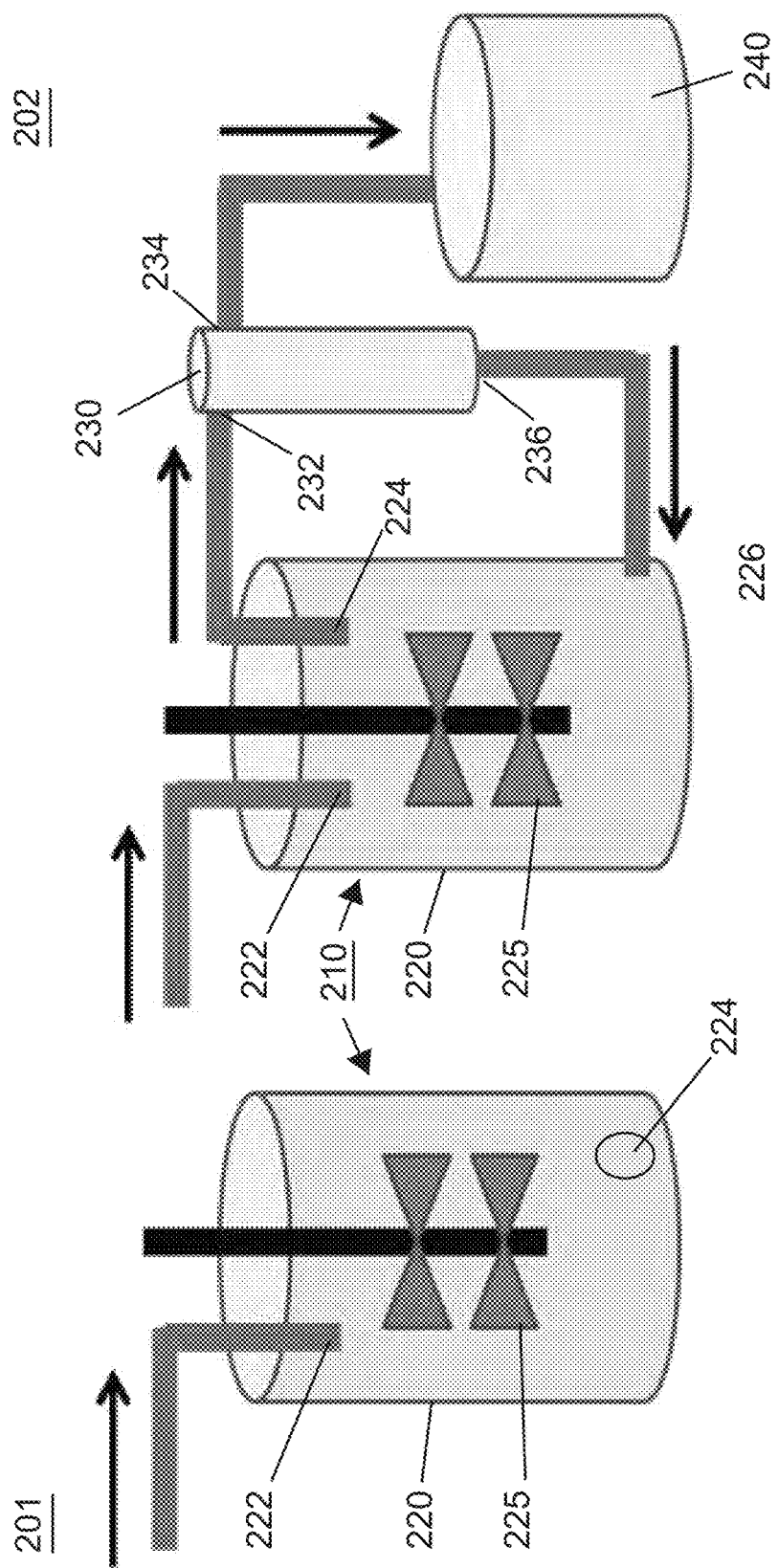
FIG. 2 is an illustration comparing a fed-batch bioreactor system with a perfusion bioreactor system.

FIG. 2 is a schematic diagram that compares a fed-batch bioreactor system 201 (left side) with a perfusion bioreactor system 202 (right side). Beginning with the fed-batch bioreactor on the left, the bioreactor 210 includes a reaction vessel 220. The cell culture media is fed to the reaction vessel through a feed inlet 222. An agitator 225 is used to circulate the media throughout the cell culture. Here, the agitator is depicted as a set of rotating blades, though any type of system that causes circulation is contemplated. The bioreactor permits growth of a seed culture through a growth/production cycle, during which time debris, waste and unusable cells will accumulate in the bioreactor and the desired product (e.g. biomolecules such as monoclonal antibodies, recombinant proteins, hormones, etc.) will be produced as well. Due to this accumulation, the reaction vessel of a fed-batch process is typically much larger than that in a perfusion process. The desired product is then harvested at the end of the production cycle. The reaction vessel 220 also includes an outlet 224 for removing material.

Turning now to the perfusion bioreactor 202 on the right-hand side, again, the bioreactor includes a reaction vessel 220 with a feed inlet 222 for the cell culture media. An agitator 225 is used to circulate the media throughout the cell culture. An outlet 224 of the reaction vessel is fluidly connected to the inlet 232 of an acoustic perfusion device 230 of the present disclosure, and continuously feeds the bioreactor contents (containing cells and desired product) to the filtering device. The perfusion device is located downstream of the reaction vessel, and separates the desired product from the cells. The acoustic perfusion device 230 has two separate outlets, a product outlet 234 and a recycle outlet 236. The product outlet 234 fluidly connects the acoustic perfusion device 230 to a containment vessel 240 downstream of the perfusion device, which receives the flow of the desired product (plus media) from the perfusion device. From there, further processing/purification can occur to isolate/recover the desired product. For example, further downstream of this acoustic perfusion device may be additional filters such as an ATF, TFF, depth filter, centrifuge, etc. The recycle outlet 236 fluidly connects the acoustic perfusion device 230 back to a recycle inlet 226 of the reaction vessel 220, and is used to send the cells and cell culture media back into the reaction vessel for continued growth/production. Put another way, there is a fluid loop between the reaction vessel and the perfusion device. The reaction vessel 220 in the perfusion bioreactor system 202 has a continuous throughput of product and thus can be made smaller. The filtering process is critical to the throughput of the perfusion bioreactor. A poor filtering process implies low throughput and results in low yields of the desired product.

Figure 3:
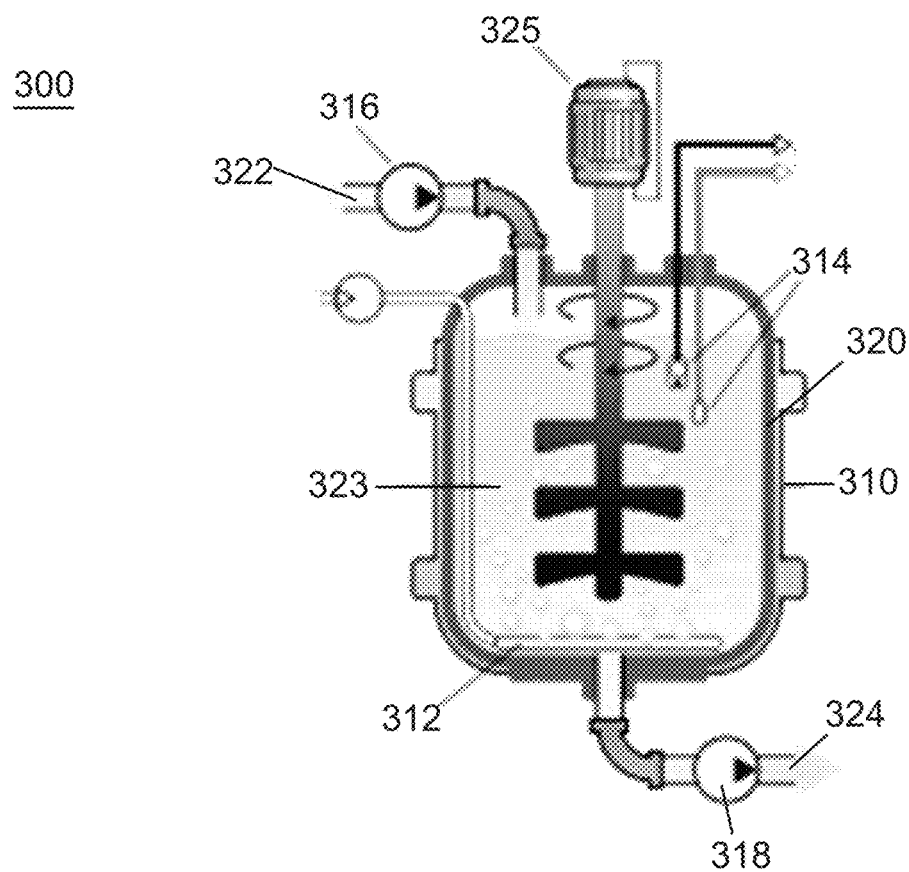
FIG. 3 is a cross-sectional view that shows the various components of a stirred-tank bioreactor.

FIG. 3 is a cross-sectional view of a generic bioreactor 300 that is useful for the systems of the present disclosure. As illustrated here, the bioreactor includes a reaction vessel 320 having an internal volume 323. A feed inlet 322 at the top of the vessel is used to feed cell culture media into the vessel. An agitator 325 is present. An outlet 324 is shown at the bottom of the vessel. A thermal jacket 310 surrounds the reaction vessel, and is used to regulate the temperature of the cells/media. An aerator 312 is located on the bottom of the vessel for providing gas to the internal volume. Sensors 314 are shown at the top right of the vessel. A pump 316 is illustrated for feeding the cell culture media into the vessel, as is another pump 318 for removing cell culture media from the vessel.

The perfusion systems described above use an acoustic perfusion device of the present disclosure. The contents of the bioreactor are continuously flowed through the acoustic perfusion device to capture the desired products.

Figure 4:
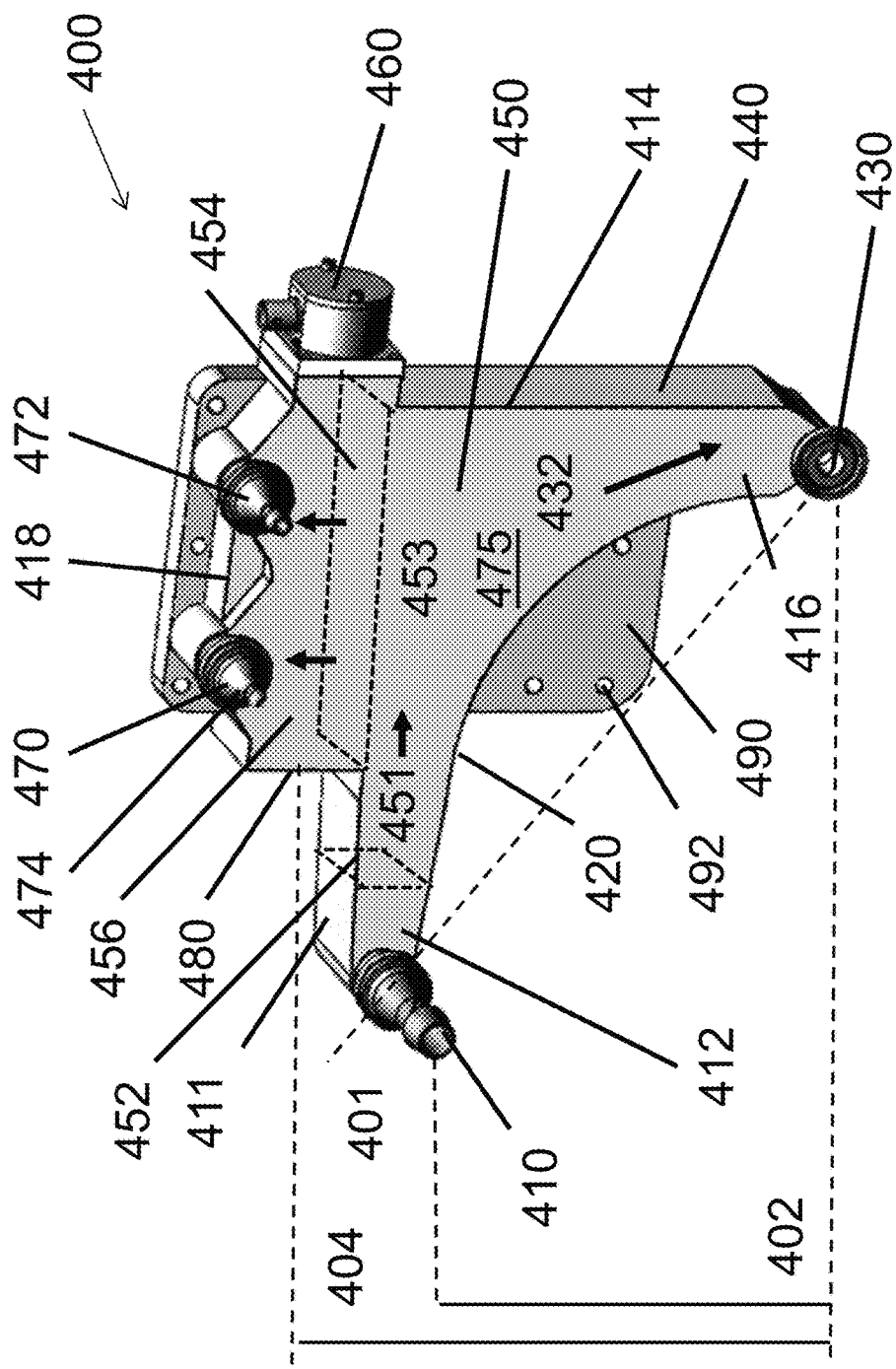
FIG. 4 is a perspective view of one exemplary embodiment of an acoustic perfusion device of the present disclosure, having two collection or harvest ports and a single ultrasonic transducer.

FIG. 4 is a first embodiment of an acoustic perfusion device 400 that can be used with the previously-described systems. The device includes an inlet port 410, an outlet port 430, a first collection port 470, a bottom wall 420, and an acoustic chamber 450. The acoustic chamber 450 can also be referred to as a fluid cell.

The inlet port 410 is located at a first end 412 of the device. Generally, the inlet port 410 is fluidly connected to an associated bioreactor and serves as the inlet through which the fluid mixture with cells, fines, and product is introduced to the device. An inlet flow path 451 leads from the inlet port 410 to the acoustic chamber 450, which contains an internal volume. An upper wall 411 can be present above the inlet flow path leading from the inlet port to the acoustic chamber, the upper wall having a substantially horizontal orientation. The inlet flow path has a cross-sectional area 452 (illustrated by the dotted square).

The inlet port 410 is located at a first height 402 above the outlet port 430, which defines a bottom end of the device. Put another way, the outlet port 430 is located below the acoustic chamber 450 or below the inlet port 410, or at the bottom end 416 of the device. The placement of the outlet port 430 below the inlet port 410 ensures that fluid flow through the device is passively urged by gravity towards the outlet port 430, and that a hydraulic head is created within the device. The outlet port 430 may also be referred to as a fluid recycle port because the host fluid is recycled or returned from the device to the associated bioreactor through the outlet port 430. As illustrated here, the outlet port 430 is also located at a second end 414 of the device, opposite the first end 412. The first end 412 and second end 414 can be considered as being opposite ends of an x-axis, while the bottom end 416 and top end 418 can be considered as being opposite ends of a z-axis.

The first collection port 470 is located above the acoustic chamber 450 at the top end 418 of the device, and is fluidly connected to the acoustic chamber. The device may include additional collection ports, such as second collection port 472, which is spaced apart from the first collection port 470. The first and second collection ports 470, 472 are generally used to harvest and recover a portion of the desired biomolecule byproducts from the device. A collection or harvest flow path 453 leads from the acoustic chamber to the collection ports 470, 472. The collection flow path has a cross-sectional area 454 (illustrated by the dotted square). In some particular embodiments, the cross-sectional area 454 of the collection flow path is greater than the cross-sectional area 452 of the inlet flow path. This arrangement provides one method by which the flow rate of fluid through the collection ports 470, 472 can be made much lower than the incoming flow rate of fluid. When used in perfusion biomanufacturing, the collection ports can also be referred to as perfusion or harvest ports. Because fluid depleted in cells and enriched in desired biomolecule products, cell debris, and other fines is harvested, the collection ports can also be referred to as harvest ports, and the collection flow path can also be referred to as the harvest flow path.

In this embodiment, the bottom wall 420 extends from the inlet port 410 to the outlet port 430 of the device. The exact shape of the bottom wall 420 can vary to obtain the desired fluid flow. As illustrated here, the bottom wall 420 curves from the inlet port 410 to the outlet port 430 of the device. Relative to a line between the inlet port 410 and the outlet port 430, illustrated as dotted line 401, the bottom wall 420 has a concave curve. An outlet flow path 432 leads from the acoustic chamber 450 to the outlet port 430.

As illustrated here, a first ultrasonic transducer 460 is located on a sidewall 440 of the device at a second height 404 that is above the first height 402 (i.e. closer to the top end 418 of the device) and below the collection ports 470, 472. This volume above the acoustic chamber 450 and below the collection ports 470, 472 is identified here as a harvest or collection zone 456. The first ultrasonic transducer 460 includes a piezoelectric material that can be driven by a drive signal to create a multi-dimensional standing wave in the acoustic chamber 450 across the collection flow path 453. An acoustic radiation force field thus separates the acoustic chamber 450 from the collection ports 470, 472.

In the embodiment of FIG. 4, the device includes a reflector 480 located on a wall opposite from the first ultrasonic transducer 460. The reflector is also located at the second height (i.e. the same height as the transducer). Together, the transducer 460 and reflector 480 generate a multi-dimensional acoustic standing wave, as illustrated in FIG. 1.

The inlet port 410, outlet port 430, and the collection ports 470, 472 are, in this illustrated embodiment, all located on a front wall 475 of the device. It is also contemplated that these ports can face in any other direction, as desired. The front wall 475 is illustrated here as having a flat or planar face, and has a constant thickness. However, the shape of the front wall may also vary if desired, for example to change the cross-sectional areas 452, 454. Finally, the rear wall of the device is attached to a mounting piece 490, which contains holes 492 for attaching the perfusion device to a surface for operation.

In use, the fluid mixture containing biological cells and smaller molecules enters the acoustic chamber 450 through the inlet port 410. Inside the acoustic chamber, gravity acts to drag the biological cells downwards towards the outlet port 430. A passive settling process occurs in the acoustic chamber, creating a fluid with a relatively high concentration of biological cells at the bottom end 416 of the device, and a fluid with a relatively lower concentration of biological cells at the top end 418 of the device. The vast majority of incoming fluid, and thereby, the large majority of the cell population never passes through the acoustic standing wave(s). The fluid with the high concentration of biological cells is pumped back to the bioreactor, and the fluid with the relatively low concentration of biological cells (and also containing desired biomolecules) is pumped out and collected though the collection port(s) 470, 472. The acoustic standing wave(s) of the device act to prevent significant numbers of biological cells from exiting through the collection port(s) 470, 472.

The flow rate through the collection or harvest flow path 453 is, in various embodiments, at least one order of magnitude smaller than the flow rate through the inlet flow path 451. In more particular embodiments, the flow rate of the fluid mixture entering the device through the inlet port is about 1 liter per minute (L/min) and the flow rate of the fluid depleted in cells exiting the device through the collection port(s) is about 10 milliliters per minute (mL/min). In some tests, bioreactors having a size of 2 liters to 10 liters have been tested with solutions containing up to 10% yeast and up to 50 million cells/m L. The flow rate through the inlet port has been from about 0.75 L/min to about 3 L/min, with the flow rate through the collection flow path (i.e. all collection ports together) being about 1 mL/min to about 30 mL/min. A 95% cell recovery rate has been achieved.

The acoustic perfusion devices of the present disclosure can filter very high cell densities, around 100 million cells per mL and possibly in the range of about 20 million to about 120 million cells per mL, whereas other filtering technologies such as ATF may be limited to being able to filter at densities less than 80 million cells per mL. Unlike hollow fiber membranes, the acoustic standing wave(s) can also be tuned to allow passage of cells if desired, as well as allow the passage of fines/debris. This tuning for material passage permits the acoustic standing wave(s) to perform a cleaning operation for the bioreactor. Continuous, steady-state operation is possible without pressure fluctuations, and the product stream does not accumulate in the bioreactor or the filtering device.

The acoustic perfusion device can be made of appropriate materials known in the art. Such materials include high density polyethylene (HDPE), other plastics, and potentially metals and glasses. It has been found very convenient for the device to be transparent, so that fluid flow and ultrasonic transducer operation can be visually confirmed.

Figure 5:
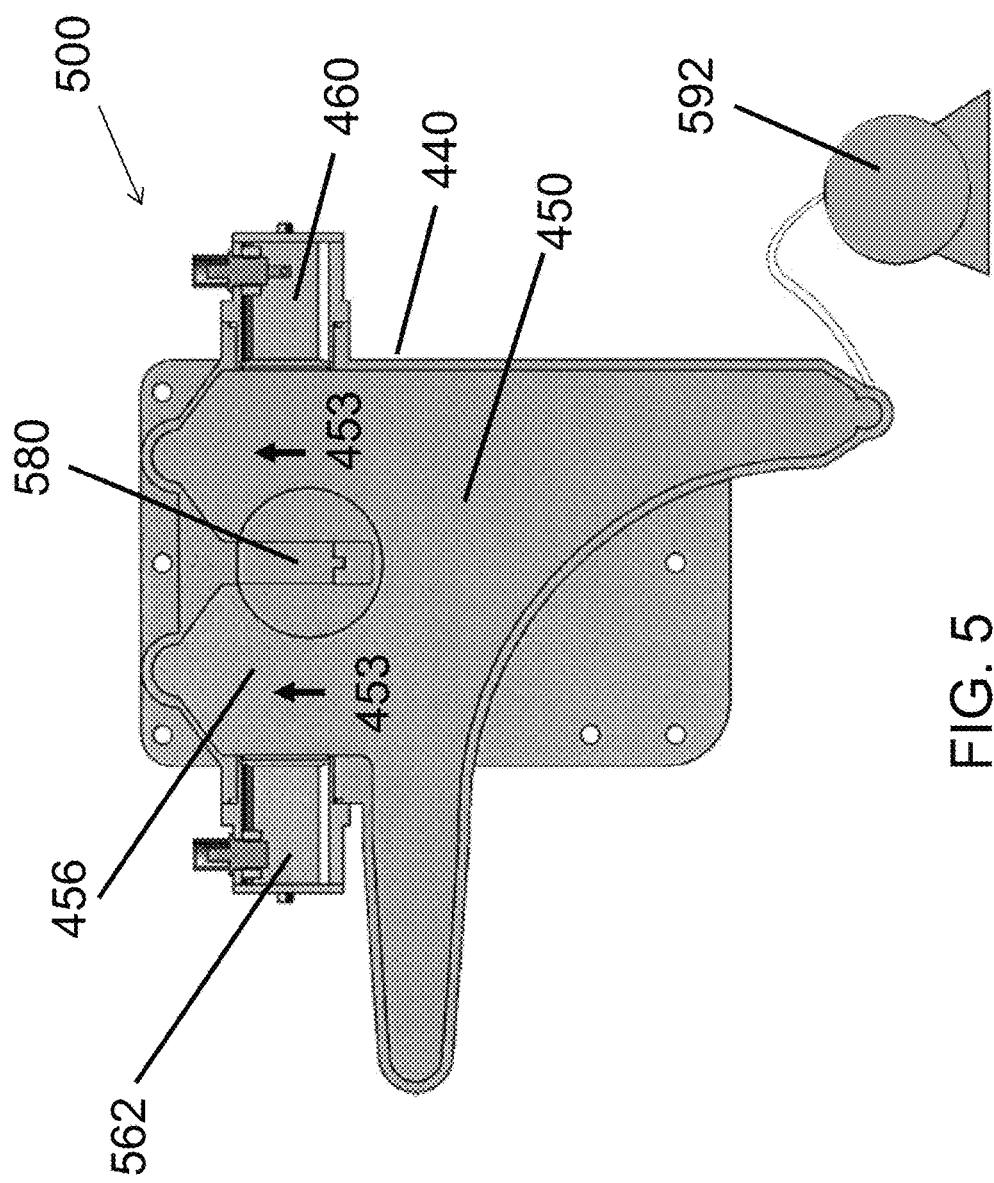
FIG. 5 shows a second exemplary embodiment of an acoustic perfusion device of the present disclosure, with a single reflector located between two ultrasonic transducers.

FIG. 5 shows another embodiment of an acoustic perfusion device 500. This embodiment is very similar to the device 400 depicted in FIG. 4. The main difference is that the acoustic perfusion device 500 of FIG. 5 has a first ultrasonic transducer 460 on one sidewall of the device and a second ultrasonic transducer 562 on an opposite sidewall 440 thereof in the collection zone 456. Put another way, the two transducers 460, 562 are located on opposite sides of the collection flow path 453. With this arrangement, the reflector 580 is located within the collection zone 456 between the first and second ultrasonic transducers 460, 562. The transducers are oriented so that the reflector 580 and first and second ultrasonic transducers 460, 562 create multi-dimensional standing wave(s) in the fluid cell 450 as described above, or put another way the transducers are facing each other. Also illustrated is the outflow pump 592 attached to the outlet port 430 of the device, which is used to control the flow rate of the fluid mixture flowing through the device. Not illustrated here is the pump attached to the collection ports (not visible) of the filtering device 500.

Figure 6:
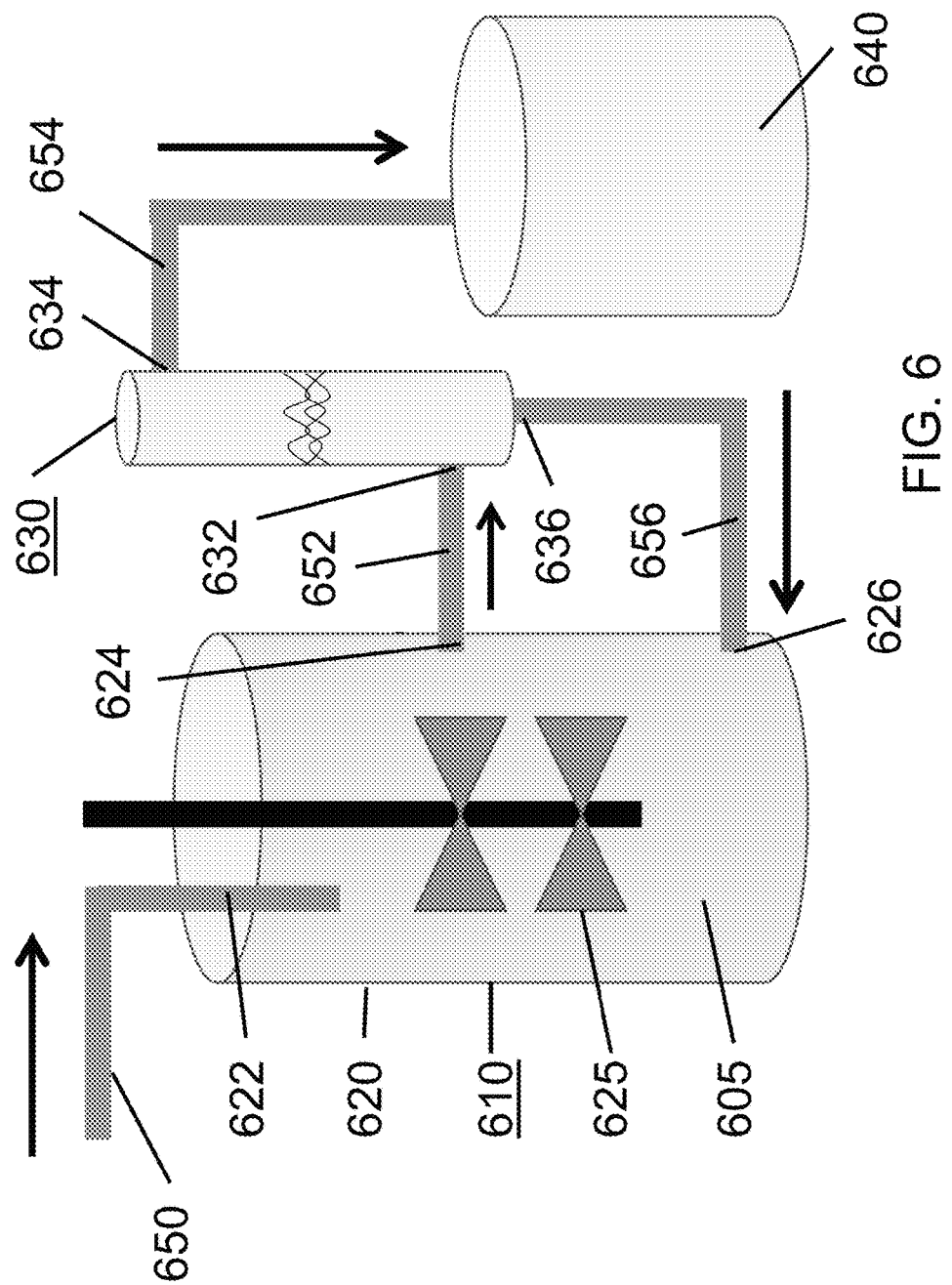
FIG. 6 is a schematic view illustrating a perfusion bioreactor coupled with an acoustic perfusion device of the present disclosure, and a recycle path.

Turning now to FIG. 6, a processing system is shown including an associated bioreactor 610 and an acoustic perfusion device 630 of the present disclosure. The system is set up for use as a perfusion bioreactor. The bioreactor 610 includes a reaction vessel 620 having a feed inlet 622, an outlet 624, and a recycle inlet 626. Fresh media is added into the feed inlet 622 by an addition pipe 650. Some reactors will also include an outlet or bleed port (not shown here) to remove or "bleed" cells in order to maintain a constant cell density within a reactor. The contents of the reaction vessel (reference numeral 605) are mixed with an agitator 625. The desired product (e.g., recombinant proteins) is continuously produced by cells located within the vessel 620, and are present in the media of the bioreactor. The product and the cells in the perfusion bioreactor are drawn from the reaction vessel through pipe 652, and enter the acoustic perfusion device 630 through inlet port 632. Therein, a portion of the desired product is separated from the cells. The desired product can be drawn off through a first collection port 634 (which is a product recovery port) and pipe 654 into a containment vessel 640, or in the case of a truly continuous production system, some other downstream purification process. The cells are returned to the perfusion bioreactor after separation, passing from outlet port 636 (which is a fluid recycle port) of the acoustic perfusion device through pipe 656 to recycle inlet 626 of the reaction vessel, which form a recycle path. The multi-dimensional standing wave(s) of the acoustic perfusion device are used to create a separation barrier between the fluid cell of the device and the collection port, so that a highly reduced number of biological cells are collected in collection port 634.

Figure 7:
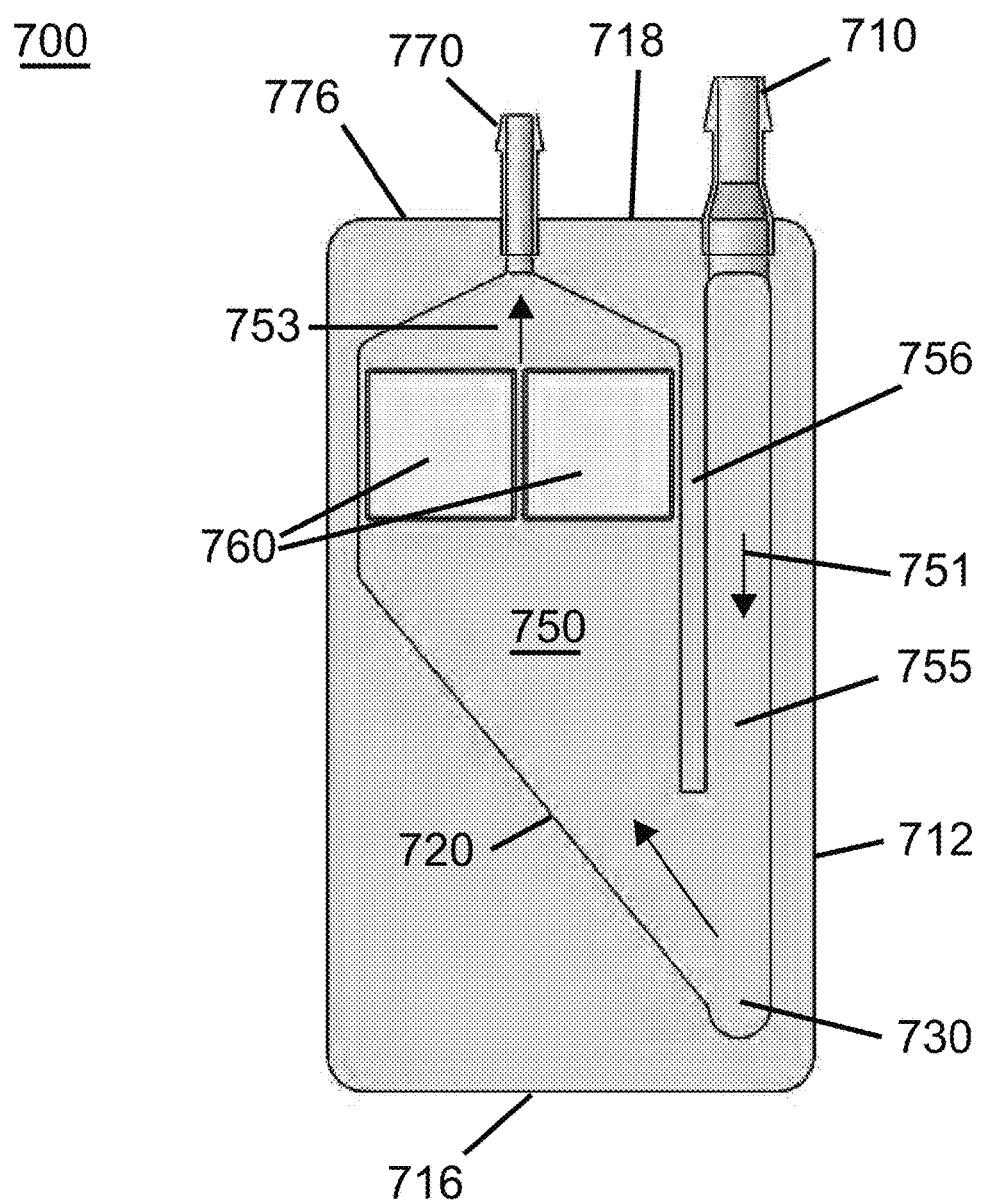
FIG. 7 is a front cross-sectional view of a third exemplary embodiment of an acoustic perfusion device of the present disclosure.
Figure 8:
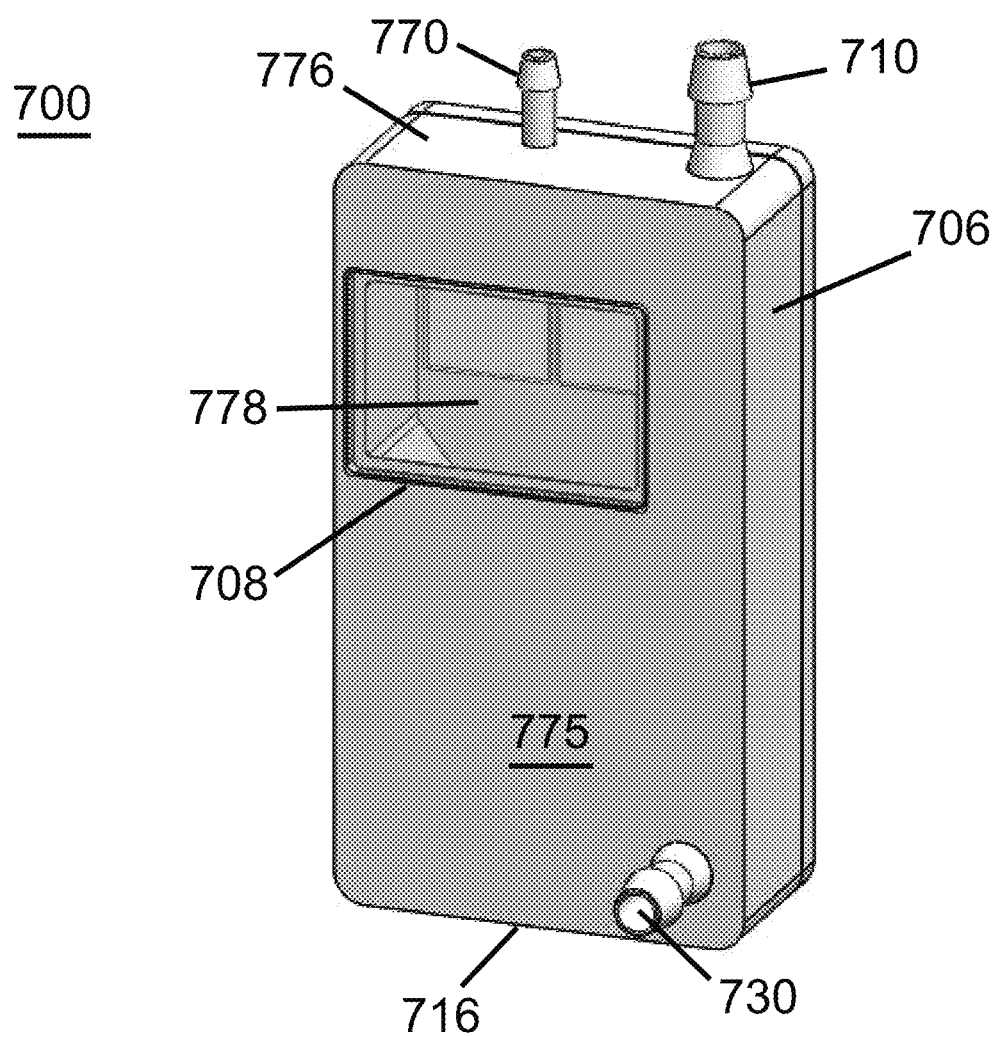
FIG. 8 is an exterior perspective view of the acoustic perfusion device of FIG. 7.

FIG. 7 and FIG. 8 are views of another exemplary embodiment of an acoustic perfusion device. FIG. 7 is a front cross-sectional view, and FIG. 8 is an exterior perspective view. Notably, this embodiment is specifically designed such that it can be fabricated with clean machining techniques, using Class VI materials (medical device grade HDPE, for example), or even as single or welded injection molded part. In this manner, this embodiment is an example of a single-use device, which is gamma-stable. The devices are flushed to remove bioburden and then gamma-irradiated (generally from 25-40 kGy) to sterilize any potential contamination that could destroy a healthy cell culture, such as that present in a perfusion bioreactor.

Referring first to FIG. 7, in this device 700, the inlet port 710 and the collection port 770 are both located at the top end 718 of the device, or on the top wall 776 of the device. The outlet port 730 is located at a bottom end 716 of the device. Here, the inlet port 710 and the outlet port 730 are both on a first side 712 of the device. The inlet flow path 751 is in the form of a channel 755 that runs from the inlet port downwards towards the bottom end and past the outlet port, the channel being separated from the acoustic chamber 750 (here, the separation occurring by an internal wall 756). Fluid will flow downwards in the channel, then rise upwards into the acoustic chamber 750. The bottom wall 720 of the acoustic chamber is a sloped planar surface that slopes down towards the outlet port 730. The location of the ultrasonic transducers 760 are shown here as two squares, between the top end and the bottom end of the device. The collection flow path 753 is located above the transducers.

Referring now to FIG. 8, the device 700 is shown as being formed within a three-dimensional rectangular housing 706. It can be seen that the outlet port 730 at the bottom end 716 of the device is located on a front wall 775. Again, the collection port 770 and the inlet port 710 are located on a top wall 776. A viewing window 708 made of a transparent material is present in the front wall. Through that viewing window, it can be seen that the ultrasonic transducers are mounted in the rear wall 778 of the device housing. The viewing window acts as a reflector to generate the multi-dimensional acoustic standing waves.

Figure 9:
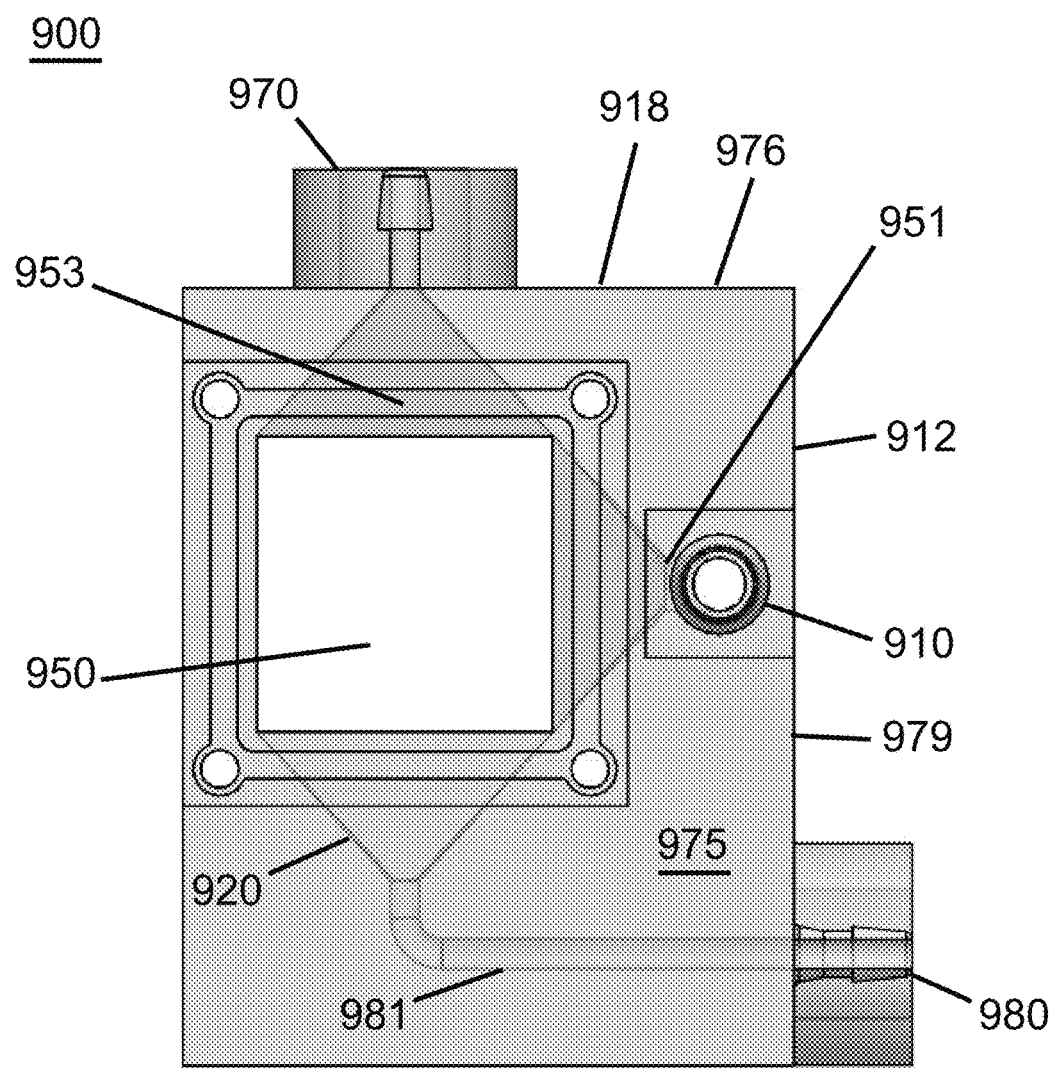
FIG. 9 is a front cross-sectional view of a fourth exemplary embodiment of an acoustic perfusion device of the present disclosure.
Figure 10:
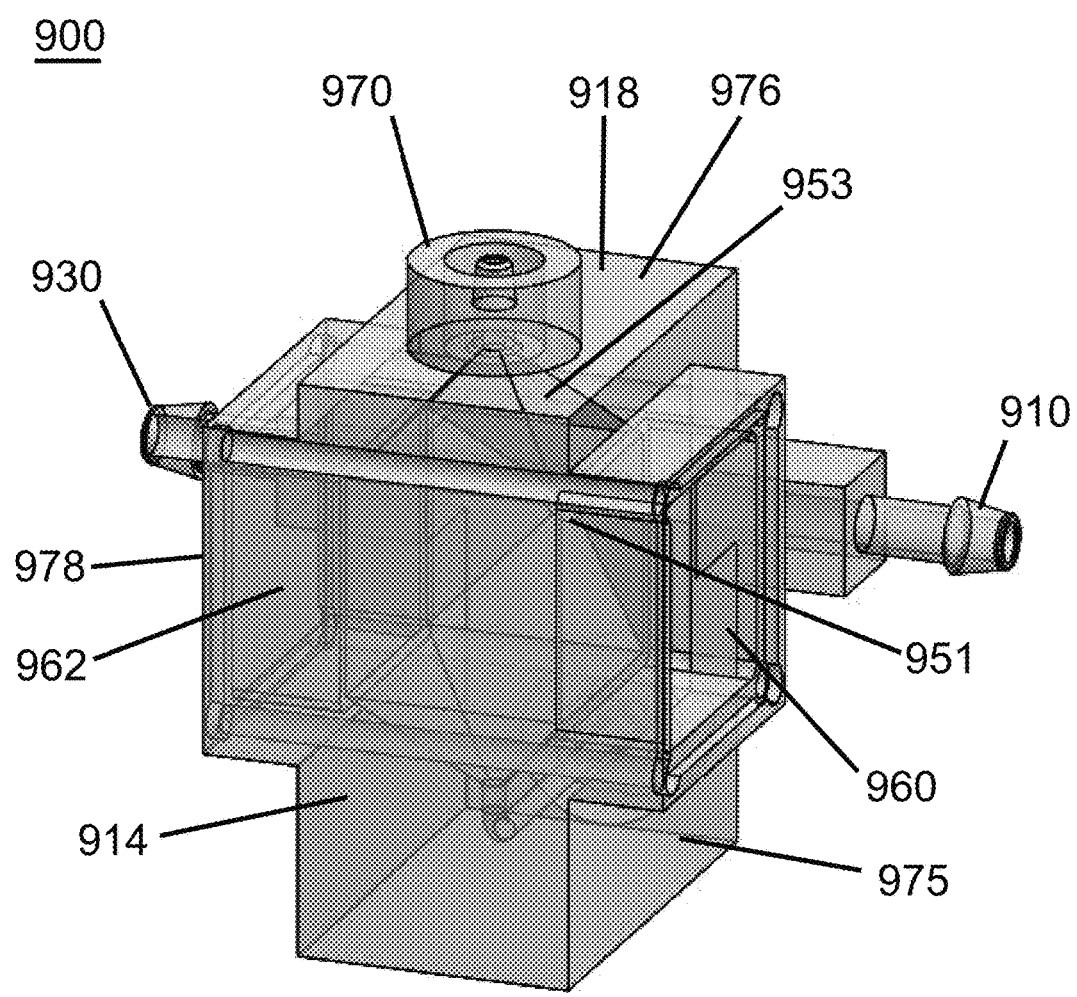
FIG. 10 is a perspective view of the acoustic perfusion device of FIG. 9.

FIG. 9 and FIG. 10 are views of yet another exemplary embodiment of an acoustic perfusion device. FIG. 9 is a front cross-sectional view, and FIG. 10 is a perspective view.

Referring first to FIG. 9, in this device 900, there is an inlet port 910 present on a front side 975 of the device along the first side 912 of the device. An outlet port 930 (best seen in FIG. 10) is located directly opposite and at the same height as the inlet port 910, and is also located on first side 912. In this embodiment, there is a main fluid stream that flows almost directly from the inlet port 910 to the outlet port 930, and the inlet flow path 951 diverts a small side flow into the acoustic chamber 950 from the first side 912 of the device. The collection port 970 is located at the top end 918 of the device, or on the top wall 976 of the device. A secondary outlet port 980 is located on the first side 912 of the device as well, extending from first side wall 979, and located below the inlet port 910, and can act as a bleed port. The bottom wall 920 of the acoustic chamber is shaped in a pyramid-like fashion to taper downwards to a vertex. A drain line 981 runs from the bottom of the acoustic chamber 950 to the secondary outlet port 980. It is contemplated that here, the secondary outlet port can be used to capture a small flow of highly concentrated cells, which can either be discarded (cell bleed) or can also be returned back to the bioreactor.

Referring now to FIG. 10, the front wall 975 of the device has a rectangular space 960, and the rear wall 978 of the device has a rectangular space 962. It is contemplated that one transducer and one reflector can be placed in these two rectangular spaces 960/962 in either orientation, or that two transducers could be placed in the two rectangular spaces. The inlet port 910 and outlet port 930 are both visible in this view. The inlet port 910 is located on the front side of the device, and the outlet port 930 is located on the rear side of the device (though this arrangement could be reversed if desired). The clarification flow path 953 is located above the transducers. Although not depicted here, a mounting piece similar to that in FIG. 4 could be attached to the second side 914 of the device.

FIGS. 43-45 are views of yet another exemplary embodiment of an acoustic perfusion device. FIG. 43 is a perspective view, FIG. 10 is a picture showing a front view, and FIG. 45 is a side view. FIG. 46A/B and FIG. 46C/D are schematic front views of possible interior layouts of the device. FIG. 46A and FIG. 46B are identical, and are used because of the large number of reference numerals. FIG. 46C and FIG. 46D are also identical Referring now to FIGS. 43-45, in this device 4300, the inlet port 4310 and the outlet port 4330 are both located at the bottom end 4316 of the device, and the collection port 4370 is located at the top end 4318 of the device. The inlet port 4310 is located on a first side 4312 of the device, and the outlet port 4330 is located on a second side 4314 of the device. In FIG. 43, the outlet port 4330 is attached to a pump 4305, which creates flow through the device 4300. A viewing window 4308 is present on the front wall 4375 of the device. The front wall 4375, top wall 4376, rear wall 4378, and first side wall 4379 are part of the housing 4306 that surrounds the interior of the device.

Referring now to FIG. 43 and FIG. 45, the ultrasonic transducer 4360 is located on the rear wall 4378 at the top end 4318 of the device. The viewing window 4308 acts as a reflector to generate the multi-dimensional acoustic standing waves.

In this embodiment, a recirculation pipe 4340 connects the inlet port 4310 directly to the outlet port 4330, and forms a recirculation flow path (arrow 4356) through which cell culture media containing cells and other materials can be continuously recirculated through the perfusion device without entering the acoustic chamber 4350. The recirculation pipe 4340 and the recirculation flow path 4356 are located below the acoustic chamber 4350.

An inflow passageway 4380 and an outflow passageway 4390 connect the acoustic chamber 4350 to the recirculation pipe 4340, and split off a portion of the flow of cell culture media from the recirculation pipe into the acoustic chamber. Arrow 4351 indicates the inlet flow path, and arrow 4355 indicates the outlet flow path. These two passageways are particularly visible in FIG. 44. Put another way, the inlet flow path travels through a different passage than the outlet flow path. This arrangement creates a secondary recirculating flow that is tangential to the acoustic interface, and allows for constant recirculation of cells beneath this acoustic interface, traveling in the same net direction as the recirculation flow path 4356.

The flow geometry of the inflow passageway 4380 and the outflow passageway 4390 can affect the flow profile through the acoustic chamber. FIG. 46A and FIG. 46C are front views showing two different internal structures that result in different flow profiles. In these two figures, the inlet port 4310 is on the right, and the outlet port 4330 is on the left.

Considering FIG. 46A and FIG. 46B first, the acoustic chamber 4350 is shown, with the ultrasonic transducer 4360 shown in dashed line. The acoustic chamber 4350 includes a first side wall 4362 and a second side wall 4364. The inflow passageway 4380 also has a first wall 4381 and a second wall 4382, with the first wall 4381 extending beyond the first side wall 4362, or closer to the inlet port 4310. The bottom cross-sectional area of the inflow passageway (adjacent the recirculation pipe 4340) is indicated by reference numeral 4384, and the top cross-sectional area of the inflow passageway (adjacent the acoustic chamber 4350) is indicated by reference numeral 4383. In embodiments, the top cross-sectional area of the inflow passageway is greater than the bottom cross-sectional area of the inflow passageway.

The outflow passageway 4390 also has a first wall 4391 and a second wall 4392. The first wall 4391 and the second wall 4392 taper towards each other from the acoustic chamber 4350 to the recirculation pipe 4340. The bottom cross-sectional area of the outflow passageway (adjacent the recirculation pipe 4340) is indicated by reference numeral 4394, and the top cross-sectional area of the outflow passageway (adjacent the acoustic chamber 4350) is indicated by reference numeral 4393. In embodiments, the top cross-sectional area of the outflow passageway is greater than the bottom cross-sectional area of the outflow passageway.

It is noted that the top cross-sectional area 4393 of the outflow passageway is greater than the top cross-sectional area 4383 of the outflow passageway. The bottom cross-sectional area 4394 of the outflow passageway is also less than the bottom cross-sectional area 4384 of the outflow passageway. Desirably, this arrangement promotes the direction for cells and other larger materials to enter the acoustic chamber 4350, and maximizes their opportunity to exit the acoustic chamber in the same direction as the main recirculation flow.

Now considering FIG. 46C and FIG. 46D, the first wall 4381 of the inflow passageway 4380 is essentially in-line with the first side wall 4362. The second wall 4382 is vertical like the first side wall, then widens at the top. The top cross-sectional area 4383 of the inflow passageway is greater than the bottom cross-sectional area 4384 of the inflow passageway. The first wall 4391 of the outflow passageway 4390 tapers downwards, and then becomes vertical. The second wall 4392 tapers inwards from the second side wall 4364 to the recirculation pipe 4340. Again, the top cross-sectional area 4393 of the outflow passageway is greater than the bottom cross-sectional area 4394 of the outflow passageway. In FIG. 46C, the top cross-sectional area 4393 of the outflow passageway is still greater than the top cross-sectional area 4383 of the outflow passageway. The bottom cross-sectional area 4394 of the outflow passageway can be about equal to or less than the bottom cross-sectional area 4384 of the outflow passageway.

Figure 47:
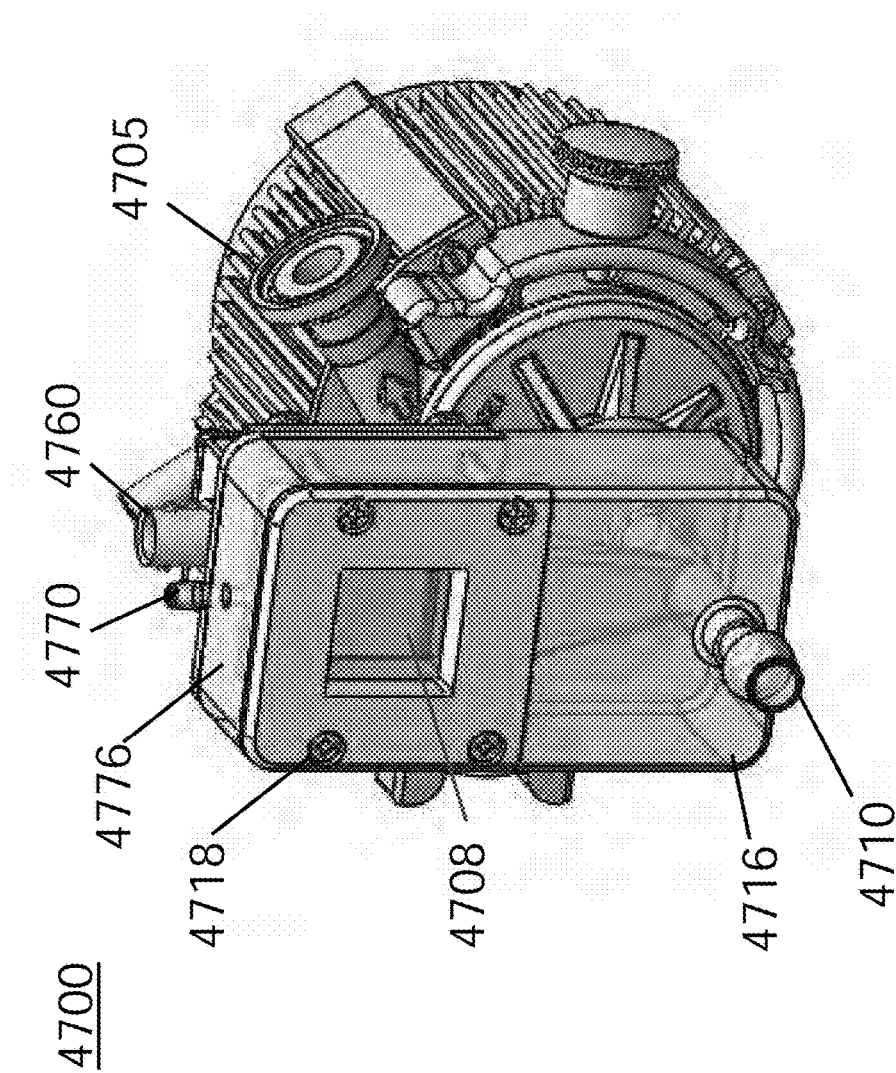
FIG. 47 is a perspective view of a sixth exemplary embodiment of an acoustic perfusion device of the present disclosure. This embodiment includes a direct recirculation flow path between the inlet port and the outlet port. A single passageway joins the recirculation flow path to the acoustic chamber, and acts as both the inflow passageway and the outflow passageway.
Figure 49:
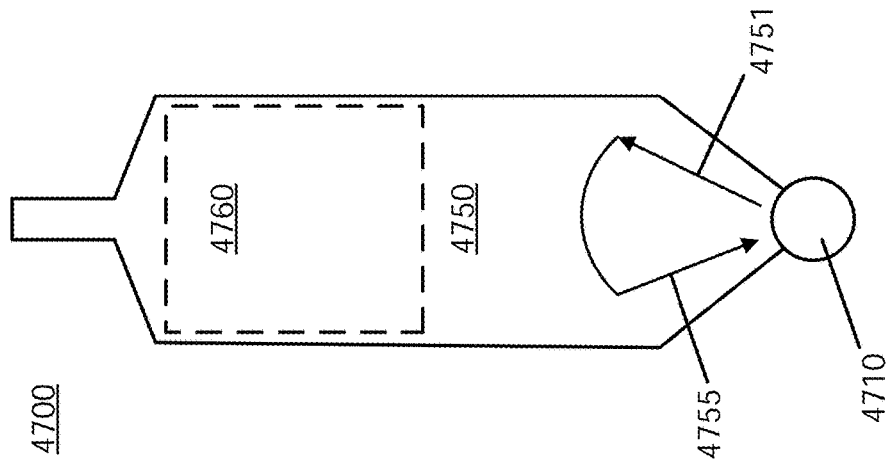
FIG. 49 is a diagrammatic front view of the device of FIG. 43, showing the internal structure.
Figure 48:
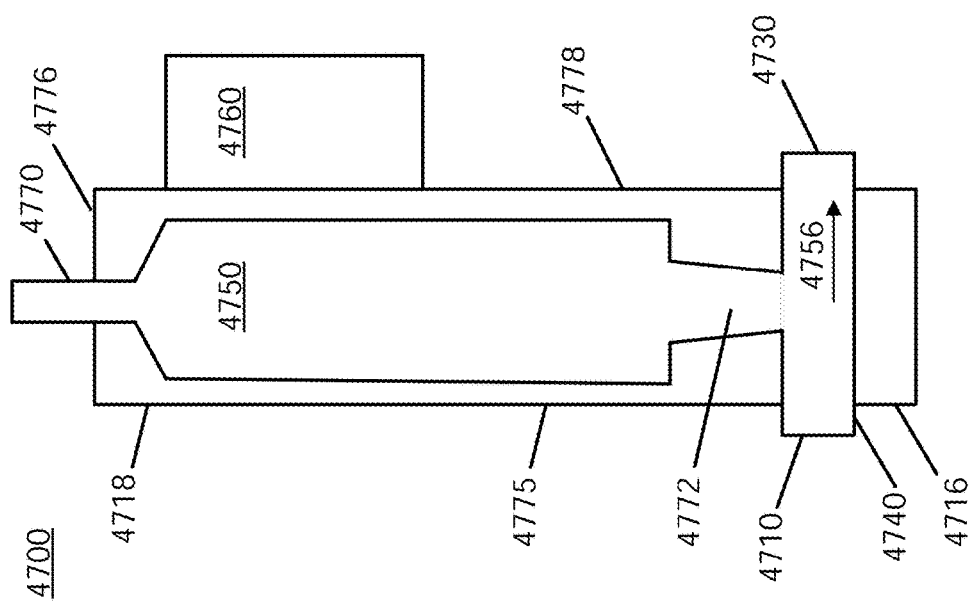
FIG. 48 is a diagrammatic side view of the device of FIG. 43.

FIGS. 47-49 are views of yet another exemplary embodiment of an acoustic perfusion device. FIG. 47 is a perspective view, FIG. 48 is a side view. FIG. 49 is a front schematic view of the interior layout of the device.

Referring now to FIGS. 47-49, in this device 4700, the inlet port 4710 and the outlet port 4730 are both located at the bottom end 4716 of the device, and the collection port 4770 is located at the top end 4718 of the device. The inlet port 4710 is located on the front wall 4775 of the device, and the outlet port 4730 is located on the rear wall 4778 of the device. In FIG. 47, the outlet port 4730 is attached to a pump 4705, which creates flow through the device 4700. A viewing window 4708 is present on the front wall 4775 of the device. The front wall 4775, top wall 4776, and rear wall 4778 are part of the housing 4706 that surrounds the interior of the device.

Referring now to FIG. 47 and FIG. 48, the ultrasonic transducer 4760 is located on the rear wall 4778 at the top end 4718 of the device. The viewing window 4708 acts as a reflector to generate the multi-dimensional acoustic standing waves.

Again, a recirculation pipe 4740 connects the inlet port 4710 directly to the outlet port 4730, and forms a recirculation flow path (arrow 4756) through which cell culture media containing cells and other materials can be continuously recirculated through the perfusion device without entering the acoustic chamber 4750. The recirculation pipe 4740 and the recirculation flow path 4756 are located below the acoustic chamber 4750.

This embodiment differs from that of FIG. 43 in that a single passageway 4772 connects the acoustic chamber 4750 to the recirculation pipe 4740, rather than the two separate passageways (4380, 4390) of FIG. 43. Referring now to FIG. 49, arrow 4751 indicates the inlet flow path, and arrow 4755 indicates the outlet flow path, both traveling through the single passageway. This flow still results in a secondary recirculating flow that is tangential to the acoustic interface, and allows for constant recirculation of cells beneath this acoustic interface, traveling in the same net direction as the recirculation flow path 4756.

Figure 11:
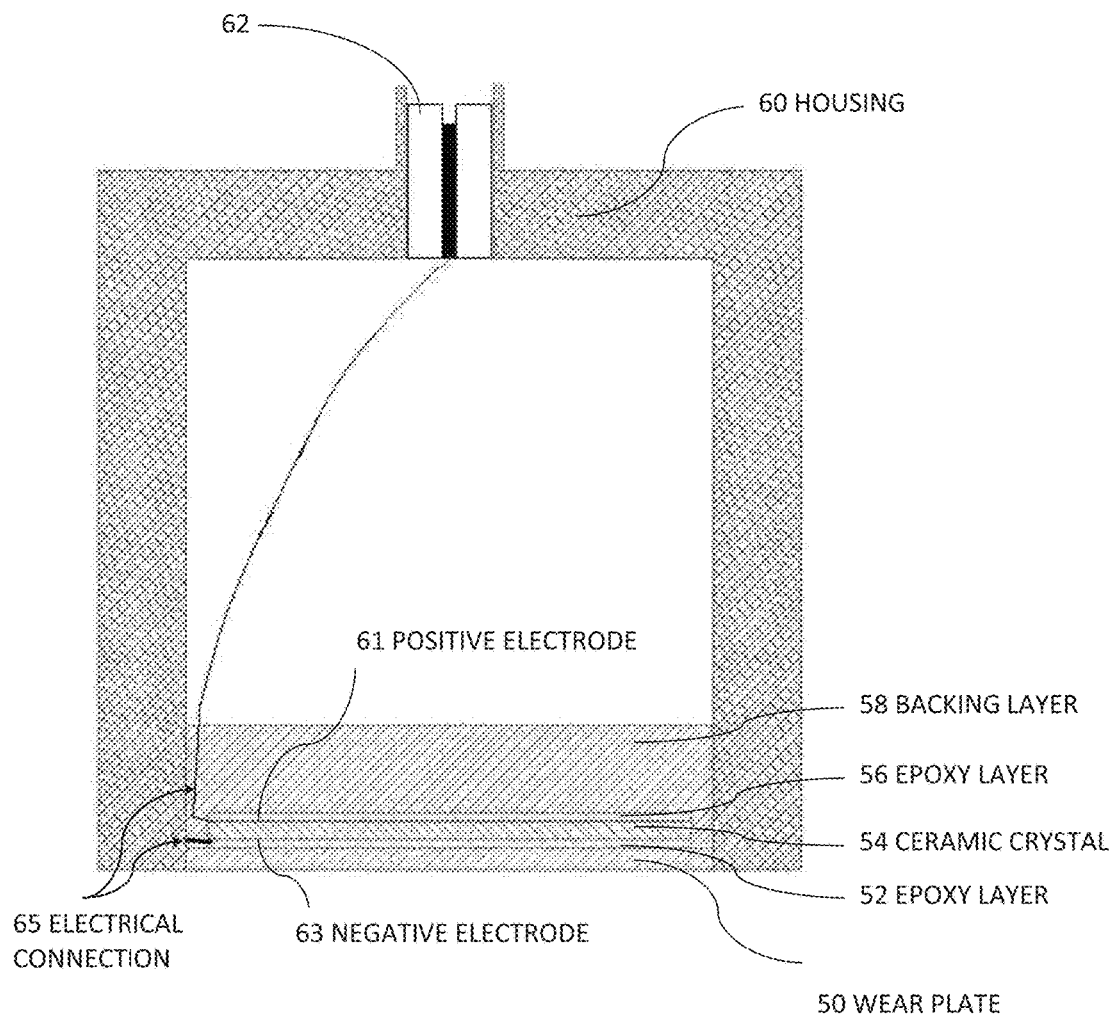
FIG. 11 is a cross-sectional diagram of a conventional ultrasonic transducer.

It may be helpful now to describe the ultrasonic transducer(s) used in the acoustic filtering device in more detail. FIG. 11 is a cross-sectional diagram of a conventional ultrasonic transducer. This transducer has a wear plate 50 at a bottom end, epoxy layer 52, ceramic piezoelectric element 54 (made of, e.g. Lead Zirconate Titanate (PZT)), an epoxy layer 56, and a backing layer 58. On either side of the ceramic piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. The housing is used as the ground electrode. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation of particular vibrational eigen-modes of the piezoelectric element. Wear plates are usually designed as impedance transformers to better match the characteristic impedance of the medium into which the transducer radiates.

Figure 12:
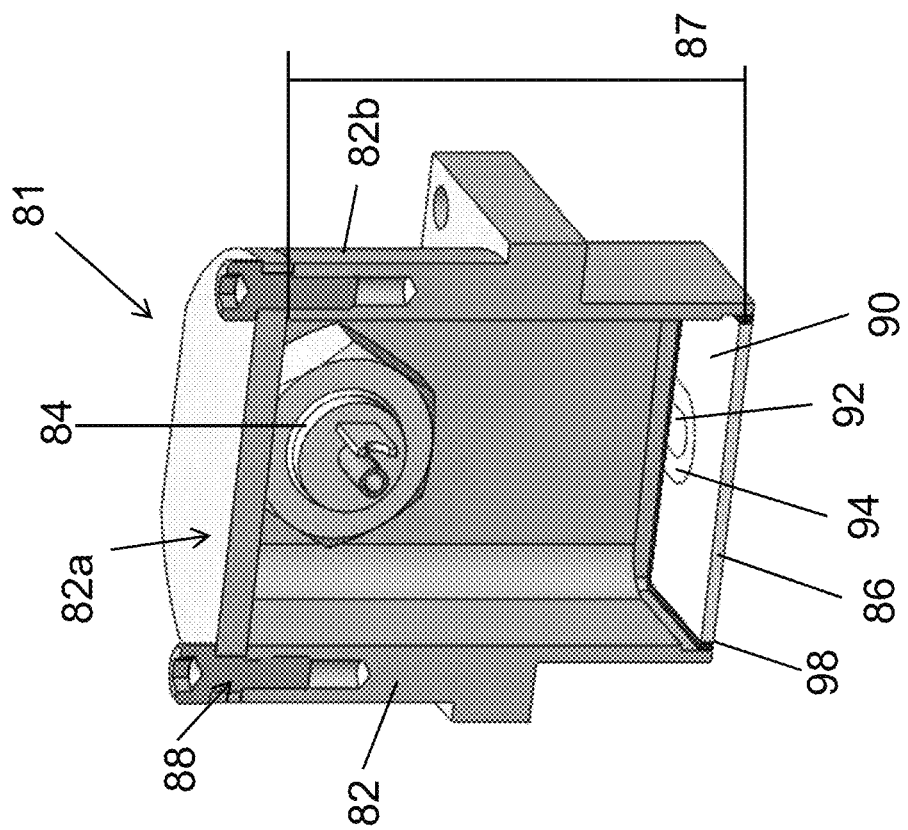
FIG. 12 is a cross-sectional diagram of an ultrasonic transducer of the present disclosure. An air gap is present within the transducer, and no backing layer or wear plate are present.

FIG. 12 is a cross-sectional view of an ultrasonic transducer 81 according to an example of the present disclosure, which is used in the acoustic filtering device of the present disclosure. Transducer 81 is shaped as a disc or a plate, and has an aluminum housing 82. The aluminum housing has a top end and a bottom end. The transducer housing may also be composed of plastics, such as medical grade HDPE or other metals. The piezoelectric element is a mass of perovskite ceramic, each consisting of a small, tetravalent metal ion, usually titanium or zirconium, in a lattice of larger, divalent metal ions, usually lead or barium, and $O^{2-}$ ions. As an example, a PZT (lead zirconate titanate) piezoelectric element 86 defines the bottom end of the transducer, and is exposed from the exterior of the bottom end of the housing. The piezoelectric element is supported on its perimeter by a small elastic layer 98, e.g. epoxy, silicone or similar material, located between the piezoelectric element and the housing. Put another way, no wear plate or backing material is present. However, in some embodiments, there is a layer of plastic or other material separating the piezoelectric element from the fluid in which the acoustic standing wave is being generated. The piezoelectric element/crystal has an exterior surface (which is exposed) and an interior surface as well. In particular embodiments, the piezoelectric element/crystal is an irregular polygon, and in further embodiments is an asymmetrical irregular polygon.

Figure 13:
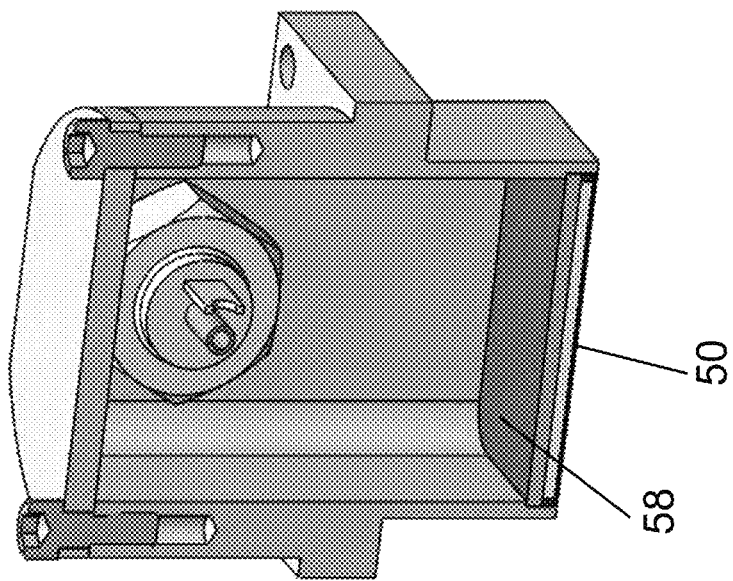
FIG. 13 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT piezoelectric element 86 is connected to a positive electrode 90 and a negative electrode 92, which are separated by an insulating material 94. The electrodes can be made from any conductive material, such as silver or nickel. Electrical power is provided to the PZT piezoelectric element 86 through the electrodes on the piezoelectric element. Note that the piezoelectric element 86 has no backing layer or epoxy layer. Put another way, there is an interior volume or an air gap 87 in the transducer between aluminum top plate 82a and the piezoelectric element 86 (i.e. the housing is empty). A minimal backing 58 (on the interior surface) and/or wear plate 50 (on the exterior surface) may be provided in some embodiments, as seen in FIG. 13.

The transducer design can affect performance of the system. A typical transducer is a layered structure with the ceramic piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes with a high Q-factor, or in a combination of several eigenmodes. The vibrating ceramic piezoelectric element/disk is directly exposed to the fluid flowing through the fluid cell.

Removing the backing (e.g. making the piezoelectric element air backed) also permits the ceramic piezoelectric element to vibrate at higher order modes of vibration with little damping (e.g. higher order modal displacement). In a transducer having a piezoelectric element with a backing, the piezoelectric element vibrates with a more uniform displacement, like a piston. Removing the backing allows the piezoelectric element to vibrate in a non-uniform displacement mode. The higher order the mode shape of the piezoelectric element, the more nodal lines the piezoelectric element has. The higher order modal displacement of the piezoelectric element creates more trapping lines, although the correlation of trapping line to node is not necessarily one to one, and driving the piezoelectric element at a higher frequency will not necessarily produce more trapping lines.

It is contemplated that, in some embodiments of the acoustic filtering device of the present disclosure, the piezoelectric element may have a backing that minimally affects the Q-factor of the piezoelectric element (e.g. less than 5%). The backing may be made of a substantially acoustically transparent material such as balsa wood, foam, or cork which allows the piezoelectric element to vibrate in a higher order mode shape and maintains a high Q-factor while still providing some mechanical support for the piezoelectric element. The backing layer may be a solid, or may be a lattice having holes through the layer, such that the lattice follows the nodes of the vibrating piezoelectric element in a particular higher order vibration mode, providing support at node locations while allowing the rest of the piezoelectric element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments of the transducer(s) may have wear plates or a wear surface to prevent the PZT, which contains lead, from contacting the host fluid. This additional layer may be desirable in, for example, biological applications such as separating blood, biopharmaceutical perfusion, or fed-batch filtration of mammalian cells. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface. Thin films, such as a PEEK film, can also be used as a cover of the transducer surface exposed to the fluid with the advantage of being a biocompatible material. In one embodiment, the PEEK film is adhered to the face of the piezomaterial using pressure sensitive adhesive (PSA). Other films can be used as well.

In some embodiments, for applications such as oil/water emulsion splitting and others such as perfusion, the ultrasonic transducer has a nominal 2 MHz resonance frequency. Each transducer can consume about 28 W of power for droplet trapping at a flow rate of 3 GPM. This power consumption translates to an energy cost of 0.25 kW hr/m$^3$. This cost is an indication of the very low cost of energy of this technology. Desirably, each transducer is powered and controlled by its own amplifier. In other embodiments, the ultrasonic transducer uses a square piezoelectric element, for example with 1"×1" dimensions. Alternatively, the ultrasonic transducer can use a rectangular piezoelectric element, for example with 1"×2.5" dimensions. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired multi-dimensional acoustic standing wave patterns.

In some examples, the size, shape, and thickness of the transducer can determine the transducer displacement at different frequencies of excitation. Transducer displacement with different frequencies may affect separation efficiency. Typically, the transducer is operated at frequencies near the thickness resonance frequency (half wavelength). Gradients in transducer displacement typically result in more trapping locations for the cells/biomolecules. Higher order modal displacements can generate three-dimensional acoustic standing waves with strong gradients in the acoustic field in all directions, thereby creating strong acoustic radiation forces in all directions, which forces may, for example, be equal in magnitude, leading to multiple trapping lines, where the number of trapping lines correlate with the particular mode shape of the transducer.

To investigate the effect of the transducer displacement profile on acoustic trapping force and separation efficiencies, an experiment was repeated ten times using a 1"×1" square transducer, with all conditions identical except for the excitation frequency. Ten consecutive acoustic resonance frequencies, indicated by circled numbers 1-9 and letter A on FIG. 14, were used as excitation frequencies. The conditions were experiment duration of 30 min, a 1000 ppm oil concentration of approximately 5-micron SAE-30 oil droplets, a flow rate of 500 ml/min, and an applied power of 20W. Oil droplets were used because oil is less dense than water, and can be separated from water using acoustophoresis.

Figure 14:
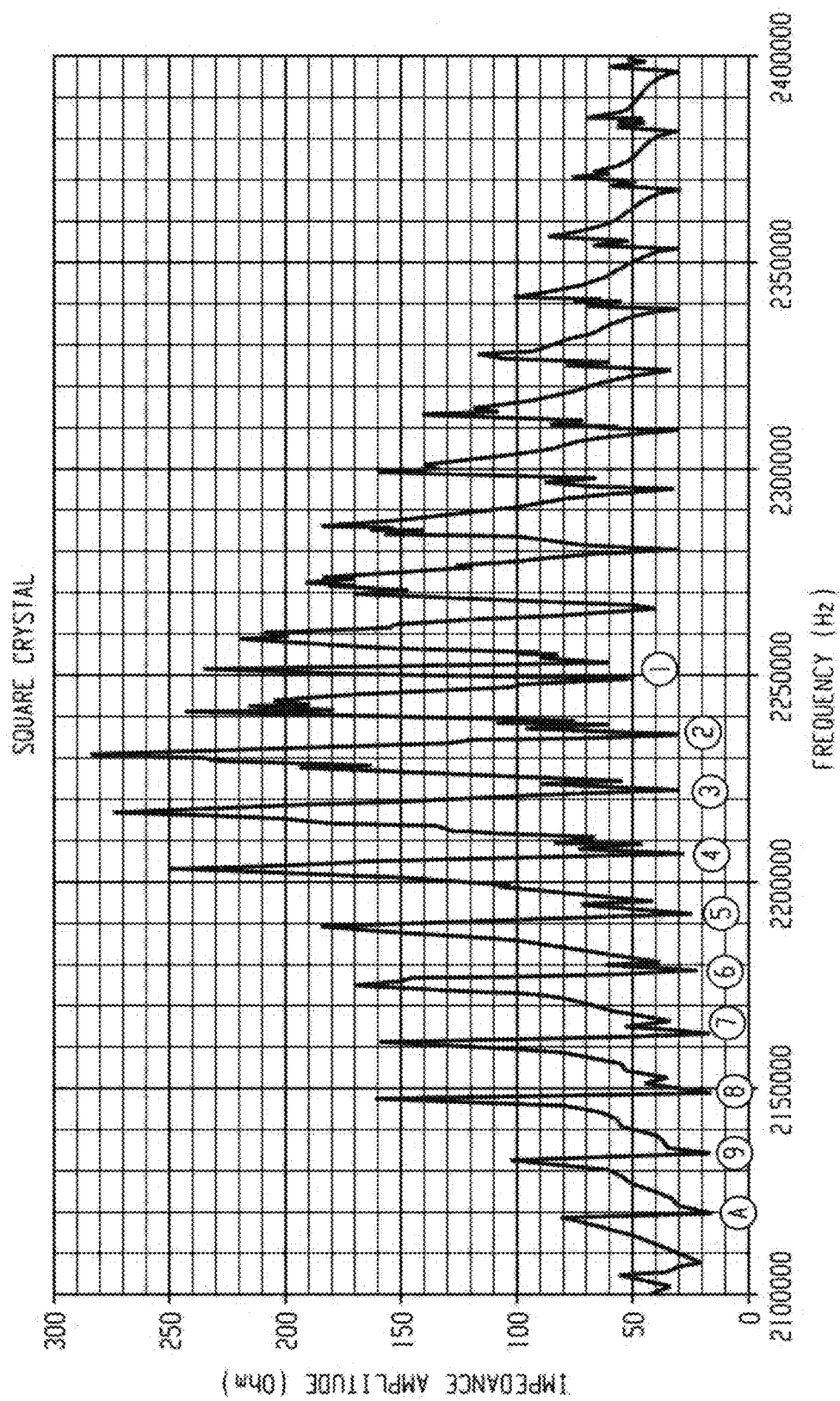
FIG. 14 is a graph of electrical impedance amplitude versus frequency for a square transducer driven at different frequencies.

FIG. 14 shows the measured electrical impedance amplitude of a square transducer as a function of frequency in the vicinity of the 2.2 MHz transducer resonance. The minima in the transducer electrical impedance correspond to acoustic resonances of the water column and represent potential frequencies for operation. Additional resonances exist at other frequencies where multi-dimensional standing waves are excited. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes may not be uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

Figure 15:
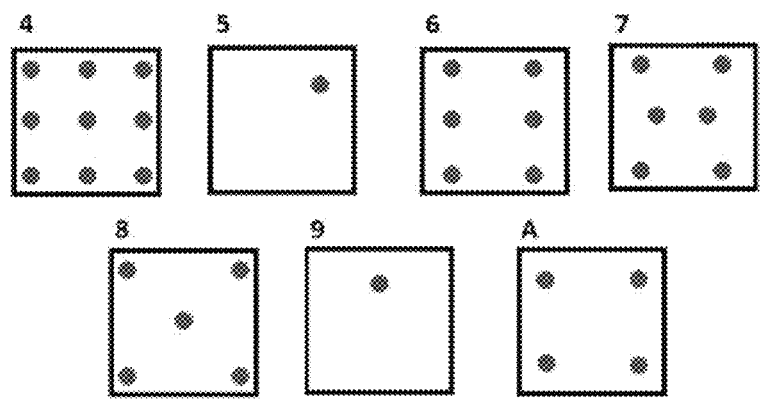
FIG. 15 illustrates the trapping line configurations for seven of the resonance frequencies (minima of electrical impedance amplitudes) of FIG. 14 from the direction orthogonal to fluid flow.

As the oil-water emulsion passed by the transducer, the trapping lines of oil droplets were observed and characterized. The characterization involved the observation and pattern of the number of trapping lines across the fluid channel, as shown in FIG. 15, for seven of the ten resonance frequencies identified in FIG. 14. Different displacement profiles of the transducer can produce different (more) trapping lines in the standing waves, with more gradients in displacement profile generally creating higher trapping forces and more trapping lines. Different displacement profiles of the transducer can produce different (more) trapping lines in the standing waves, with more gradients in displacement profile generally creating higher trapping forces and more trapping lines. It is noted that although the different trapping line profiles shown in FIG. 15 were obtained at the frequencies shown in FIG. 14, these trapping line profiles can also be obtained at different frequencies. FIG. 15 shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in lateral directions across the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 15.

Figure 16:
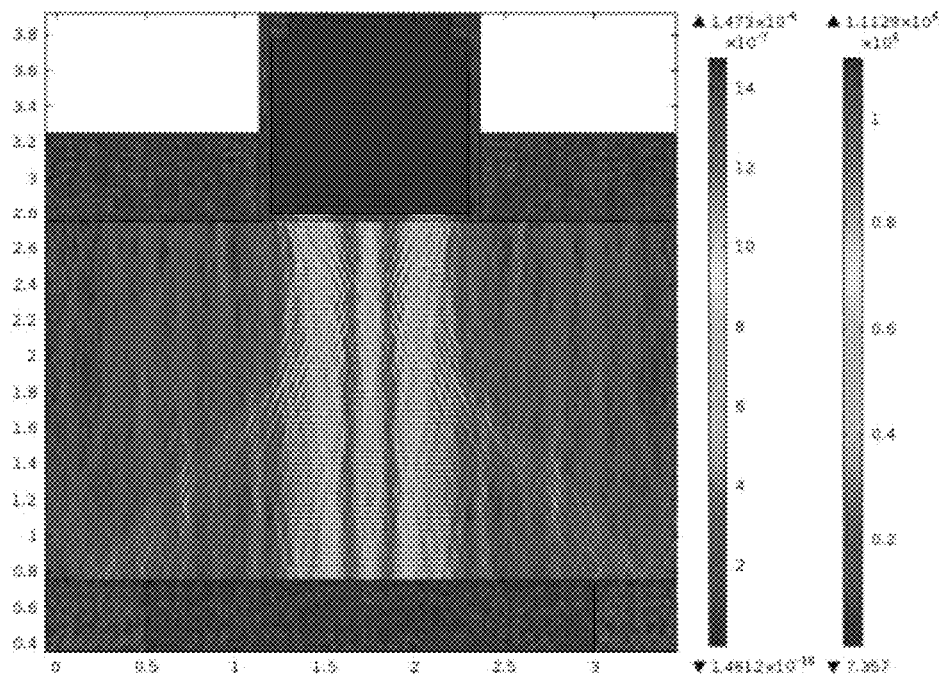
FIG. 16 is a computer simulation of the acoustic pressure amplitude (right-hand scale in Pa) and transducer out of plane displacement (left-hand scale in meters). The text at the top of the left-hand scale reads "×$10^{-7}$". The text at the top of the left-hand scale by the upward-pointing triangle reads "1.473×$10^{-6}$". The text at the bottom of the left-hand scale by the downward-pointing triangle reads "1.4612×$10^{-10}$". The text at the top of the right-hand scale reads "×$10^{6}$". The text at the top of the right-hand scale by the upward-pointing triangle reads "1.1129×$10^{6}$". The text at the bottom of the right-hand scale by the downward-pointing triangle reads "7.357". The triangles show the maximum and minimum values depicted in this figure for the given scale. The horizontal axis is the location within the chamber along the X-axis, in inches, and the vertical axis is the location within the chamber along the Y-axis, in inches.

FIG. 16 is a numerical model showing a pressure field that matches the 9 trapping line pattern. The numerical model is a two-dimensional model; and therefore three trapping lines are observed. Two more sets of three trapping lines exist in the third dimension perpendicular to the plane of the page.

The lateral force of the acoustic radiation force generated by the transducer can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage. The transducer is typically a thin piezoelectric plate, with electric field in the z-axis and primary displacement in the z-axis. The transducer is typically coupled on one side by air (i.e., the air gap within the transducer) and on the other side by the fluid mixture of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Figure 17:
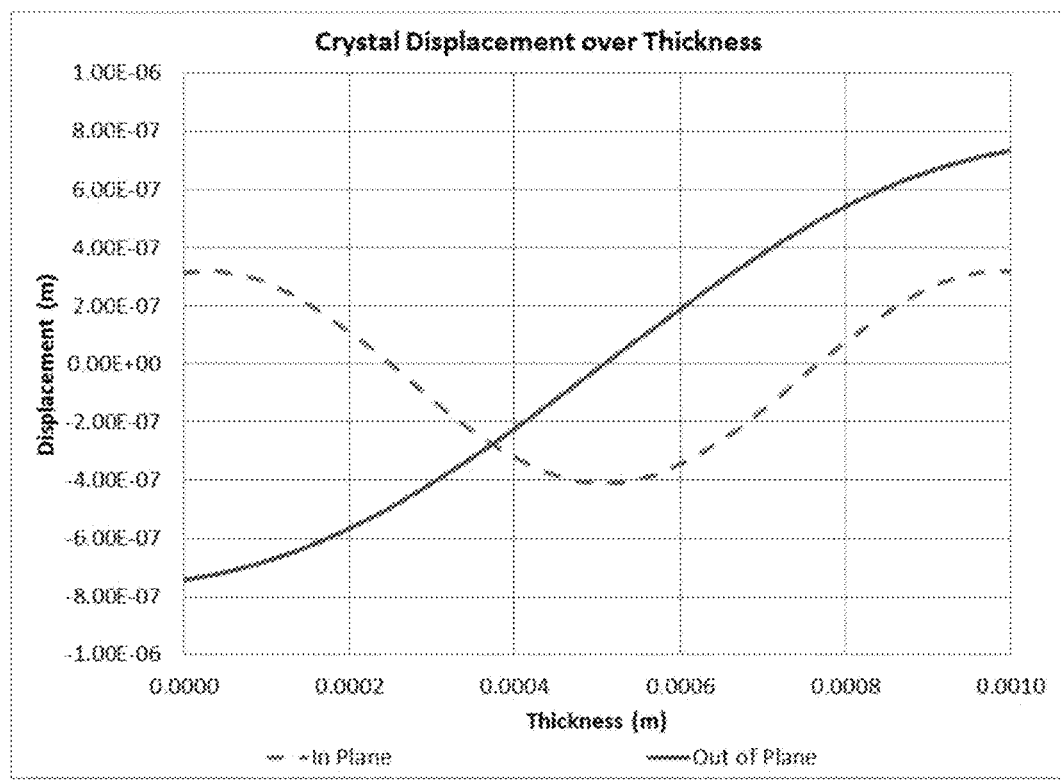
FIG. 17 shows the In-Plane and Out-of-Plane displacement of a crystal where composite waves are present.

FIG. 17 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. In general, a (m,n) mode is a displacement mode of the transducer in which there are m undulations in transducer displacement in the width direction and n undulations in the length direction, and with the thickness variation as described in FIG. 17. The maximum number of m and n is a function of the dimension of the crystal and the frequency of excitation. Additional three-dimensional modes exist that are not of the form (m,n).

The transducers are driven so that the piezoelectric element vibrates in higher order modes of the general formula (m, n), where m and n are independently 1 or greater. Generally, the transducers will vibrate in higher order modes than (2,2). Higher order modes will produce more nodes and antinodes, result in three-dimensional standing waves in the water layer, characterized by strong gradients in the acoustic field in all directions, not only in the direction of the standing waves, but also in the lateral directions. As a consequence, the acoustic gradients result in stronger trapping forces in the lateral direction.

The transducer can be driven by a signal, such as a voltage signal, a current signal, a magnetic signal, an electromagnetic signal, a capacitive signal, or any other type of signal to which the transducer is responsive to create a multi-dimensional acoustic standing wave. In embodiments, the voltage signal driving the transducer can have a sinusoidal, square, sawtooth, pulsed, or triangle waveform; and have a frequency of 500 kHz to 10 MHz. The voltage signal can be driven with pulse width modulation, which produces any desired waveform. The voltage signal can also have amplitude or frequency modulation start/stop capability to eliminate streaming.

The transducers are used to create a pressure field that generates acoustic radiation forces of the same order of magnitude both orthogonal to the standing wave direction and in the standing wave direction. When the forces are roughly the same order of magnitude, particles of size 0.1 microns to 300 microns will be moved more effectively towards "trapping lines", so that the particles will not pass through the pressure field and continue to exit through the collection ports of the filtering device. Instead, the particles will remain within the acoustic chamber to be recycled back to the bioreactor.

In biological applications, it is contemplated that all of the parts of the system (i.e., the bioreactor, acoustic filtering device, tubing fluidly connecting the same, etc.) can be separated from each other and be disposable. Avoiding centrifuges and filters allows better separation of the CHO cells without lowering the viability of the cells. The transducers may also be driven to create rapid pressure changes to prevent or clear blockages due to agglomeration of CHO cells. The frequency of the transducers may also be varied to obtain optimal effectiveness for a given power.

The following examples are provided to illustrate the devices, components, and methods of the present disclosure. The examples are merely illustrative and are not intended to limit the disclosure to the materials, conditions, or process parameters set forth therein.

EXAMPLES

Example 1

Figure 18:
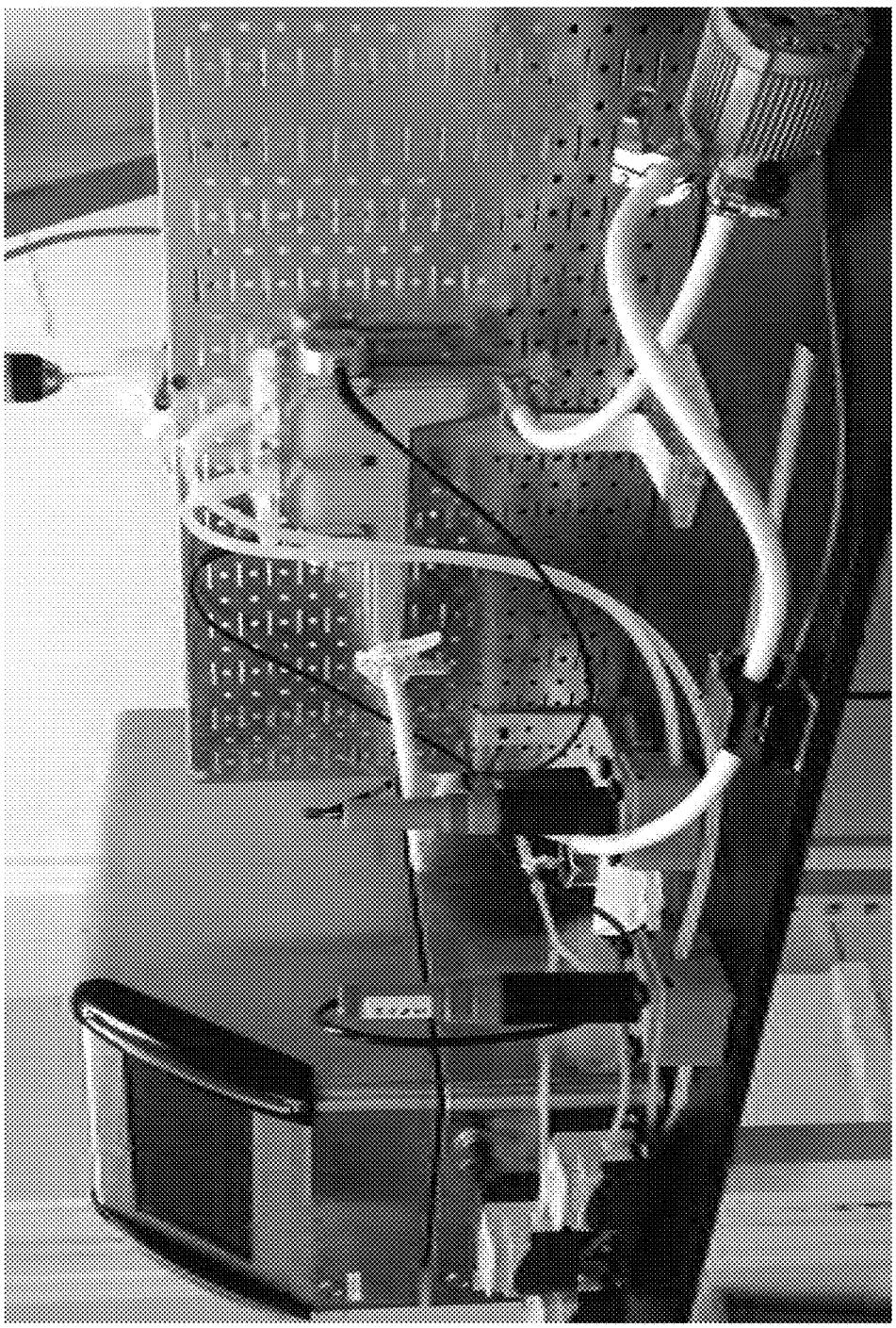
FIG. 18 is a view of a first acoustic perfusion device of the present disclosure fluidly connected to an associated bioreactor, showing a plurality of hoses fluidly connecting the various ports of the device to the associated bioreactor and an outflow pump fluidly connecting the outlet port of the device to the associated bioreactor.

FIG. 18 shows an experimental setup for an acoustic perfusion device as described in detail above. This acoustic perfusion device is very similar to that illustrated in FIG. 5, except the bottom wall is not curved, but rather runs horizontally from the first end and then angles directly to the outlet port. Tubes are connected to the inlet port, outlet port, and the two collection ports. A pump is also visibly fluidly connected to the outlet port.

Figure 19:
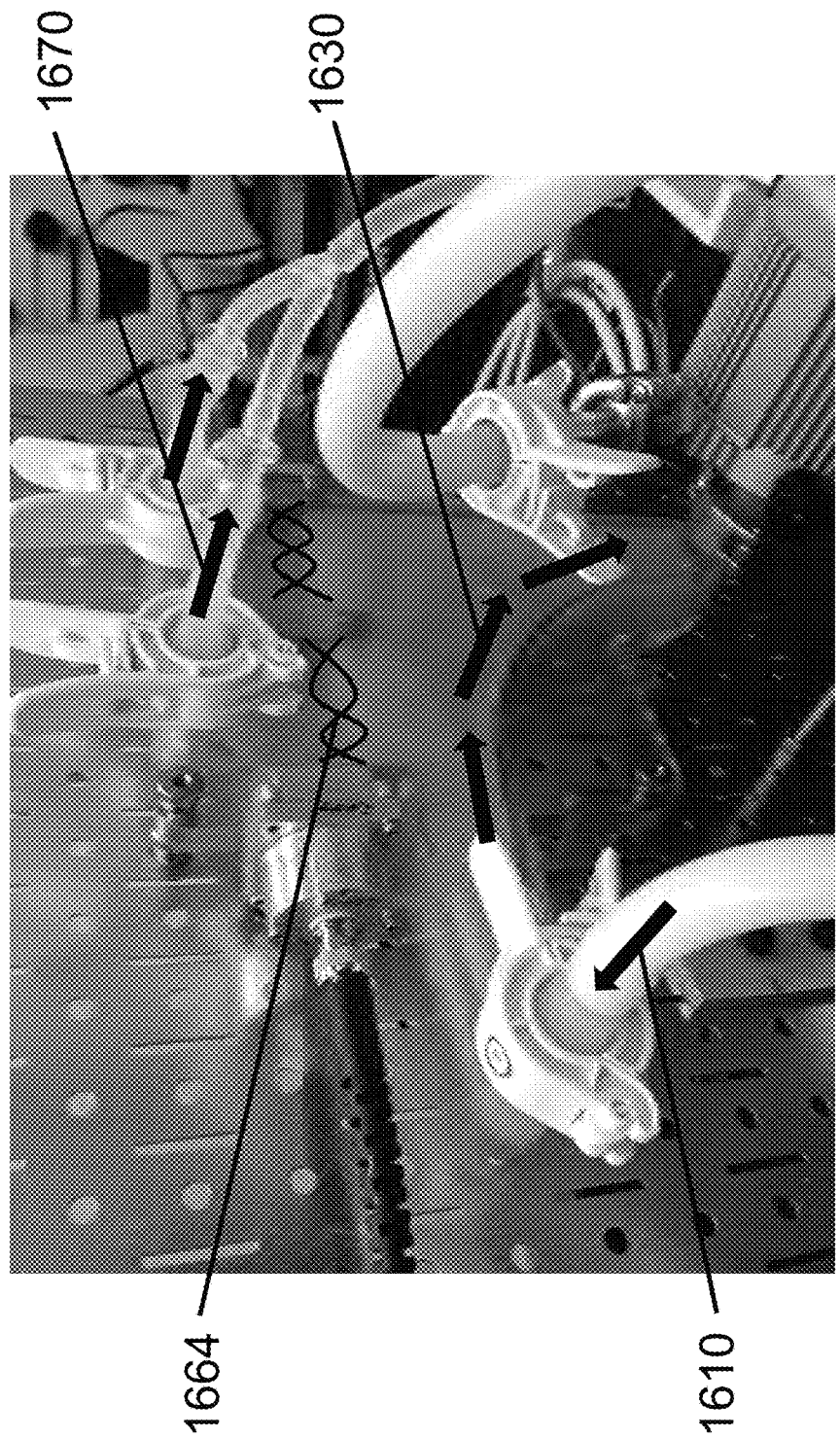
FIG. 19 is a view of another acoustic perfusion device of FIG. 5, showing a reflector in the acoustic chamber between first and second transducers. A fluid mixture is also present in the device and arrows are shown indicating the direction of flow in addition to waves indicating the acoustic field between the reflector and first and second transducers.

FIG. 19 is a picture of another acoustic perfusion device of the present disclosure, similar to the embodiment shown in FIG. 5, having two ultrasonic transducers and a concave bottom wall leading from the inlet port to the outlet port at the bottom end of the device. A cell containing fluid mixture is also present in the device. In this picture, acoustic standing waves are created in the collection zone between the reflector and first and second transducers as described above. The acoustic field generated thereby is indicated by waves and reference numeral 1664. The flow pattern of the fluid mixture through the device from the inlet port to the outlet port is shown with an arrow (reference numeral 1610) indicating the direction of fluid flow into the device and arrows (reference numeral 1630) indicating the direction of fluid flow through the device towards the outlet port. Finally, the general flow pattern of the desired product out of the device through the first and second collection ports is shown with arrows (reference numeral 1670) indicating the direction of flow.

Acoustophoretic separation has been tested using the acoustic perfusion device of FIG. 19 and the methods of separation of the present disclosure on different lines of Chinese hamster ovary (CHO) cells. FIGS. 20-28 show various test results varying different parameters and measuring different values using a Beckman Coulter Cell Viability Analyzer.

The perfusion flow rates with the acoustic filtering device were from about 2 mL/min to about 10 mL/min, or the flow rates were about 1 VVD to about 5 VVD for a 2.7 L working volume bioreactor. The VVD refers to the "vessel volume per day", or how many times the volume of the bioreactor vessel is cycled through the acoustic filtering device in one day. The perfusion flow rate (Qp) was collected through the perfusion ports. In contrast, the feed flow rates (Qf) were from about 40 mL/min to about 200 mL/min.

The feed solution had a starting CHO cell density of $50 \cdot 10^6$ cells/mL. The reactor size was 2.7 L and the feed volume of the host fluid was 1.5 L. In total, a series of seven tests (T1-T7) were performed to study the effect of varying the VVD and flow split in a 2.7 L volume reactor. The parameters for the tests are shown in Table 1 below.

TABLE 1

| System results for a 2.7 L reactor and feed volume of 1.5 L | | | | | |
|---|---|---|---|---|---|
| | Flow Split | | Qp | | |
| | (Qp/Qf) | 1 VVD | 1.5 VVD | 2 VVD | 5.2 VVD |
| Qf | 5.0% | T1 | T2 | T3 | T7 |
| | 2.5% | T4 | T5 | T6 | |

Figure 20:
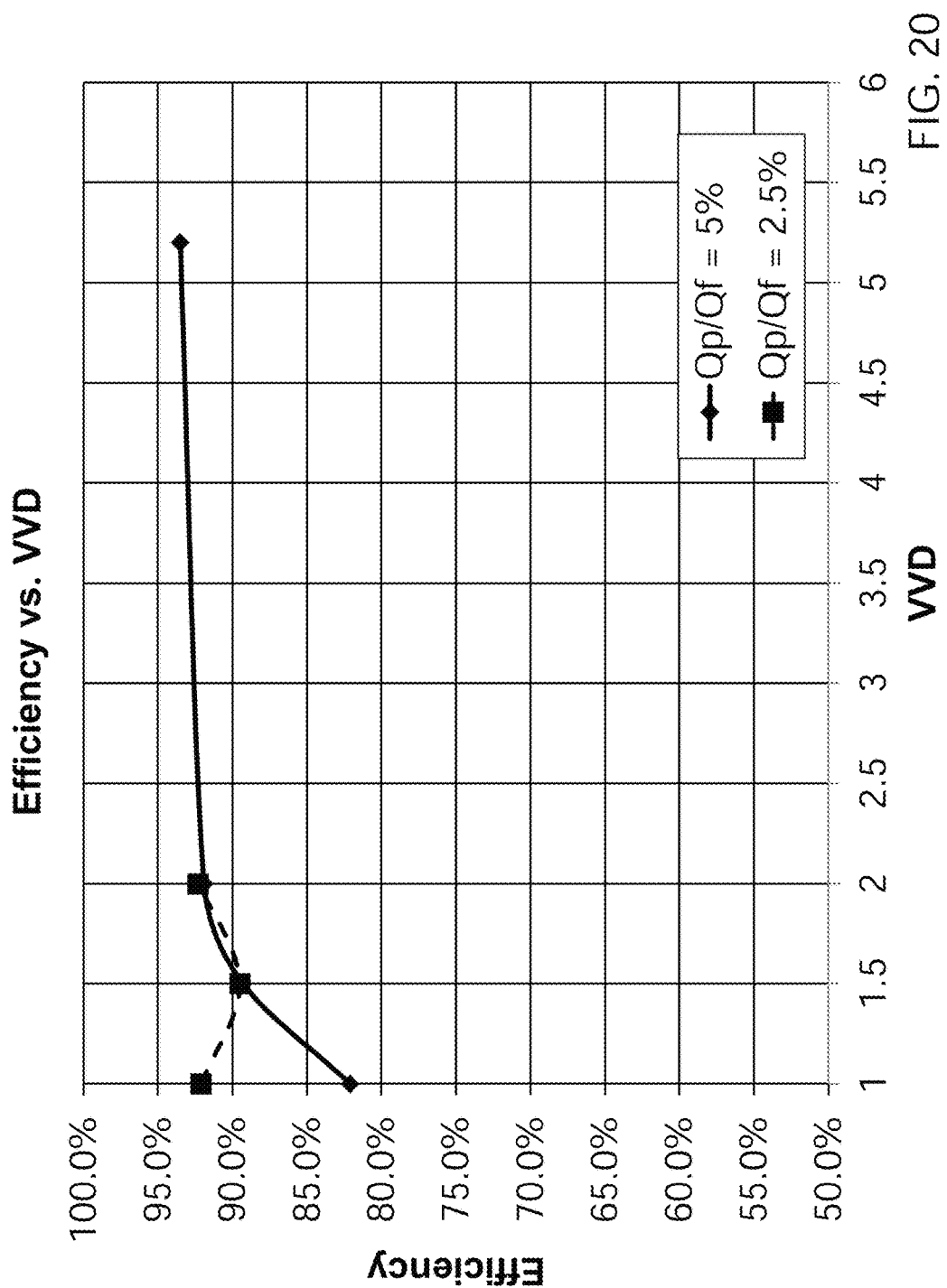
FIG. 20 is a graph showing the efficiency of removing cells from a fluid mixture for one experiment at two different perfusate/feed rates.

The results included a cell clarification efficiency between 89-93% at a DC voltage of 45V, regardless of the flow rate as shown in FIG. 20. It is noted that the DC voltage for T1 was fixed at 60V, whereas for tests T2-T7 the DC voltage was reduced to a fixed amount of 45V. The transducer voltage amplitude is estimated to be about half of these values.

Figure 21:
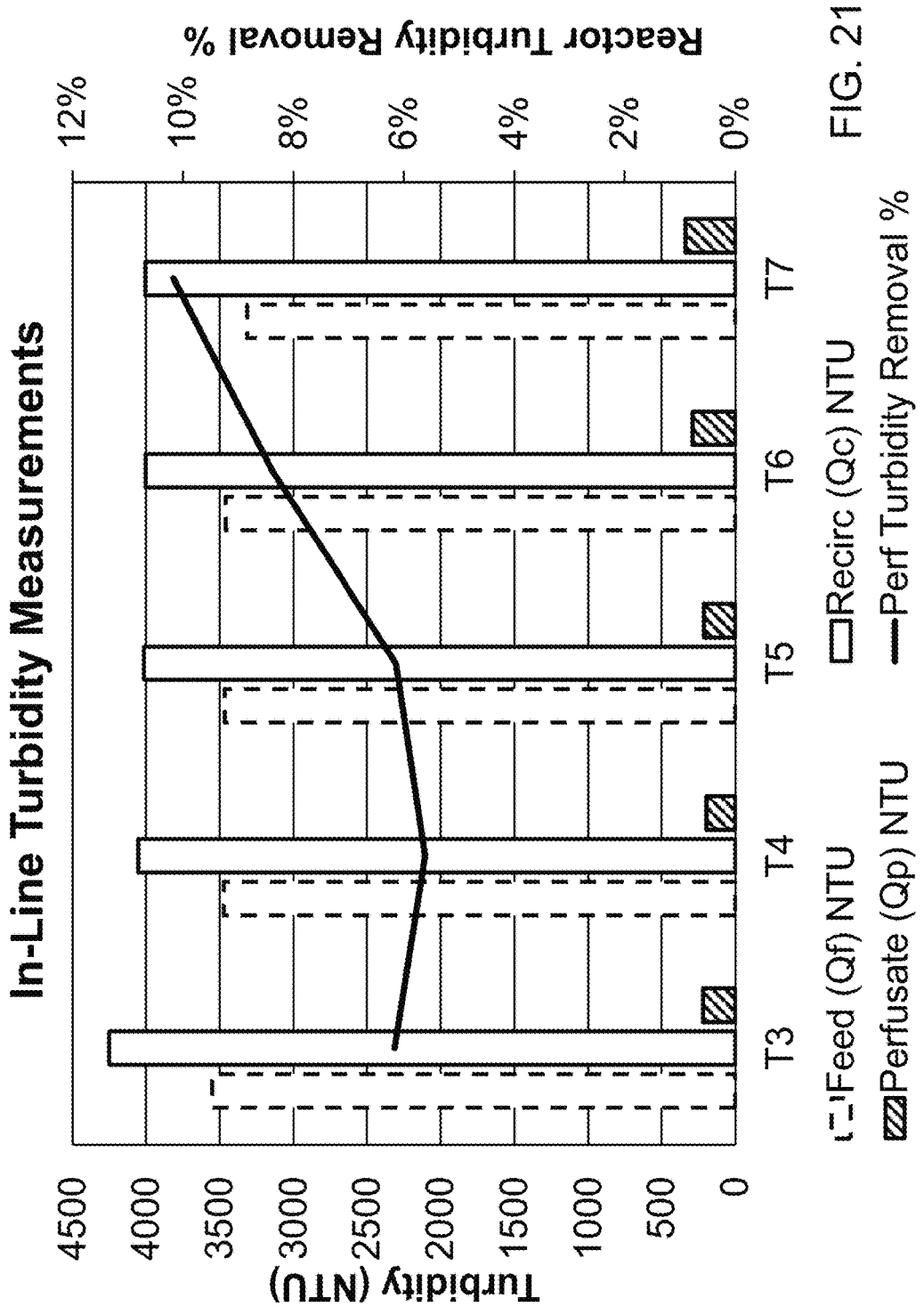
FIG. 21 is a graph showing the harvest flow (also referred to as the perfusate) turbidity reduction for an experiment

The results further included a perfusate turbidity reduction of 90-94% compared to the feed, as shown in FIG. 21. This figure shows the turbidity of the feed, the recirculated fluid (Qc), and the perfusate (Qp). The feed entered the inlet port, the recirculated fluid exited the outlet port and was recirculated, and the perfusate exited the perfusion port of the acoustic filtering device. It is noted that the turbidity measurements for tests T1 and T2 resulted in a hardware error, and their results are not displayed. The results of tests T3-T7 are displayed, which equated to a 6-10% turbidity in the perfusion stream relative to the feed stream, regardless of flow rate.

Figure 22:
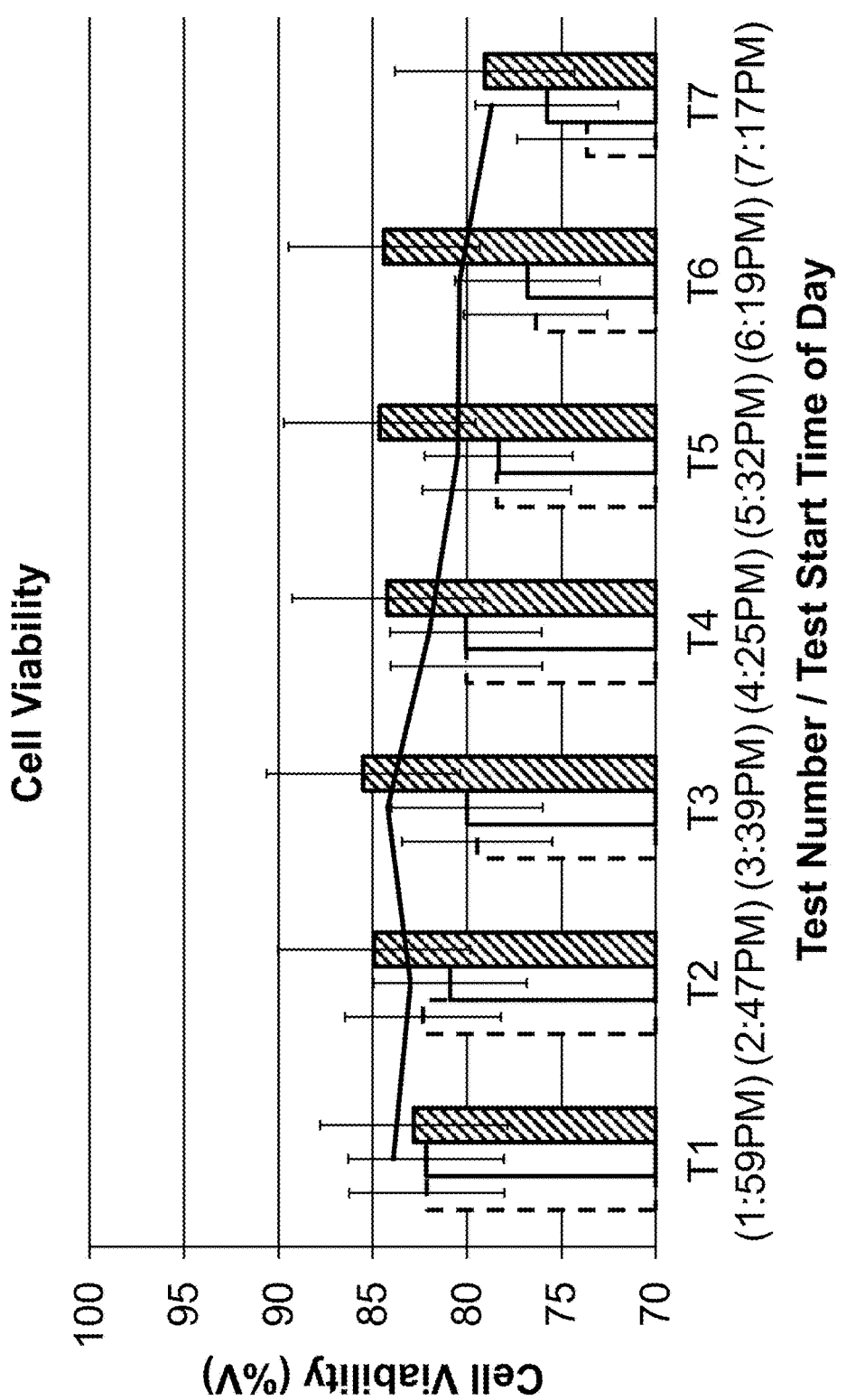
FIG. 22 is a graph showing the cell viability for varied flow rates for the experiment conducted for the graphs of FIGS. 20-21.

FIG. 22 was produced by a Beckman Coulter Cell Viability Analyzer and revealed a cell viability for each flow rate that was within the error of instrument (i.e., ±6%), with the control ranging from 79-84% over all tests.

Further testing was performed using a solution designated "CHO Line A". The solution had a starting cell density of $50 \cdot 10^6$ cells/mL, a turbidity of 2,400 NTU, and cell viability of roughly 80%. The solution was separated using a device of the present disclosure in a system having a reactor size of 2.7 L. The volume of the feed fluid was between 1.5 L and 2.0 L. The perfused flow rates were from 2 mL/min to 10 mL/min, or from 1 to 5 VVD. A series of six tests were performed to study the effect of varying the VVD and flow split on acoustic filtration performance for the 2.7 L volume reactor. The parameters for the tests are shown in Table 2 below.

TABLE 2

| System results for a 2.7 L reactor and feed volume from 1.5 L-2.0 L | | | | | |
|---|---|---|---|---|---|
| T1 | | T2 | | T3 | |
| VVD | 1.5 | VVD | 2 | VVD | 1 |
| Flow Split | 5.00% | Flow Split | 5.00% | Flow Split | 2.50% |
| Perfused Flow (ml/min) | 2.8 | Perfused Flow (ml/min) | 3.8 | Perfused Flow (ml/min) | 1.9 |
| Feed Flow (ml/min) | 56 | Feed Flow (ml/min) | 75 | Feed Flow (ml/min) | 75 |
| T4 | | T5 | | T6 | |
| VVD | 1.5 | VVD | 2 | VVD | 5.2 |
| Flow Split | 2.50% | Flow Split | 2.50% | Flow Split | 5.00% |
| Perfused Flow (ml/min) | 2.8 | Perfused Flow (ml/min) | 3.8 | Perfused Flow (ml/min) | 10 |
| Feed Flow (ml/min) | 112.5 | Feed Flow (ml/min) | 150 | Feed Flow (ml/min) | 194.2 |

Figure 23:
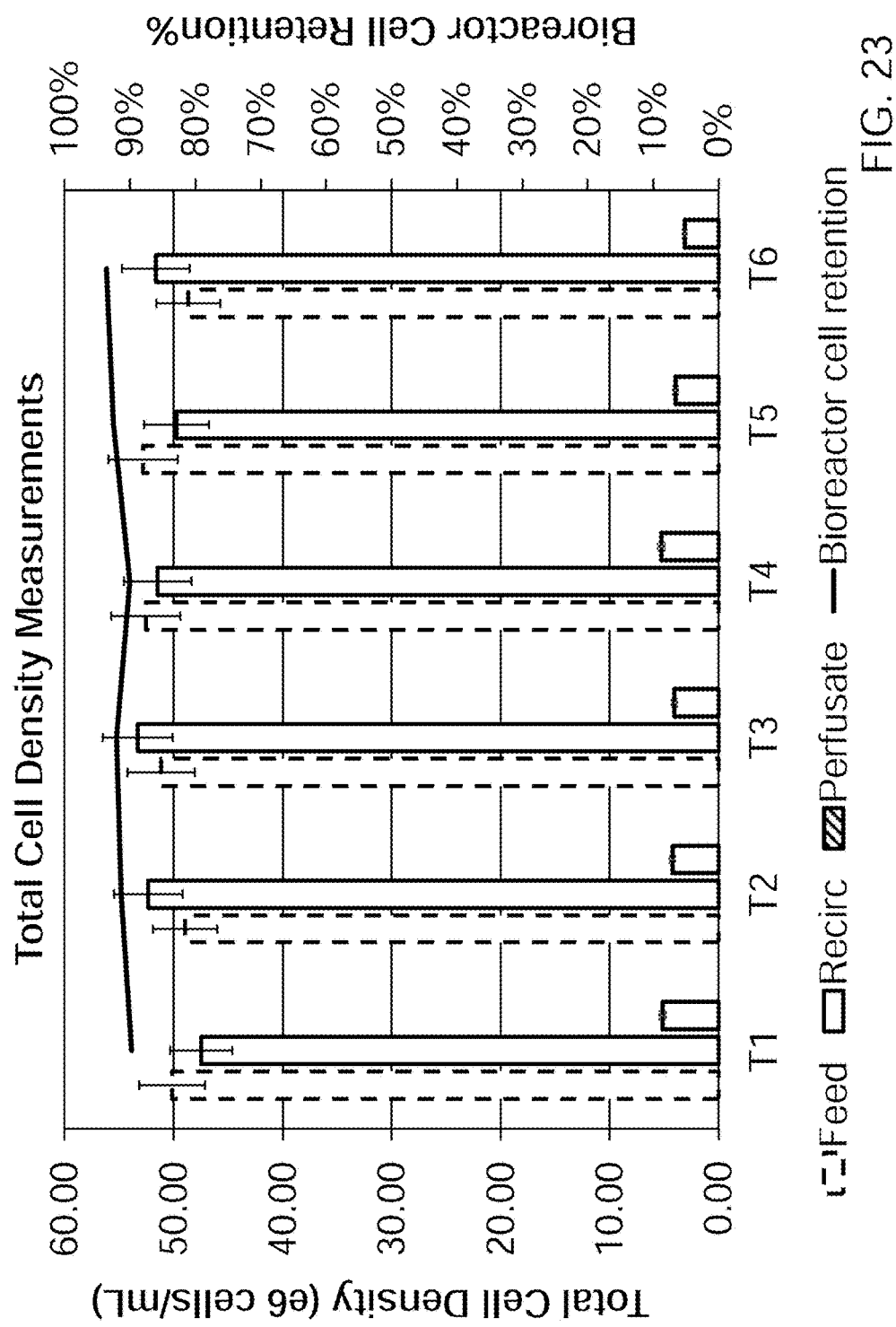
FIG. 23 is a graph showing the total cell density and cell retention for varied flow rates and flow methods for another experiment.
Figure 24:
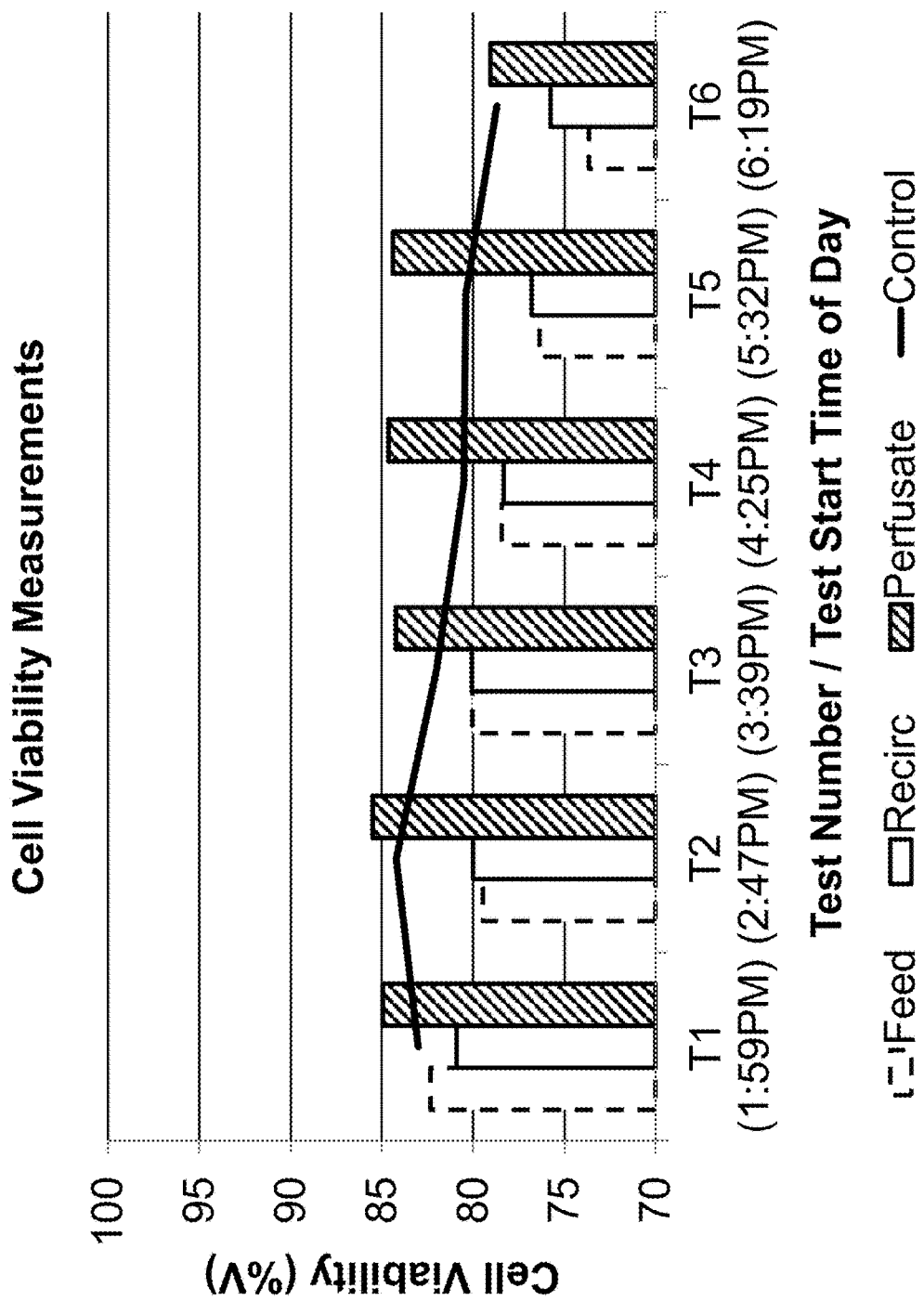
FIG. 24 is a graph showing the cell viability for varied flow rates for the experiment conducted for the graphs of FIG. 23.

FIG. 23 shows the measured total cell density of feed flow, recirculation flow, and perfused flow. The bioreactor cell retention for the tests shows an approximately 90% perfusion efficiency. FIG. 24 shows the measured cell viability for the tests, revealing no significant change in viability across the tests.

Next, additional testing was performed using a solution designated "CHO Line B". The solution had a starting cell density of 75×10$^6$ cells/mL, a turbidity of 2,300 NTU, and cell viability of roughly 80%. The solution was separated using a device of the present disclosure in a system having a reactor size of 2.7 L. Four tests were performed (T1-T4). Two of the tests (T1, T3) used a device having a single transducer. The other two tests (T2, T4) used a device having two transducers in series (such that the fluid ran through both standing waves). The parameters for the tests are shown in Table 3 below.

TABLE 3

| System results for a 2.7 L reactor and feed volume from 1.5 L-2.0 L | | | |
|---|---|---|---|
| T1 | | T2 | |
| Transducers | 1 | Transducers | 2 |
| VVD | 1 | VVD | 1 |
| Perfused Flow (mL/min) | 1.9 | Perfused Flow (mL/min) | 1.9 |
| Feed Flow (mL/min) | 75 | Feed Flow (mL/min) | 75 |
| T3 | | T4 | |
| Transducers | 1 | Transducers | 2 |
| VVD | 2 | VVD | 2 |
| Perfused Flow (mL/min) | 3.8 | Perfused Flow (mL/min) | 3.8 |
| Feed Flow (mL/min) | 150 | Feed Flow (mL/min) | 150 |

Figure 25:
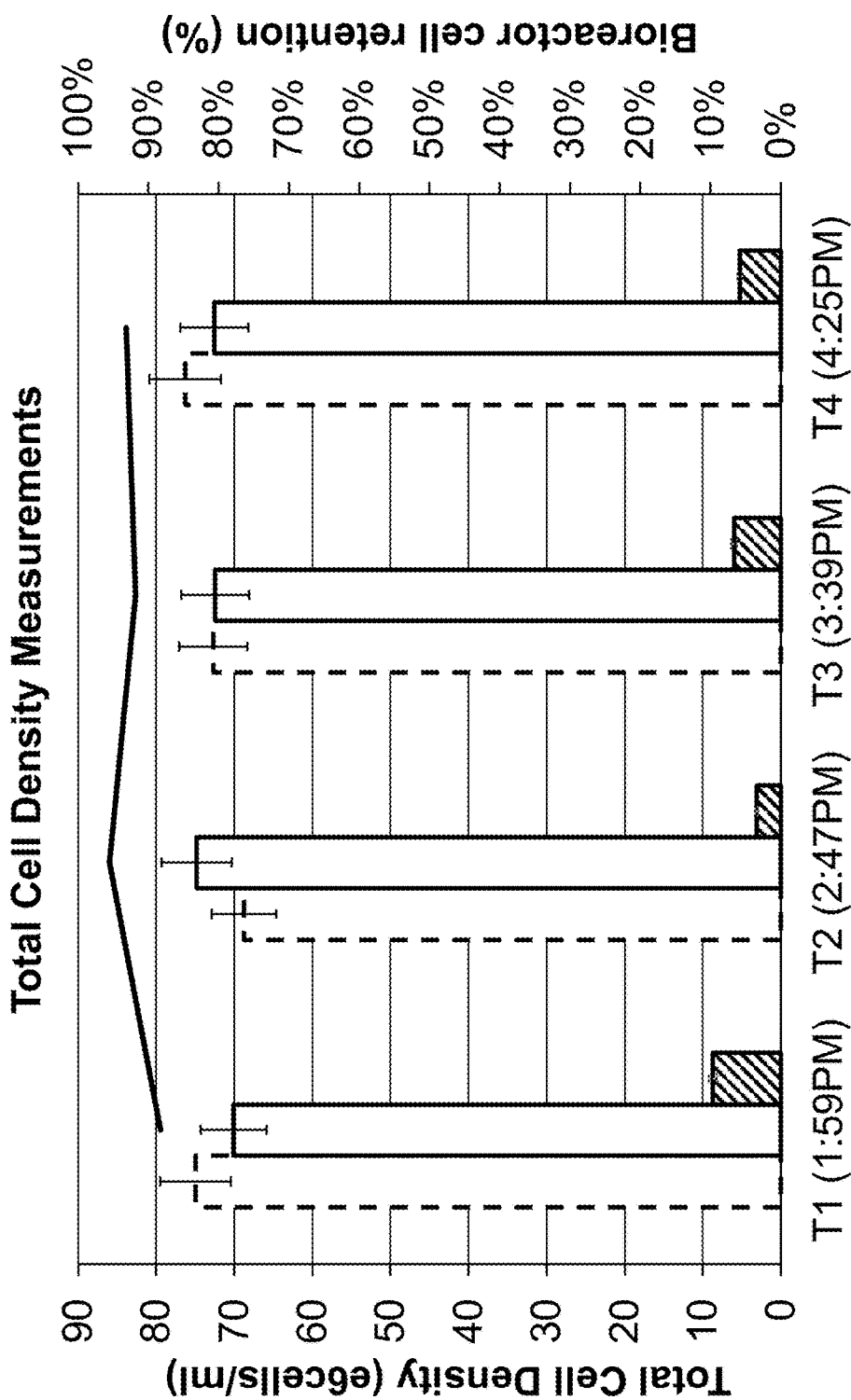
FIG. 25 is a graph showing the total cell density and cell retention for varied numbers of ultrasonic transducers for another experiment.
Figure 26:
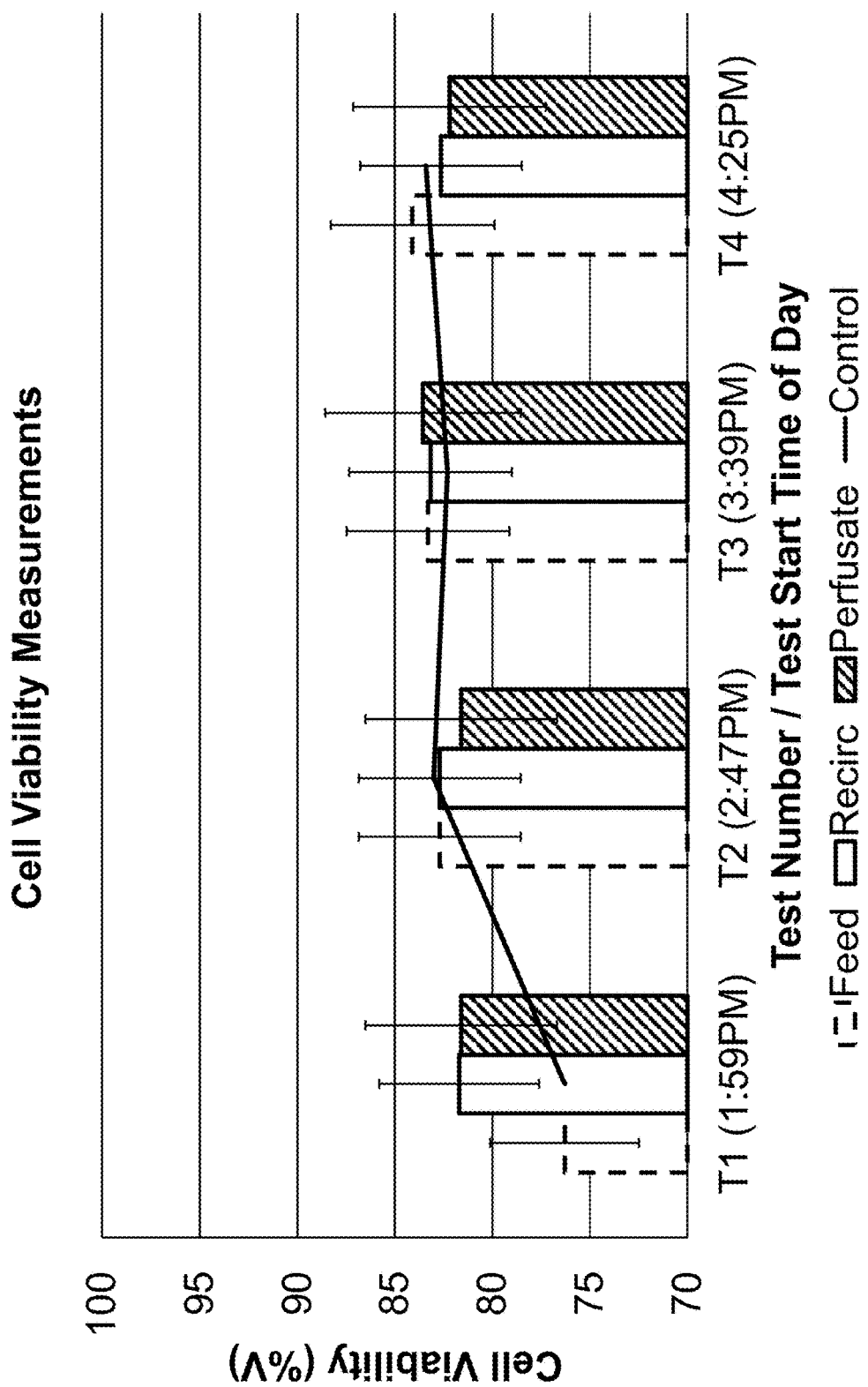
FIG. 26 is a graph showing the cell viability for varied numbers of ultrasonic transducers for the experiment conducted for the graph of FIG. 25.

FIG. 25 shows the measured total cell density of feed, recirculation, and perfusion flows. The bioreactor cell retention for the tests shows a perfusion efficiency greater than 90%. The results further evidenced an approximately 3-5% greater efficiency when using two transducers rather than a single transducer. FIG. 26 shows the measured cell viability for the tests, revealing no significant change in viability across the tests. Practically speaking, operating at low VVD offers a number of advantages, such as media cost reduction.

Example 2

Figure 27:
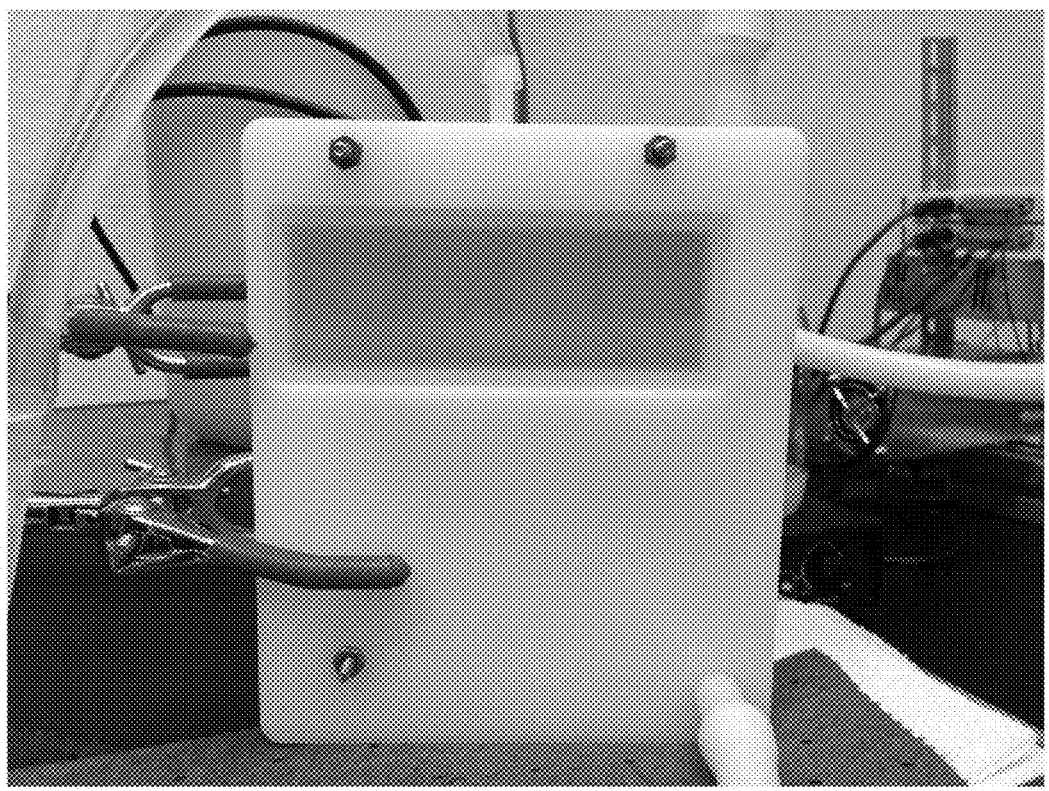
FIG. 27 is a picture of another acoustic perfusion device that was tested.

FIG. 27 shows another experimental setup for an acoustic perfusion device similar to that illustrated in FIG. 8. Tubes are connected to the inlet port, outlet port, and the collection port.

Figure 28:
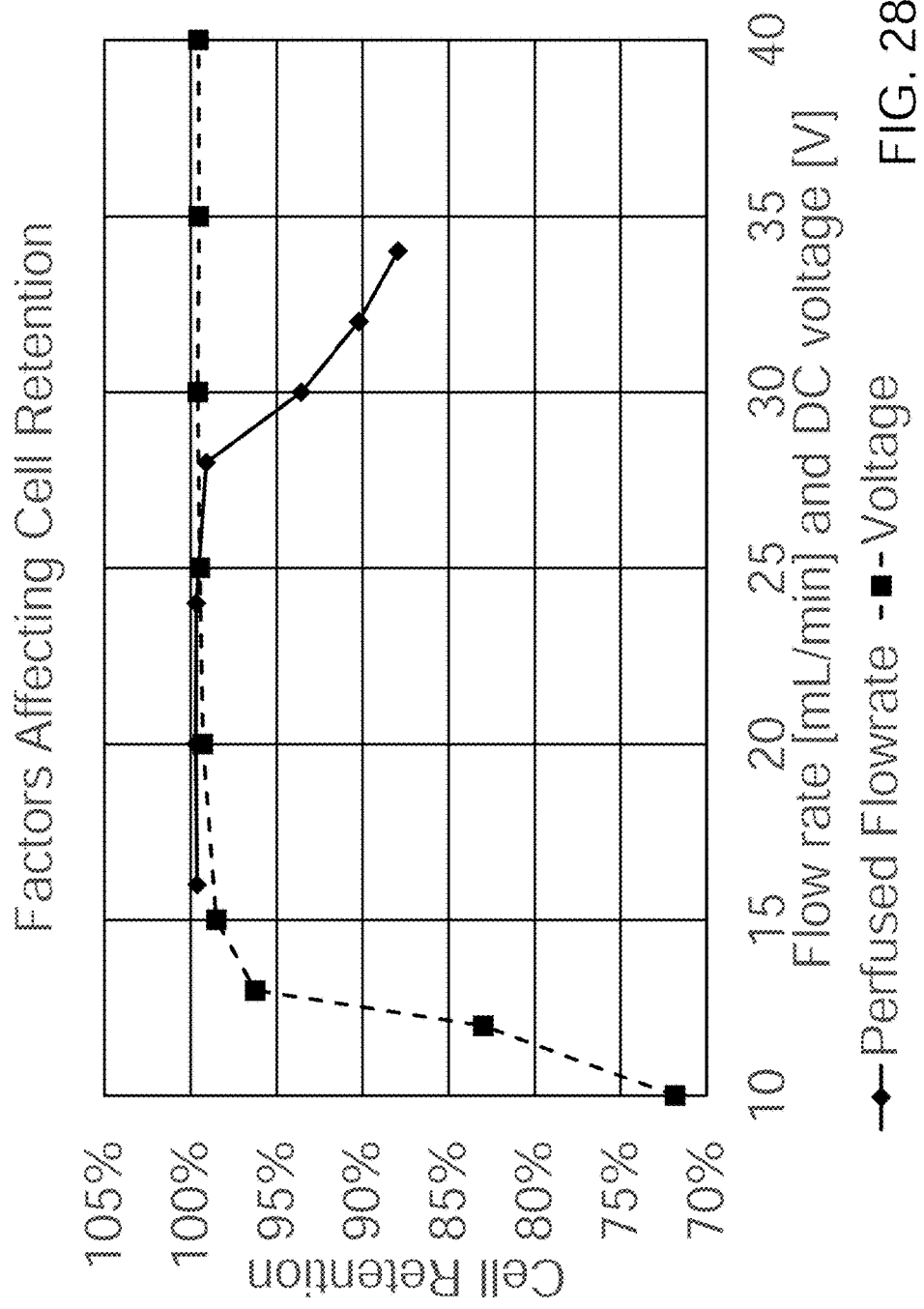
FIG. 28 is a graph showing the effect of the perfused flow rate or the transducer voltage on the cell retention.

The device was tested at a transducer voltage of 40V peak to peak, a perfused flow rate of 15-30 mL/min, and a recirculation flow rate of 2 L/min. Samples were taken every 45-60 minutes, and the cell retention rate was determined. FIG. 28 shows the results. The y-axis is the retention, stated in terms of percentage (calculated by comparing the output cell count with the input, or bioreactor/culture cell count). The x-axis is both the applied DC voltage (in V) and the perfused, or harvest, flow rate (in mL/min); it is merely coincidental that the range of numeric values for V and mL/min are the same. The cell retention efficiency remained above 95% for perfused flow rates up to 20 mL/min, and remained above 90% up to about 25 mL/min. FIG. 33 is a composite picture showing the device in a startup or cell settling mode (left) and in a steady state cell retention mode (right).

Next, experiments were performed to determine what factors would affect cell retention. The perfused flow rate was varied, as was the transducer voltage. When the perfused flow rate was varied, the transducer voltage was maintained at 40V peak to peak and the recirculation flow rate was maintained at 2 L/min. When the transducer voltage was varied, the perfused flow rate was maintained at 20 mL/min and the recirculation flow rate was maintained at 2 L/min. The results indicated that, for this particular embodiment, a perfused flow rate of about 15 mL/min to about 28 mL/min was optimum, and a transducer voltage of about 15V peak to peak to about 28V peak to peak was optimum.

Figure 29A:
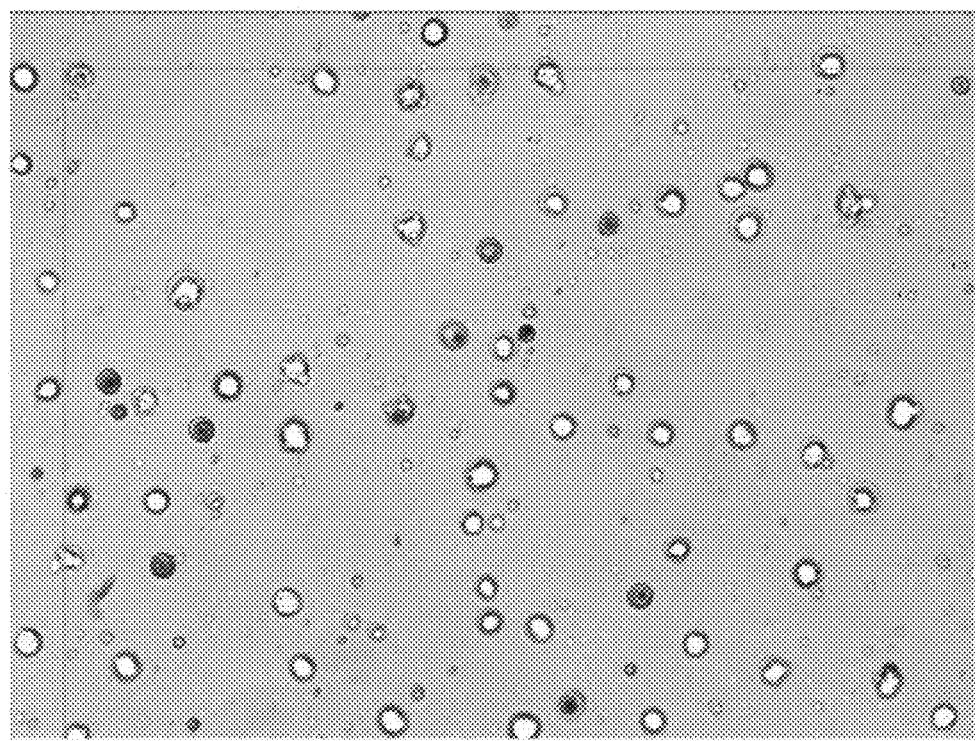
FIG. 29A is a microscope image from a ViCell Cell Analyzer of the particles in the feed stream going into the device. The feed stream is a bioreactor fluid containing CHO cells, protein, and cell fragments.
Figure 29B:
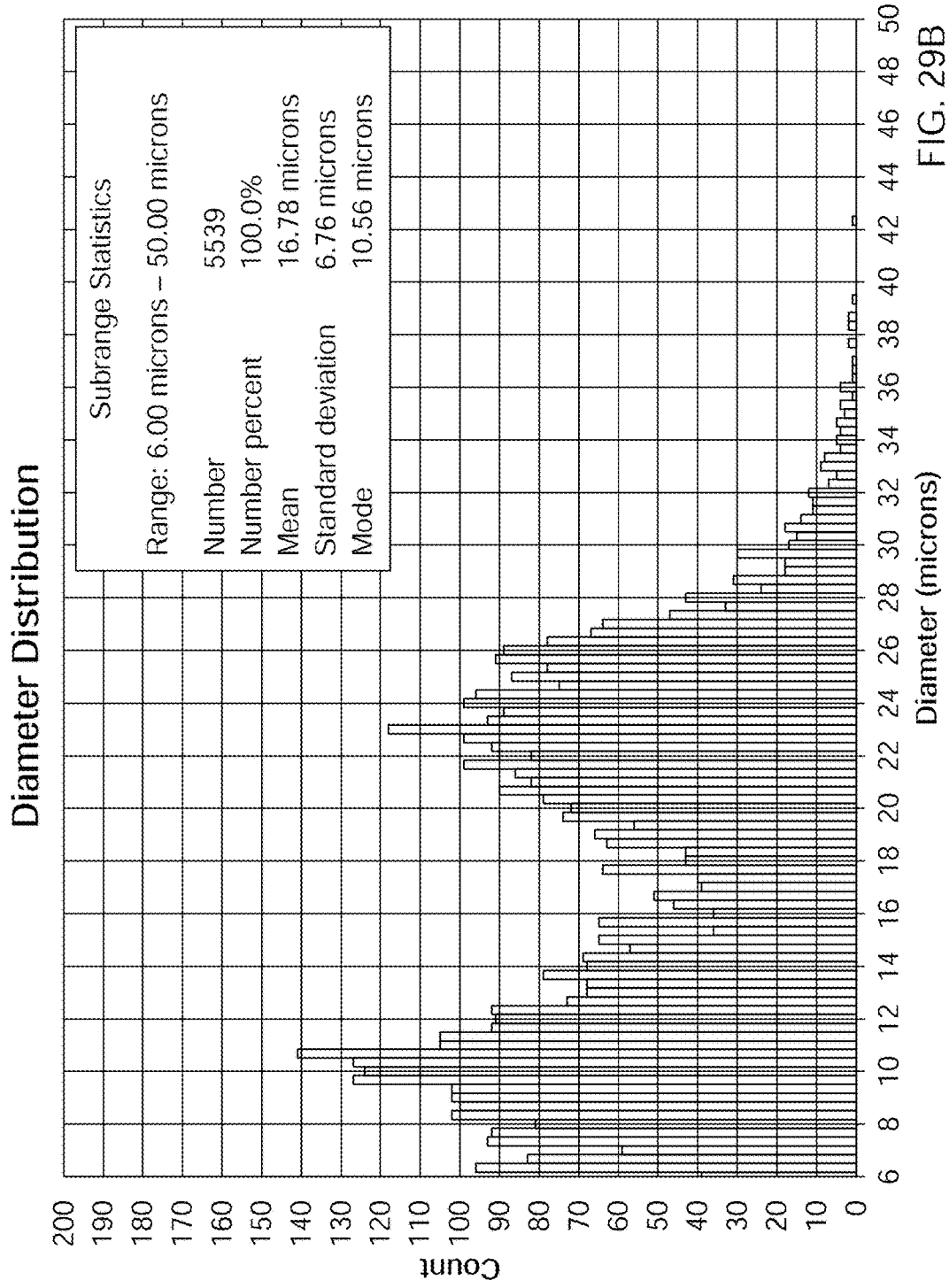
FIG. 29B is a graph of the particle diameter distribution of the feed, showing a bimodal distribution.

A better understanding of the added functionality provided by an acoustic perfusion device can be demonstrated by examining the observed cell samples coming in and being harvested from the device. FIG. 29A is a microscope image (from a Vi-Cell cell counter) of the feed suspension, here a viable cell culture population with approximately 56 million cells/mL. Several large, round, healthy cells can be observed. FIG. 29B is a histogram showing the distribution of cell diameter in the population. The diameter distribution is strongly bi-modal, around values of about 11 microns and about 23 microns. These two modes correspond roughly with the smaller debris and non-viable cells, and the larger viable cells. It should be noted that this sample is from a particularly "dirty" cell population. In general, a production cell line would be far cleaner, and the peak at approximately 11 microns would be much smaller, or even non-existent.

Figure 30A:
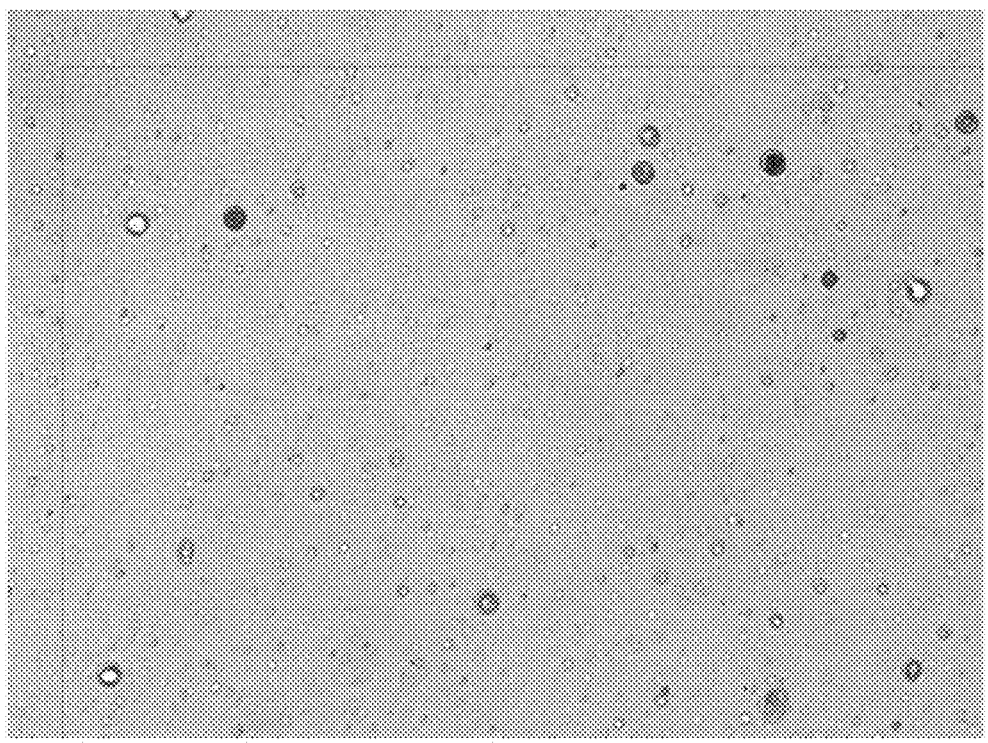
FIG. 30A is a microscope image of the perfusate (or clarified harvest flow) exiting the device.

FIG. 30A is another microscope image (from a Vi-Cell cell counter), this time of the flow harvested from the acoustic perfusion device. In this image, very few bright, large cells are observed, in contrast to FIG. 29A. Rather, the image is filled with more smaller, darker particles, or debris.

The experimental conditions in this case were a perfused rate of 4 mL/min and a recirculation rate of 2 L/min with a DC input voltage of 30V. This qualitative observation is confirmed by the histogram in FIG. 30B, which shows the distribution of diameters in the perfusate. Looking at FIG. 30B, the particle distribution is now unimodal, with the peak of approximately 9 microns. This distribution indicates that the larger, viable cells have been trapped and retained, or otherwise largely prevented from exiting in the perfusate. Smaller cells are passing through, together with cell debris, fines, and fragments, from submicron to micron sized.

Figure 31:
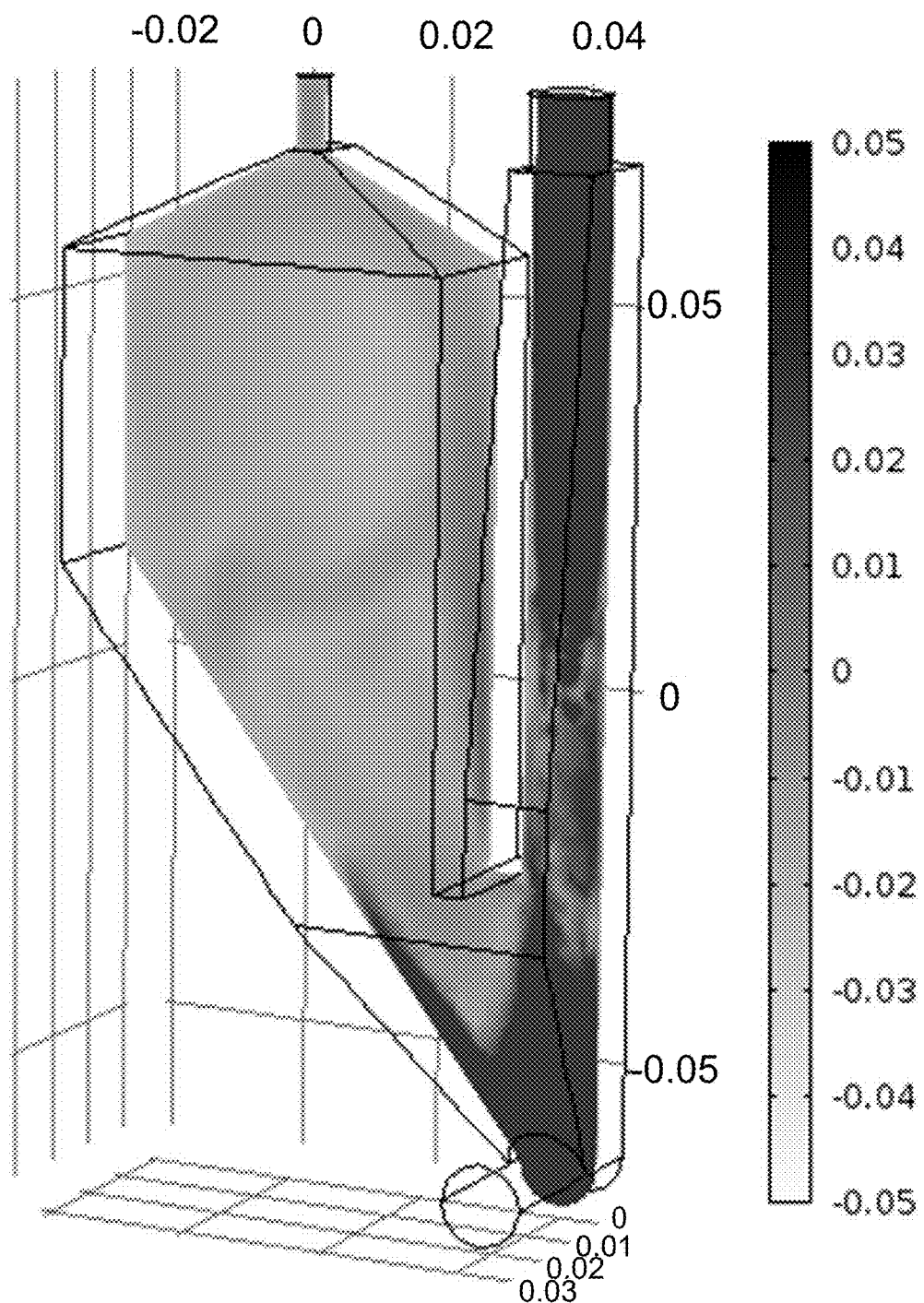
FIG. 31 is a CFD model showing the velocity distribution within the device of FIG. 27. The text at the top of the scale reads "×$10^{-2}$". The text at the top of the scale by the upward-pointing triangle reads "0.678". The text at the bottom of the scale by the downward-pointing triangle reads "0". The triangles show the maximum and minimum values depicted in this figure for the given scale. The scale runs from 0 to 5 m/s in intervals of 0.5, with black indicating 5 at the top of the scale, and white indicating zero at the bottom of the scale.

A computational fluid dynamics (CFD) model was made of this device. FIG. 31 shows the velocity distributions within the device after 500 seconds. The units are in meters/second (m/s). As expected, the highest velocities are found in the channel leading downwards from the inlet port to the outlet port. The velocity is near zero in the fluid cell and out through the collection port. This velocity profile is important for two reasons: the acoustic field is more effective in a flow with a lower, more uniform velocity, and because the cells used in bio-manufacturing are sensitive to flow, and the induced shear rate.

FIG. 32 is a diagram illustrating several aspects of this embodiment. Fluid flows into the device through the inlet port 710 (arrow 780) and into the acoustic chamber 790. The volume of fluid 750 below the acoustic chamber contains the tangential flow path, indicated by arrow 782. Fluid with a relatively high amount of viable cells will exit through the outlet port 730, as indicated by arrow 781. The acoustic interface effect/region created by the standing waves is marked with reference numeral 783, and is upstream of the acoustic standing wave field 784. The acoustic interface roughly coincides with an x-y plane in this diagram. This interface effect separates large cells from smaller cell fragments, particulate debris, desired biomolecules, etc., which can pass through the interface 783 and the acoustic standing wave field 784. By way of comparison, the cell aggregates that arise within the acoustic standing wave field 784 during the first mode of operation (see FIG. 41) can be described as being aligned in the y-z plane. In operation, the separation caused by the interface effect occurs at the interface region 783 as any large cells are held back by the "interface" or "barrier" effect. The harvest flow stream 785 containing the smaller fragments, particulate debris, desired biomolecules, etc. then exits through harvest port 770. The tangential flow path is part of the inlet flow path, and is located below the interface region 783 generated by the acoustic standing wave. The tangential flow path will transport away both the clusters of cells that drop from the acoustic standing wave field 784 due to gravity effects and the cells that are retained by the acoustic interface effect.

FIG. 61 shows a device 6100 that is substantially similar to the device 700 of FIG. 7 and FIG. 32. The same numbering is used in FIG. 61. The main difference between the device illustrated in FIG. 32 and that illustrated in FIG. 61 is the flow of particles near transducers 760, which is illustrated with arrow 6153, which runs down past the transducers 760 and down to acoustic interface effect/region 783. This flow pattern near transducers 760 occurs because the particles in FIG. 61 are too small or have an acoustic contrast factor that is insufficient to be affected by the acoustic standing wave created by transducers 760 (and the reflector), and so they can reenter the acoustic standing wave. This behavior may also be affected by the buoyancy characteristics of the particles and the fluid flow of the system, and thus the Stokes drag experienced by the particles.

Example 3

Another way of explaining the operation of the acoustic perfusion device can be understood by looking at the results of a numerical study. In the numerical study, two fluids with differing effective acoustic properties (i.e., speed of sound and density), were modeled with an interface between them in COMSOL, a numerical simulation software. The acoustic field is calculated and therefrom the lateral radiation force acting on a particle in the direction of the fluid velocity is calculated using Gorkov's equation.

Figure 34:
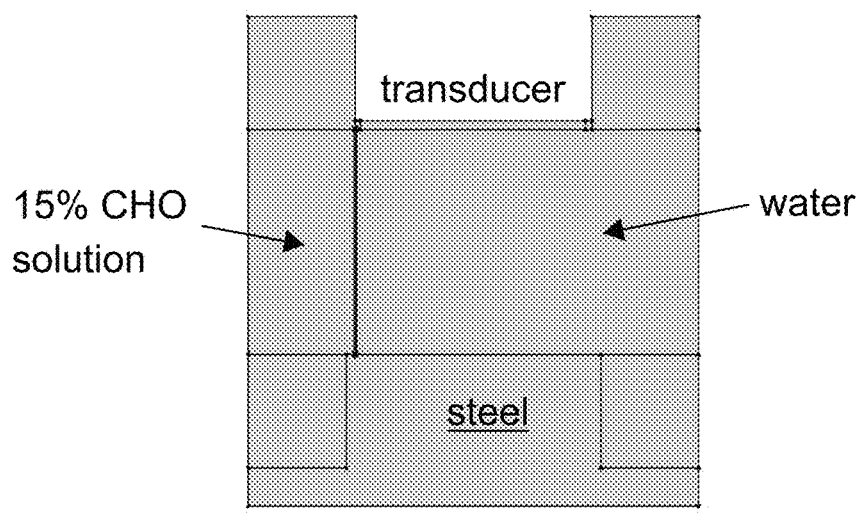
FIG. 34 shows the geometry of a model simulation of the acoustic device used for cell retention. The model contains two fluids, one a clarified fluid within the acoustic field, the other a high cell density fluid to the left of the acoustic field, a piezoelectric transducer, a steel reflector, and an aluminum housing. The first fluid was water within the acoustic field and the second fluid was a 15% concentration of CHO cells in water solution outside (to the left) of the acoustic field. The blue solid line in the model indicates the separation line between the two fluids.

FIG. 34 shows the geometry of the simulation, utilizing a piezoelectric transducer, steel reflector, aluminum housing, and two fluids: the first fluid being water within the acoustic field, simulating the clarified fluid, and the second fluid being a 15% concentration of CHO cells in water solution outside of the acoustic field, the second fluid having a higher density and higher speed of sound than the water fluid and simulating the bioreactor fluid containing the cells.

The two fluids were separated as indicated by the solid line in the model of FIG. 34. In this setup, the fluid velocity through the system was in a horizontal direction from left to right. Therefore, in order to act as a retention device, the acoustic field needs to generate a force on the cells that acts in the negative x-direction (i.e, opposite the fluid velocity). Water was modeled with a fluid density of 1000 kg/m$^3$ and a speed of sound of 1500 m/s. CHO cells were modeled having a density of 1050 kg/m$^3$ and a speed of sound of 1550 m/s. A coupled multi-physics numerical simulation that included a full piezoelectric simulation of the piezoelectric material, an acoustic simulation of the two fluids, and a linear elastic simulation in the steel and aluminum bodies was performed at various frequencies of excitation. The transducer was driven at a peak voltage of 40 V.

Figure 35A:
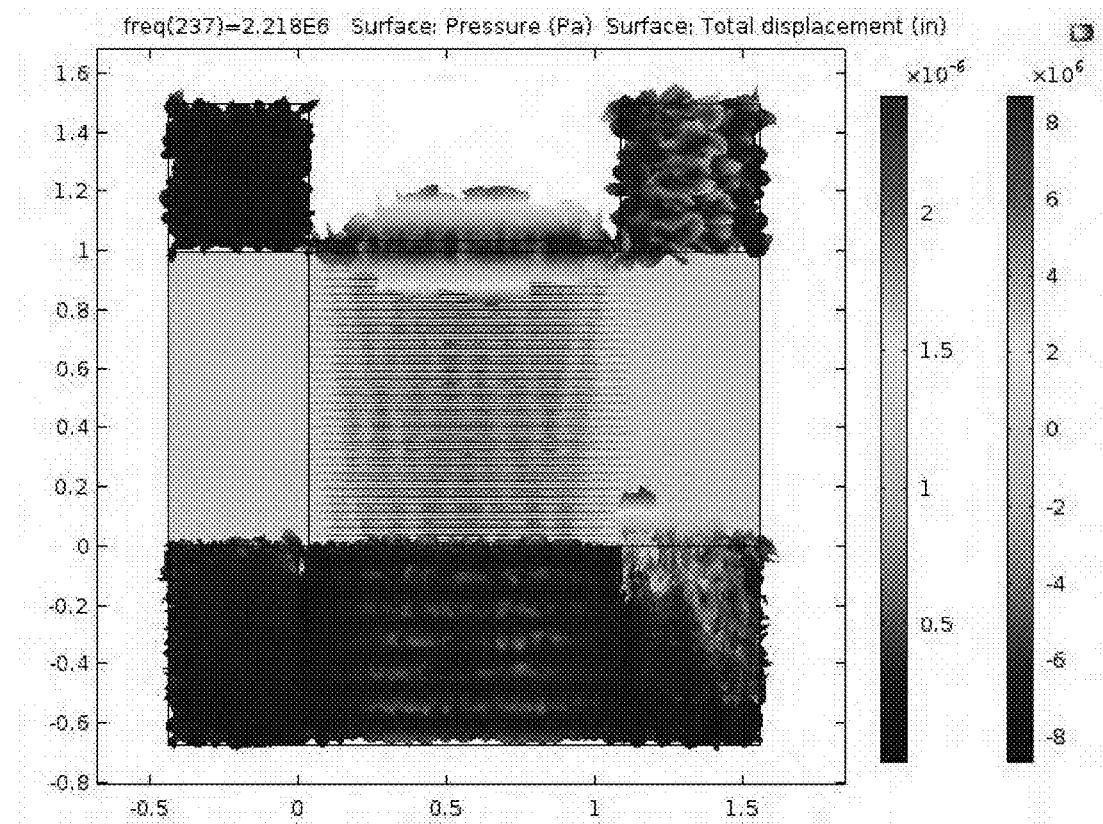
FIGS. 35A, 35B, and 35C are graphs showing the displacement of the piezoelectric material, the aluminum housing, and the steel reflector (left-side scale); and the acoustic pressure in the two fluids (right-side scale) of the model simulation of FIG. 34 at several frequencies of operation.
Figure 35B:
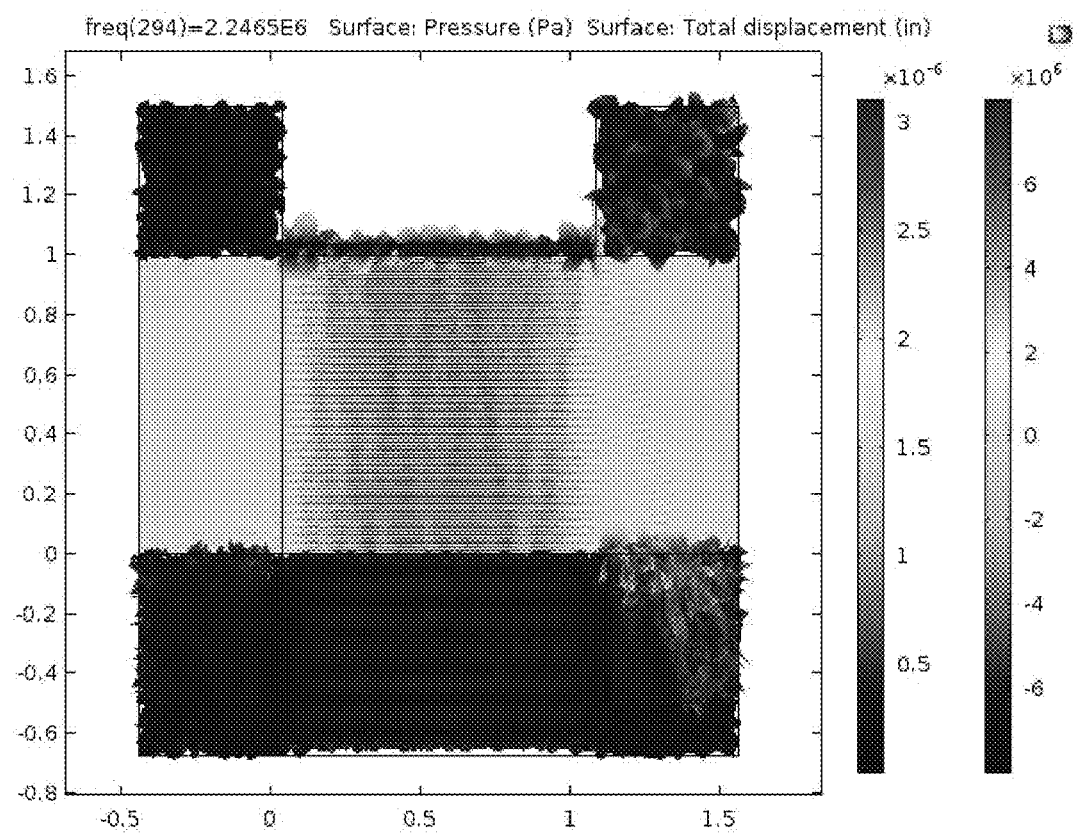
Figure 35C:
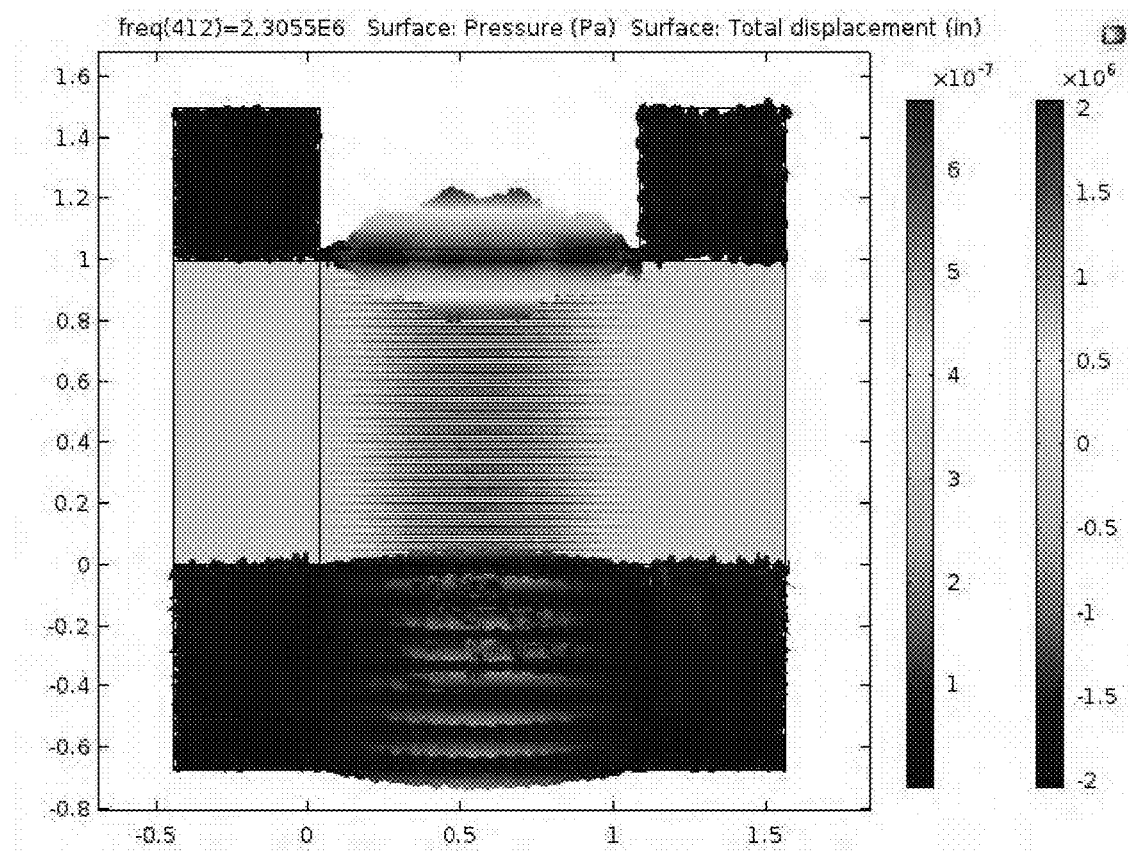

FIGS. 35A-35C show the acoustic pressure in the two fluids and the displacement of the piezoelectric material, the aluminum housing, and the steel reflector of the model at frequencies of operation of 2.218 MHz, 2.2465 MHz, and 2.3055MHz. The lateral radiation force (i.e., horizontally in the direction of the fluid flow), was calculated at the interface between the two fluids along with real electrical power consumed by the transducer. The structural displacement of the transducer and steel are shown, along with the acoustic pressure in the fluid.

FIG. 36 shows the lateral radiation force (N) and the lateral radiation force normalized by power (N/W) versus frequency acting on the suspended CHO cells. This graph shows that at the resonance frequencies (i.e., local maxima in power), the average lateral radiation force on the interface is negative, meaning that it is in the negative-x direction. The result is the creation of an acoustic barrier effect or an acoustic interface effect. That is, the acoustic field at the interface between the two fluids exerts a strong lateral force on the suspended particles in a direction opposite to the fluid flow, thereby keeping the larger particles from entering the acoustic field and allowing the first fluid (i.e., fluid containing smaller particles, such as the desired product, and excluding whole cells) to enter the acoustic field, thereby creating an acoustic perfusion cell retention device. In this way, the clarified fluid can escape and the cells are held back by the radiation force. This force is never positive, meaning that it always holds the cells back at the interface, not allowing them to cross the interface. The multiple peaks in the power curve show the existence of multiple modes of operation including planar resonance modes and multi-dimensional modes of operation, indicating that this type of operation can be generated through utilization of planar and multi-dimensional standing waves alike. In systems having 1"×1" dimensions, there exists a planar resonance about every 30 kHz. The graph shows evidence of additional peaks indicating the existence of the multi-dimensional modes. Per unit power, these modes can be equally or even more effective as the planar resonance modes. As explained above, the cells that are held back by the acoustic radiation force may then be picked up by the scrubbing motion of the flow field (i.e., the recirculating flow underneath the interface), and be continuously returned to the bioreactor to ensure they receive the nutrition and oxygen to maintain the production of the overall cell culture.

Example 4

Figure 37:
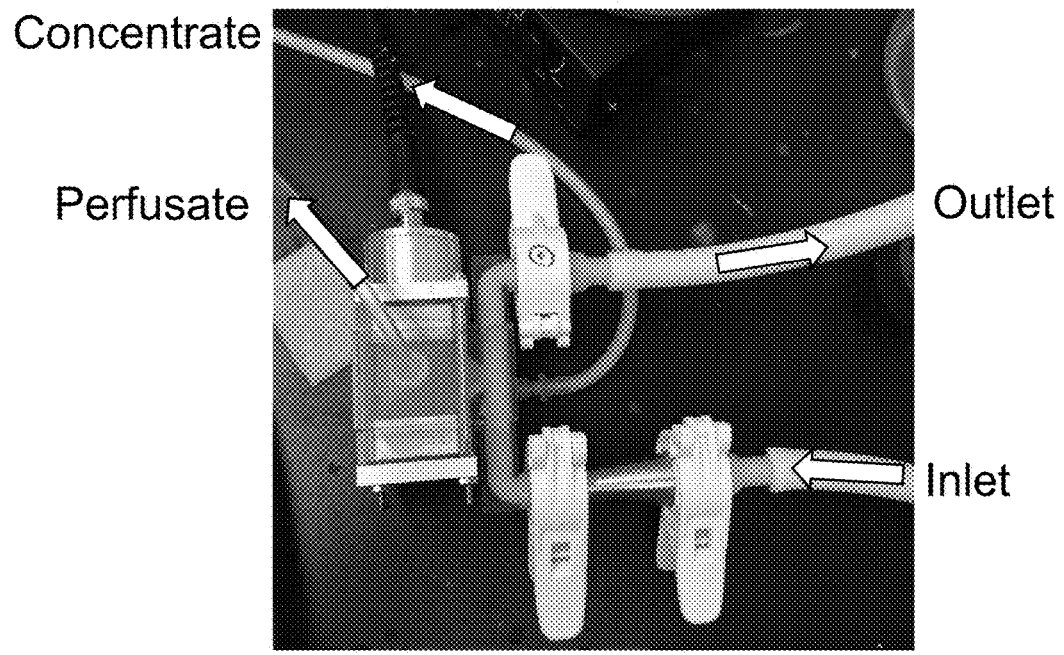
FIG. 37 is a picture (top view) of an acoustic perfusion device of the present disclosure. Arrows indicate the flow into the inlet port; the flow out of the outlet port; the clarified fluid flow out the top of the device and the flow of concentrate out the bottom of the device.
Figure 38:
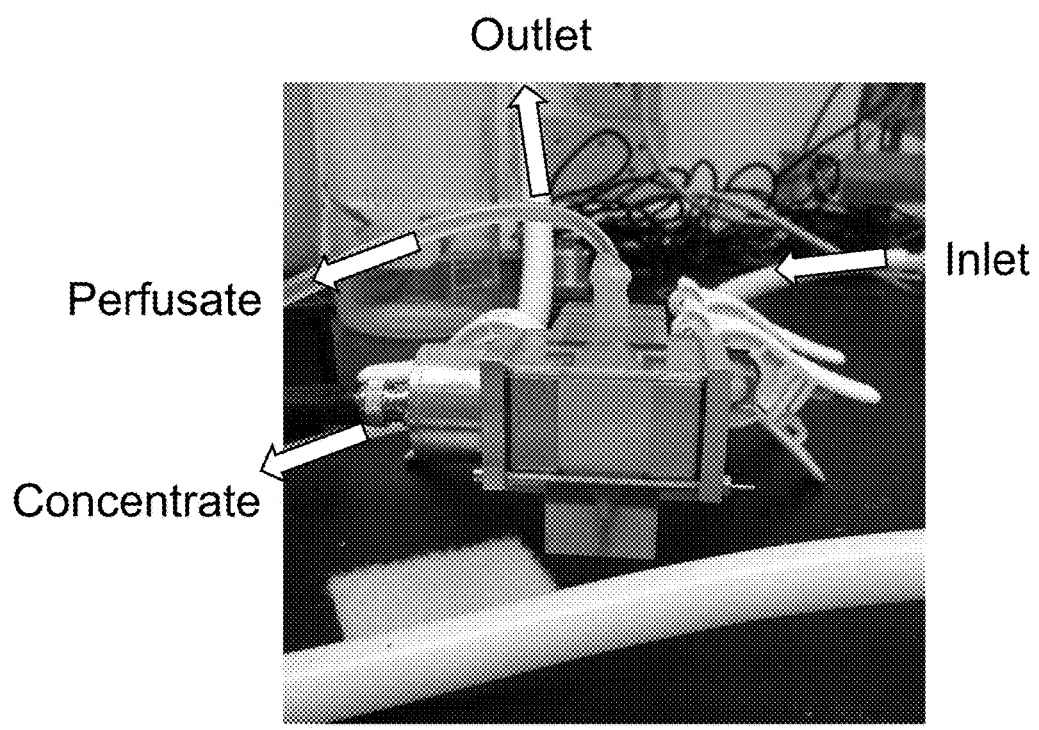
FIG. 38 is a picture (side view) of the acoustic perfusion device of FIG. 37.

FIG. 37 and FIG. 38 show another experimental setup for an acoustic perfusion device similar to that illustrated in FIG. 9. Tubes are connected to the inlet port, outlet port, the collection port, and the secondary outlet port (for a flow concentrated cells). Arrows are included to illustrate fluid flow. Arrows indicate the flow into the inlet port; the flow out of the outlet port; the perfusate flow out the top of the device and the flow of concentrate out the bottom of the device. The flow through the inlet port to the outlet port is the recirculation flowrate. The perfusate flow out the top of the device is the perfused flowrate containing clarified fluid depleted in cells and containing desired product. The flow of concentrate out the bottom of the device is the concentrated cell flow. The concentrated cell flow can be used for a cell bleed operation or if desired, the cells can be returned to the bioreactor.

Figure 39:
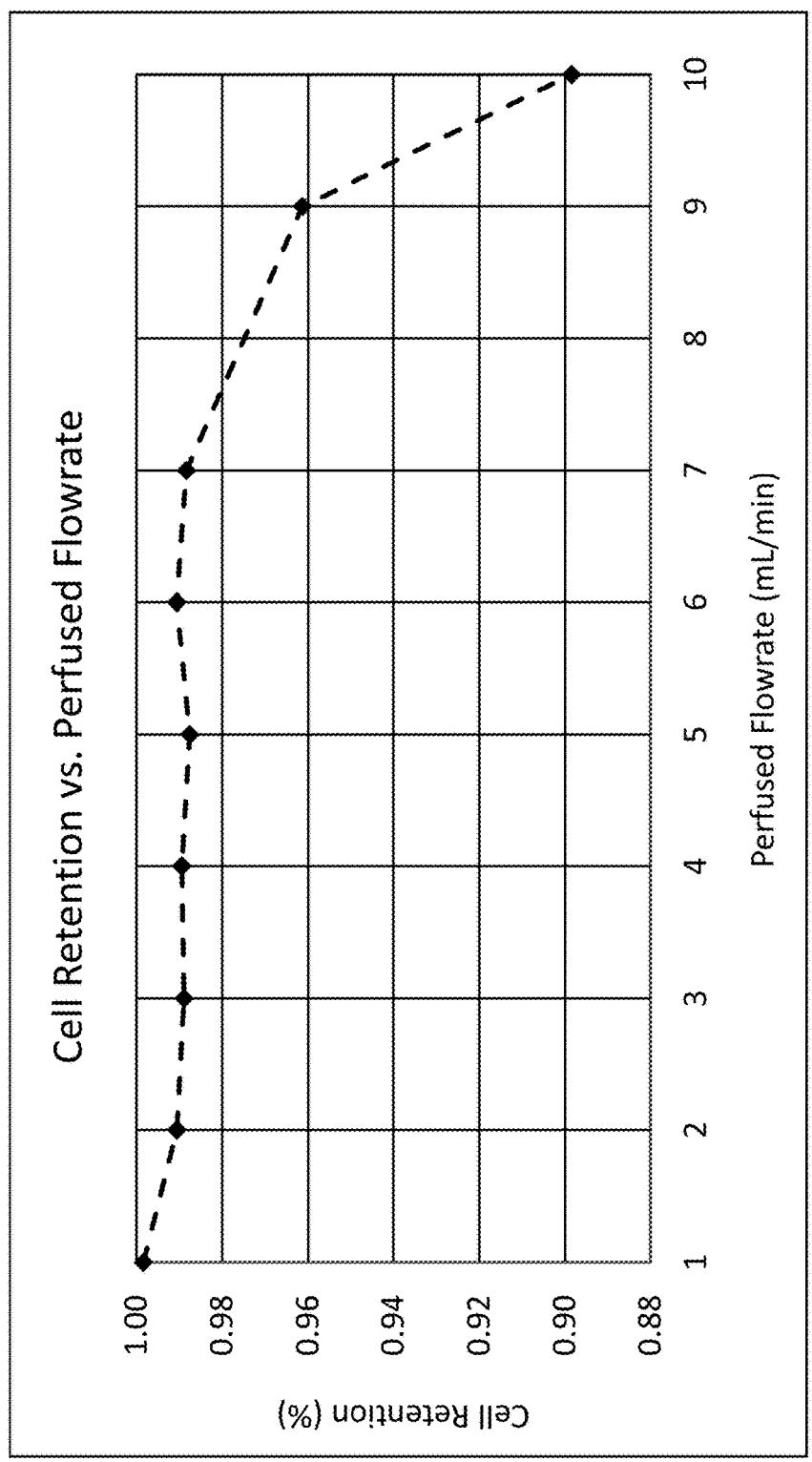
FIG. 39 is a graph of cell retention vs. perfusate flowrate for the device of FIG. 37.

The device was tested at a transducer voltage of 40V peak to peak, a perfused flow rate (out the top) of 1-10 mL/min, a recirculation flow rate of 0.75-1 L/min, and a concentrate flow rate (out the bottom) of 15 mL/min. The cell retention rate was determined for different perfused flowrates. FIG. 39 shows the results. The y-axis is the retention with 1.00 indicating 100% retention. The cell retention efficiency remained above 98% for perfused flow rates up to 7 mL/min, and was just below 90% at 10 mL/min.

Example 5

Figure 50:
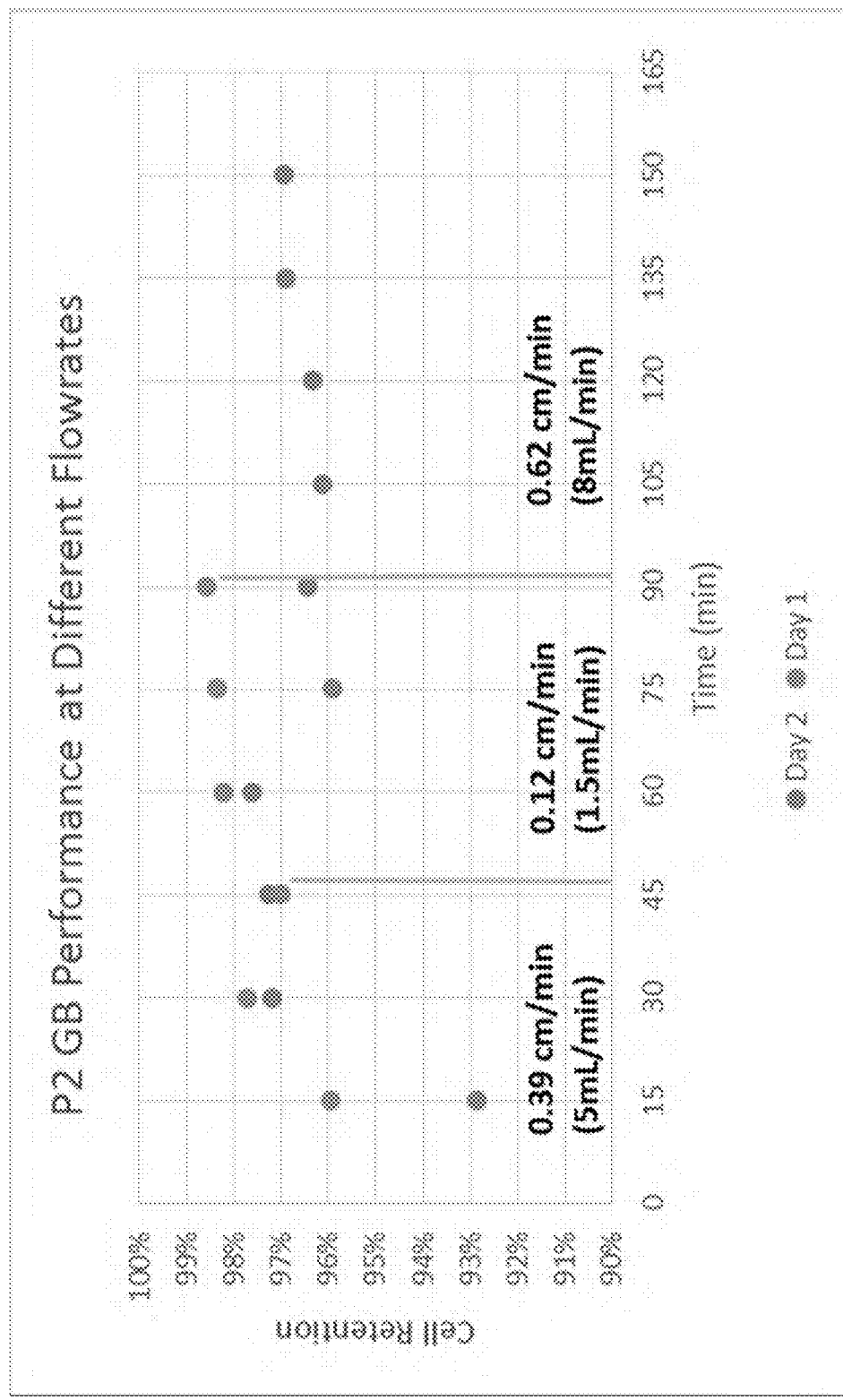
FIG. 50 is a graph of cell retention versus time for the device of FIG. 7. The y-axis runs from 90% to 100% in intervals of 1%. The x-axis runs from 0 to 165 minutes in intervals of 15 minutes. Tests were performed on two different days.
Figure 51:
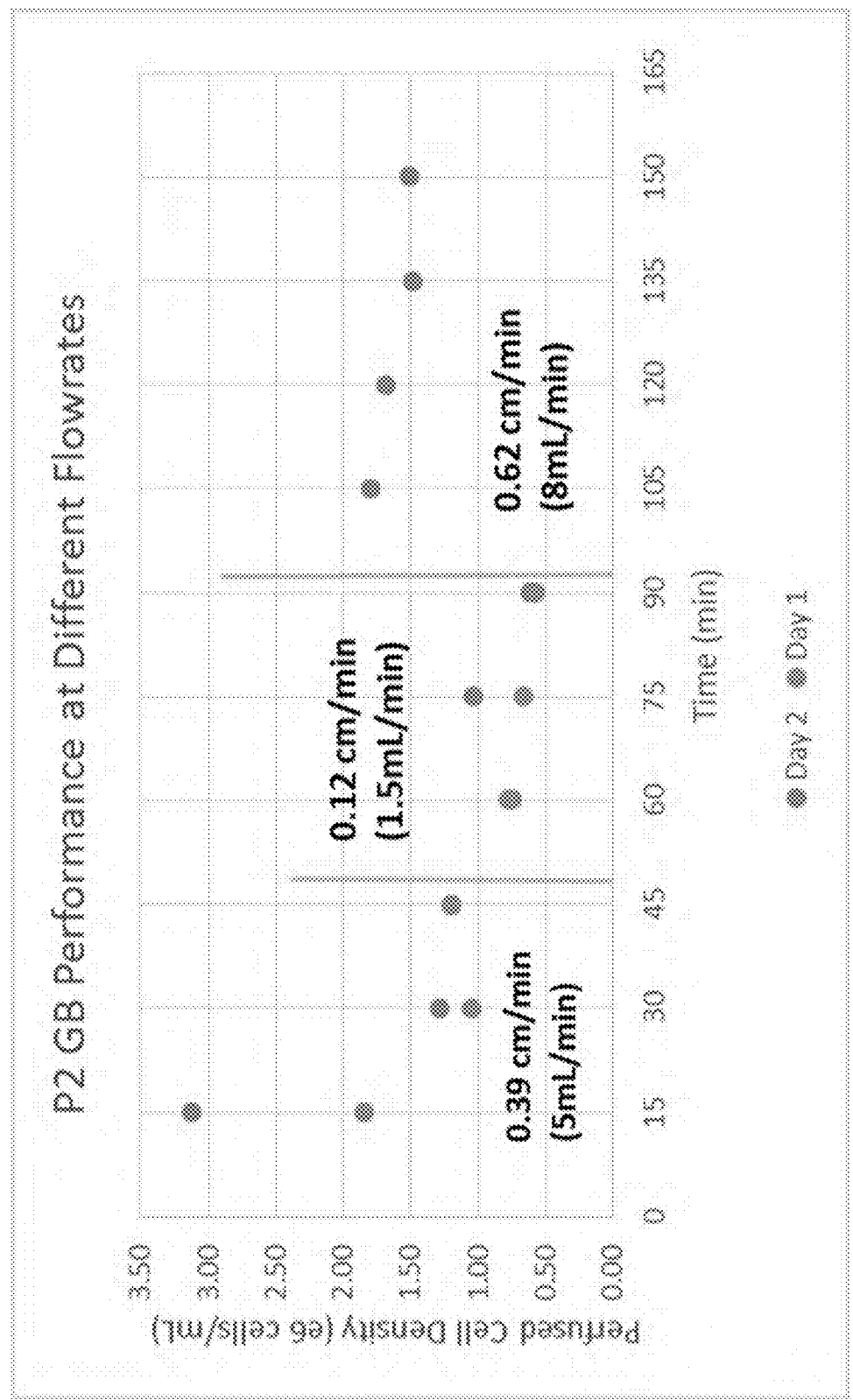
FIG. 51 is a graph of perfusate cell density (million cells/mL) versus time for the device of FIG. 7. The y-axis runs from 0.00 to 3.50 in intervals of 0.50. The x-axis runs from 0 to 165 minutes in intervals of 15 minutes. Tests were performed on two different days.

The device of FIG. 7 and FIG. 8 was tested at different flowrates on two different days. FIG. 50 shows the cell retention (%) versus time. Here, higher values are more desirable, and most values were over 95% at flowrates ranging from 1.5 mL/min to 8 mL/min. FIG. 51 shows the perfusate cell density (million cells/mL) versus time. Here, lower values are more desirable (indicating successful cell separation). As expected, results were better at lower flowrates.

Example 6

Figure 52:
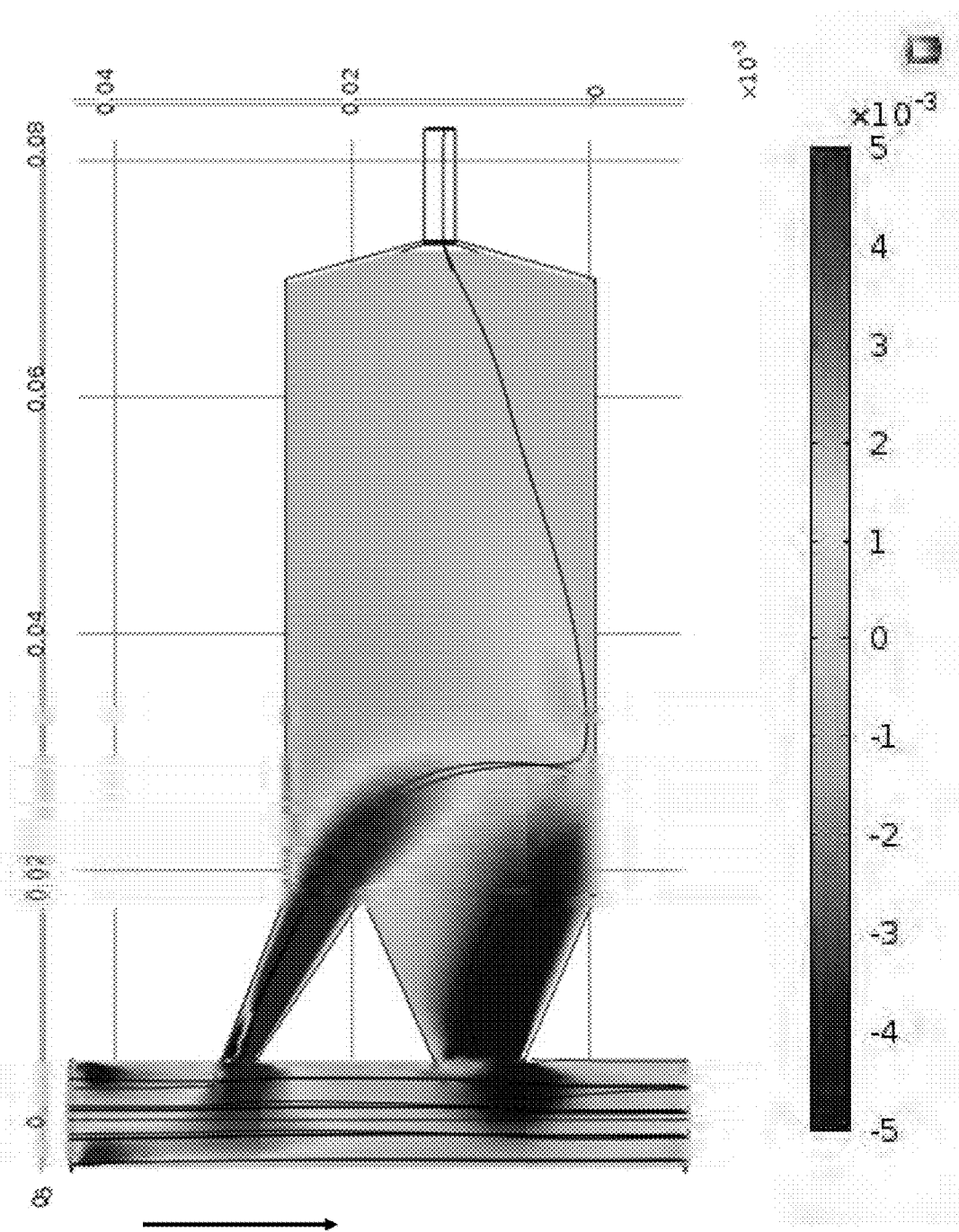
FIG. 52 is a CFD model showing the velocity distribution within the device of FIG. 46A. The text at the top of the scale reads "×10$^{-3}$". The scale runs from −5 to 5 m/s in intervals of 1.

A computational fluid dynamics (CFD) model was made of the device with the internal structure of FIG. 46A. FIG. 52 shows the velocity distributions within the device after 500 seconds. The units are in meters/second (m/s). It is noted that here, the inlet is from the left-hand side of the figure, and the outlet is on the right-hand side of the figure (flow direction indicated by the arrow). As expected, the highest velocities are found in the inflow passageway into the acoustic chamber. Negative velocities in the outflow passageway indicate flow out of the acoustic chamber. The velocity is near zero in the acoustic chamber, and near the collection port at the top thereof. This velocity profile is desirable for perfusion operation.

Figure 54:
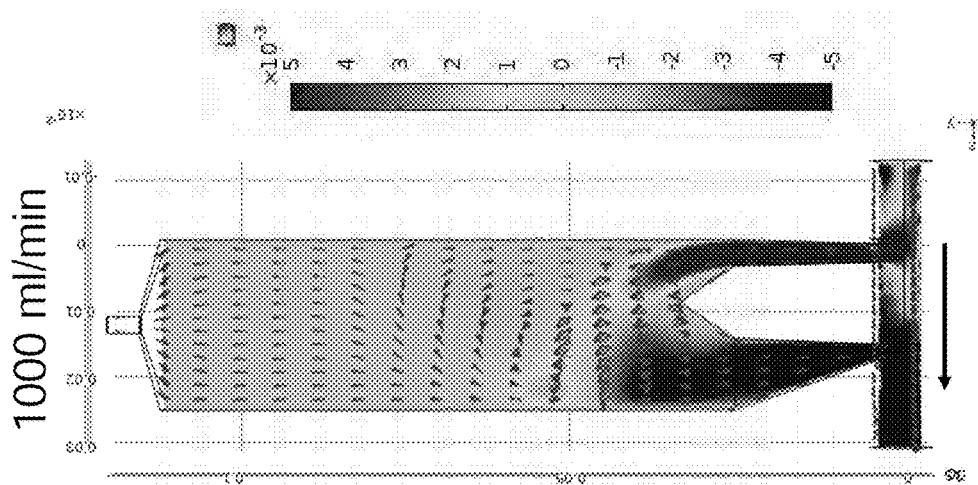
FIG. 54 is a CFD model showing the velocity distribution within the device of FIG. 46C at 1000 mL/min flowrate. The text at the top of the scale reads "×10$^{-3}$". The scale runs from −5 to 5 m/s in intervals of 1.
Figure 53:
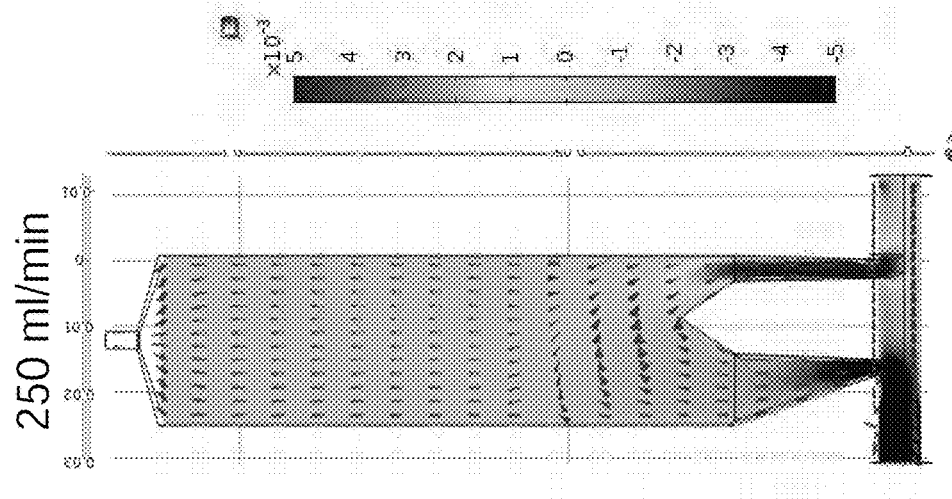
FIG. 53 is a CFD model showing the velocity distribution within the device of FIG. 46C at 250 mL/min flowrate. The text at the top of the scale reads "×10$^{-3}$". The scale runs from −5 to 5 m/s in intervals of 1.

A computational fluid dynamics (CFD) model was also made of the device with the internal structure of FIG. 46C. FIG. 53 shows the velocity distributions within the device at a flow rate of 250 mL/min, while FIG. 54 shows the velocity distributions within the device at a flow rate of 1000 mL/min. In these two figures, the inlet is from the right-hand side of the figure, and the outlet is on the left-hand side of the figure (flow direction indicated by the arrow). Again, the velocity is near zero in the acoustic chamber, and near the collection port at the top thereof, even at the much higher flow rate of 1000 mL/min. This velocity profile is desirable for perfusion operation.

Two further CFD models were made of variants of the configurations seen in FIG. 53 and FIG. 54, which are potential internal structures for the device of FIG. 43. The first variant is seen in FIG. 55. Here, the rectangle at the top indicates the location of the ultrasonic transducer/multi-dimensional acoustic standing wave. Below this rectangle, the sides of the acoustic chamber taper evenly down to the outflow passageway. The inflow passageway has an arcuate top into the acoustic chamber. The second variant is seen in FIG. 56. This variant is much taller and narrower compared to FIG. 55. The outflow side of the acoustic chamber tapers evenly down to the outflow passageway. As seen in both figures, the desirable velocity profile is present, being near zero in the area of the multi-dimensional acoustic standing wave, and near the collection port at the top thereof. These flow paths of FIGS. 52-56 demonstrate how the fluid may be managed through different configurations of the geometry leading from the main recirculation path (through the recirculation pipe) to the acoustic chamber. In FIG. 55 and FIG. 56, the main recirculation path to the fluid chamber have the same flow rate. One consequence of these configurations is that the separation velocities will be higher.

Figure 57:
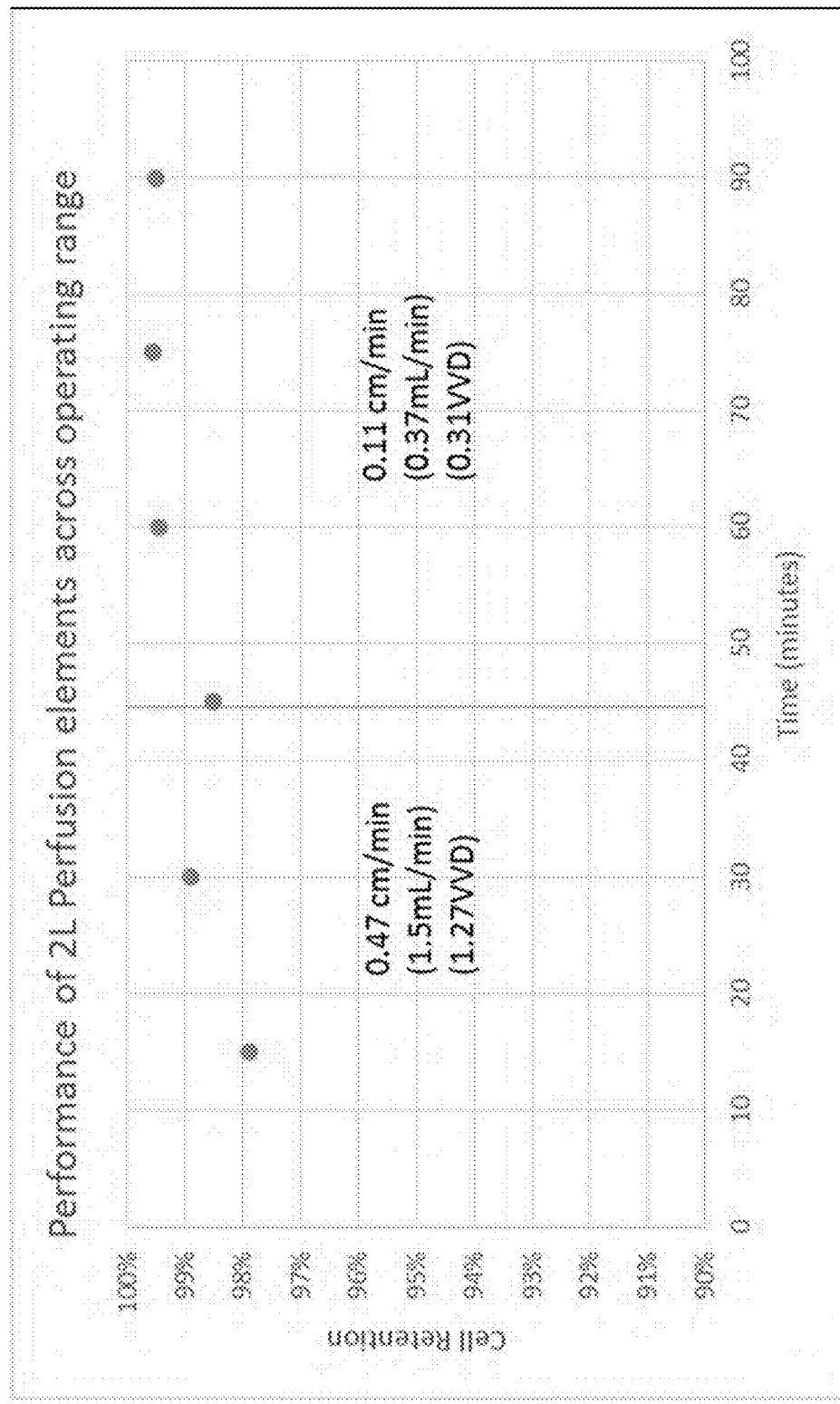
FIG. 57 is a graph of cell retention versus time for the device of FIG. 46A. The y-axis runs from 90% to 100% in intervals of 1%. The x-axis runs from 0 to 100 minutes in intervals of 10 minutes.
Figure 58:
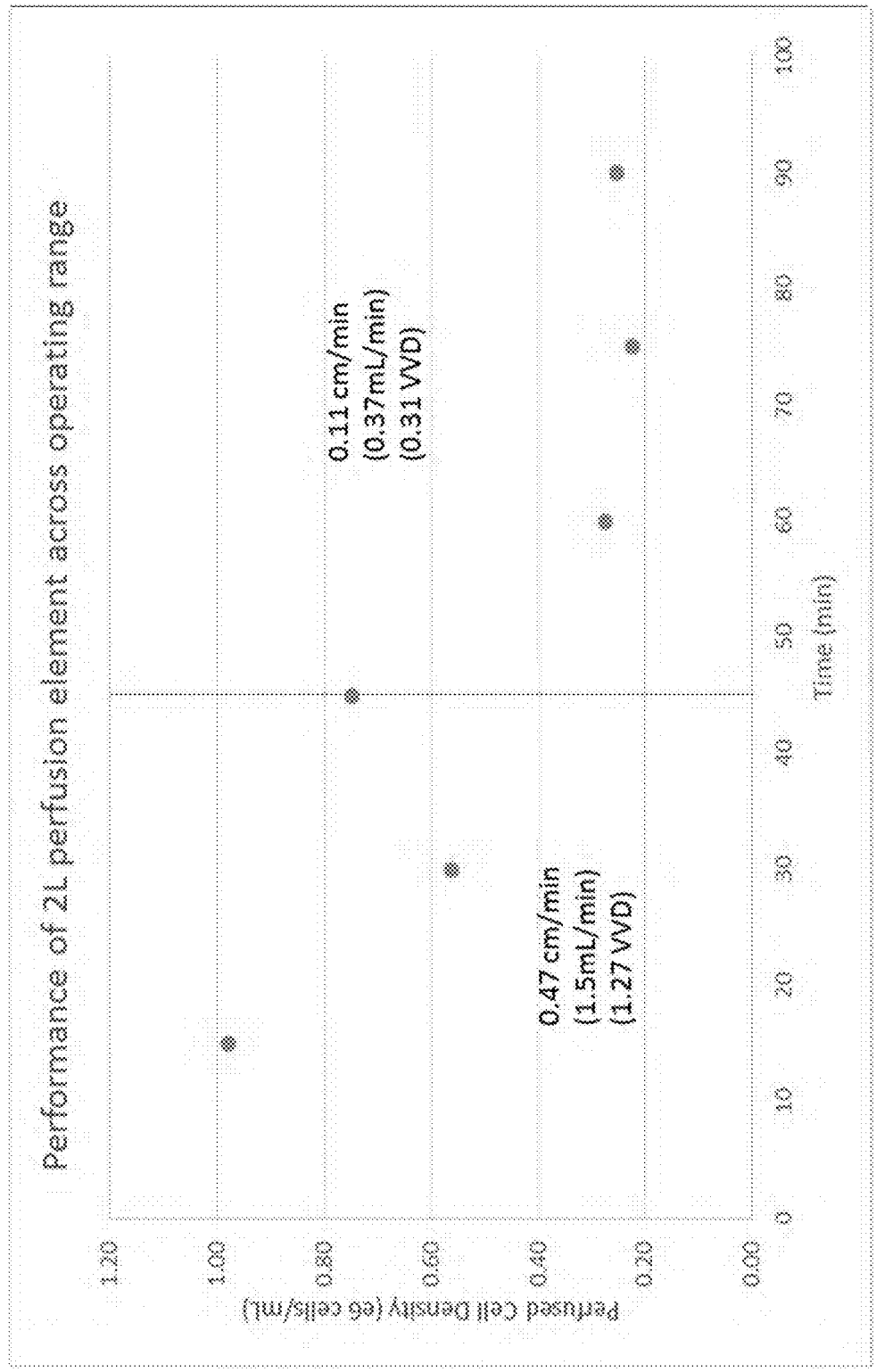
FIG. 58 is a graph of perfusate cell density (million cells/mL) versus time for the device of FIG. 46A. The y-axis runs from 0.00 to 1.20 in intervals of 0.20. The x-axis runs from 0 to 100 minutes in intervals of 10 minutes.

Next, the device with the internal structure of FIG. 46A was tested at different flowrates. FIG. 57 shows the cell retention (%) versus time. Higher values are more desirable, and most values were over 97% at flowrates ranging from 0.37 mL/min to 1.5 mL/min. FIG. 58 shows the perfusate cell density (million cells/mL) versus time. Here, lower values are more desirable (indicating successful cell separation). As expected, results were better at lower flowrates.

Figure 59:
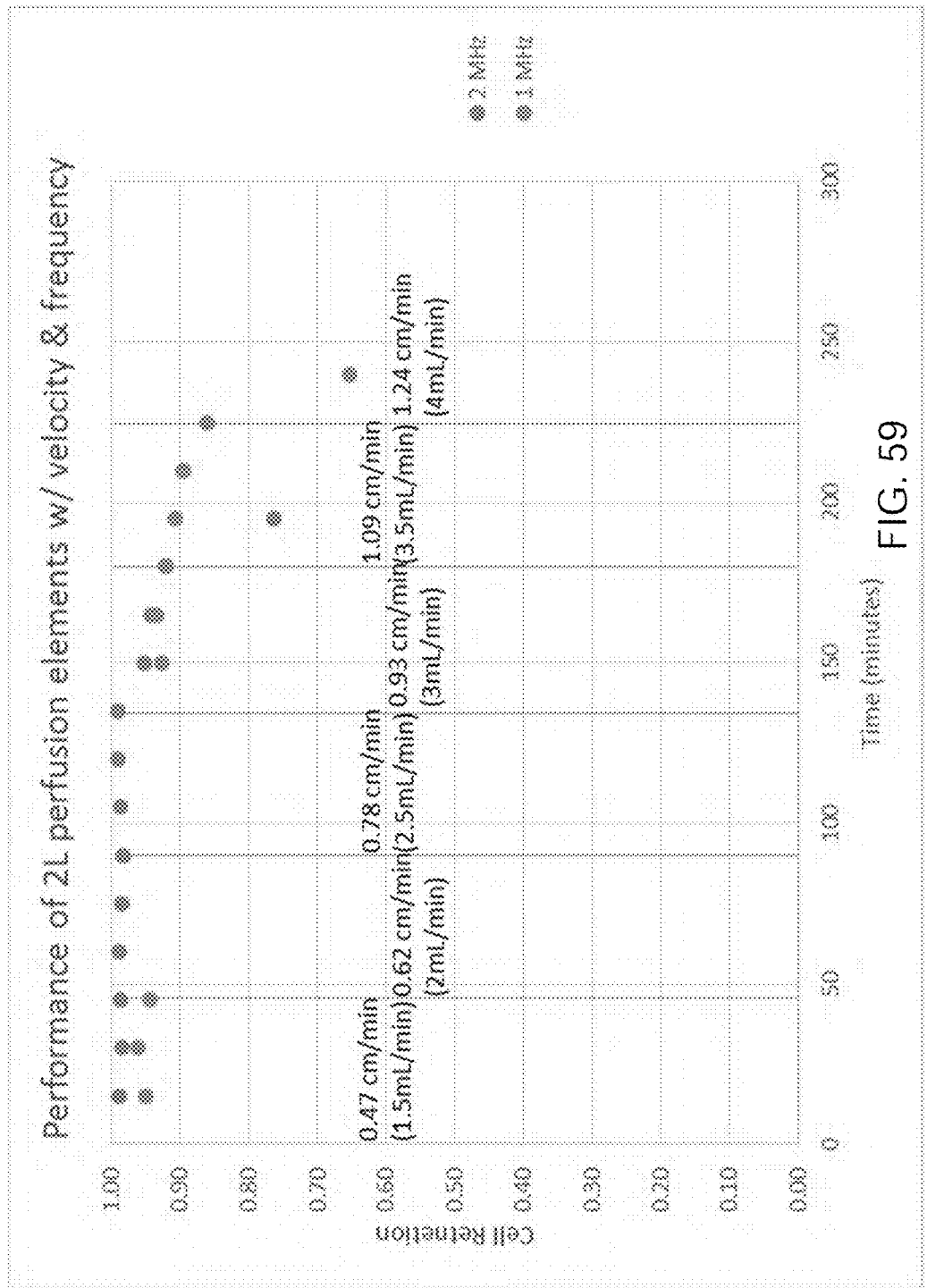
FIG. 59 is a graph of cell retention versus time for the device of FIG. 46A at two different frequencies, 1 MHz and 2 MHz. The darker circles are for 2 MHz. The y-axis runs from 0.00 to 1.00 in intervals of 0.10. The x-axis runs from 0 to 300 minutes in intervals of 50 minutes.
Figure 60:
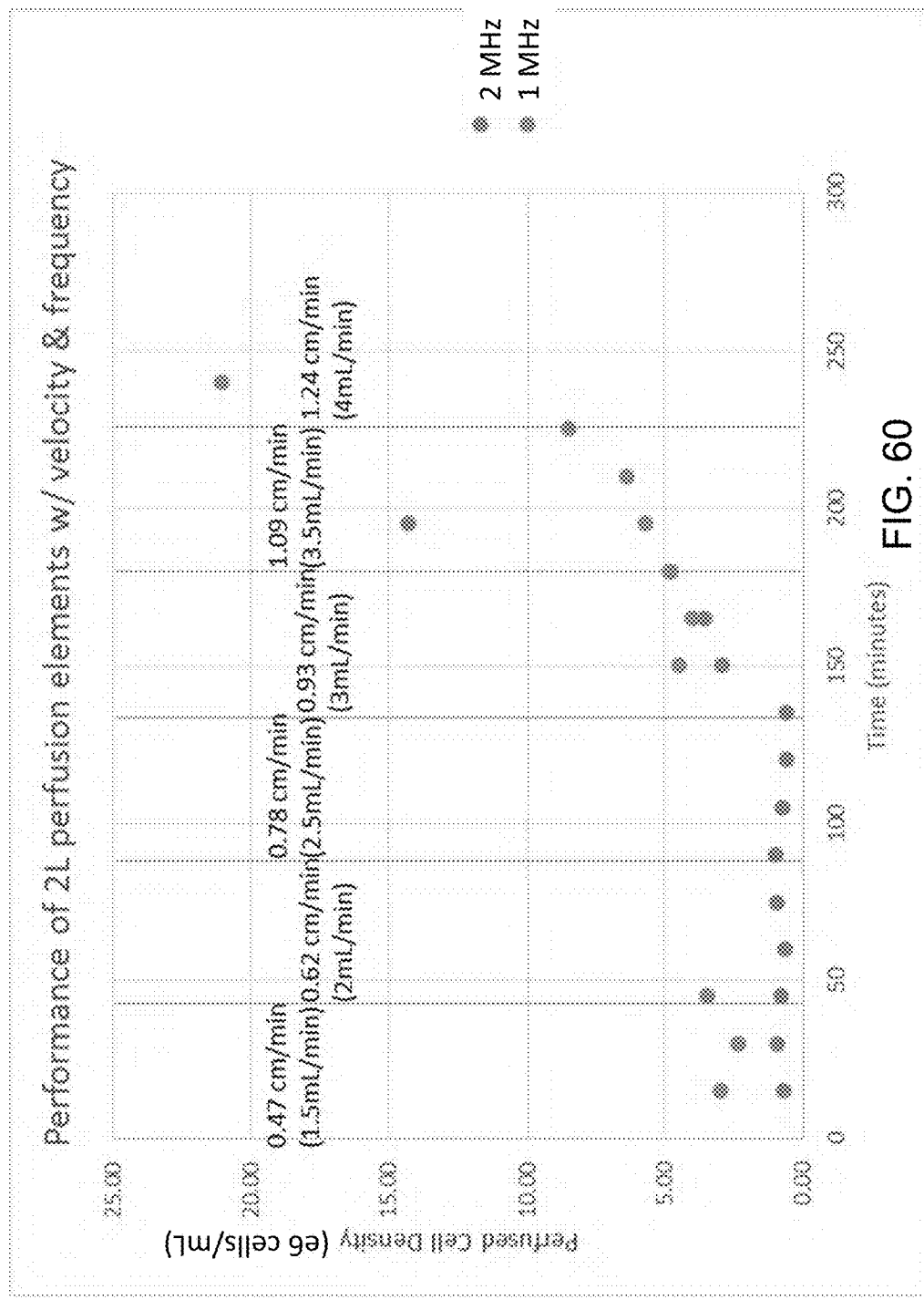
FIG. 60 is a graph of perfusate cell density (million cells/mL) versus time for the device of FIG. 46A at two different frequencies, 1 MHz and 2 MHz. The darker circles are for 2 MHz. The y-axis runs from 0.00 to 25.00 in intervals of 5.00. The x-axis runs from 0 to 300 minutes in intervals of 50 minutes.

The device was then tested using two different operating frequencies for the ultrasonic transducer, 1 MHz or 2 MHz, and at different flowrates. FIG. 59 shows the cell retention (%) versus time. Higher values are more desirable. At 2 MHz, the values were close to 100% for flow rates of 1.5 mL/min to 3 mL/min. At 1 MHz, the values stayed over 90% for flow rates of 1.5 mL/min to 3 mL/min. The frequency of 2 MHz generally performed better. FIG. 60 shows the perfusate cell density (million cells/mL) versus time. Again, results were better for 2 MHz operating frequency.

Example 7

Next, a device with an internal structure similar to FIG. 10 was used to perform acoustic separation of beads and yeast from a host fluid. The device was a 1 inch by 1 inch by 1 inch device using a 1 inch by 1 inch crystal to separate beads from a yeast mixture having a concentration of $1\times10^6$ cells/mL. The ultrasonic transducer was operated at 1 MHz with an input voltage of 60 volts, and the beads were Solohill microcarriers in the amount of 7.5 g/L. The mixture was flowed into the device at a flow rate of 75 mL/minute, while the concentrate was recovered at a rate of 5 mL/minute. FIG.

62 shows a photograph of the microcarriers being trapped in the acoustic standing wave within the device.

Example 8

Figure 64:
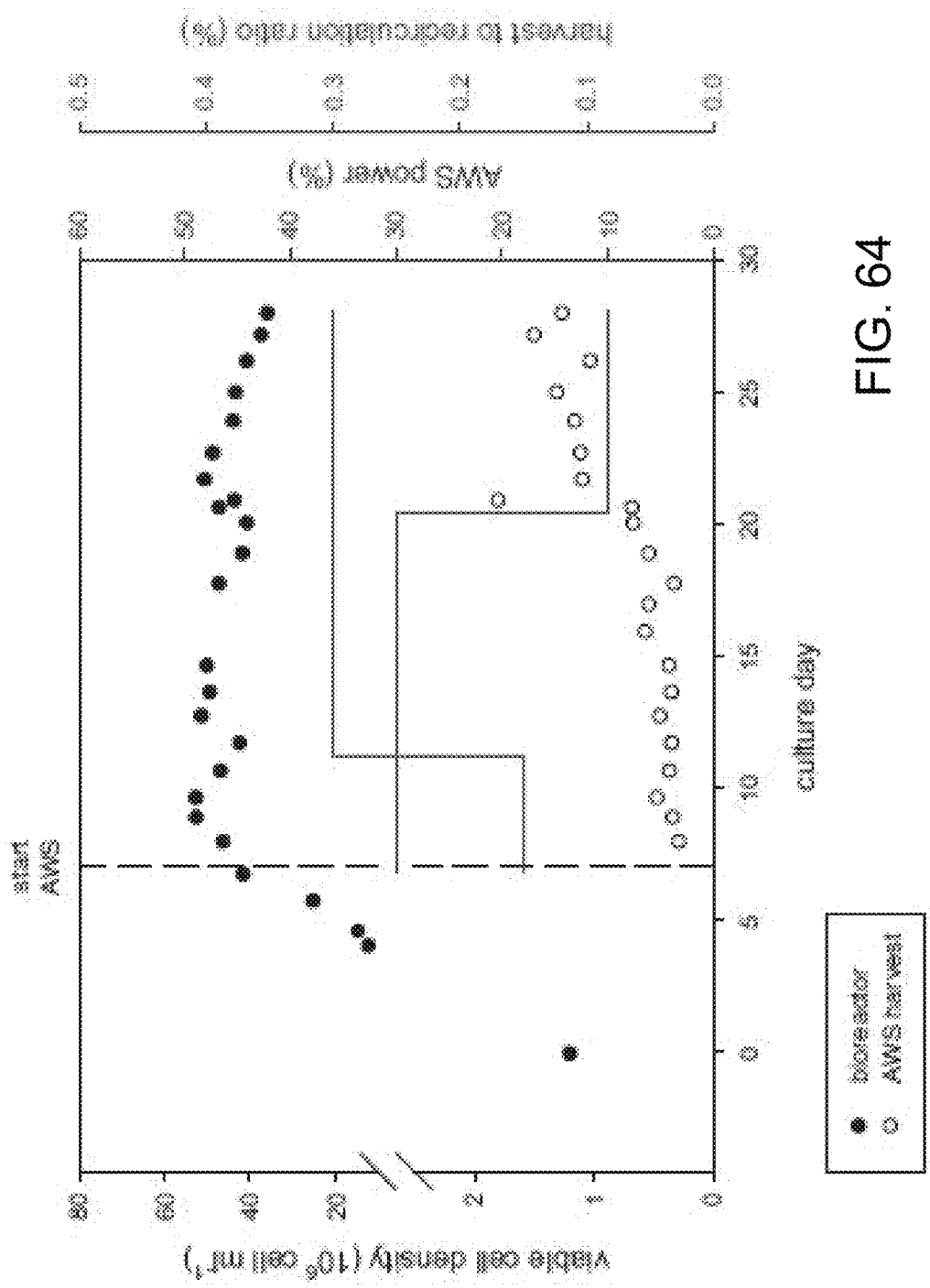
FIG. 64 is a graph of viable cell density (VCD) (10$^6$ cells/mL) over time for specified AWS power (%) and specified harvest to recirculation ratios (%). The x-axis (culture day) runs from 0 to 30 days in intervals of 5 days. The left-side y-axis (VCD) runs from 0 to 80×10$^6$ cells/mL in intervals of 1 before the break and intervals of 20 after the break, and is used for the circles. The first right-side y-axis (AWS power) runs from 0 to 60 in intervals of 10, and applies to the line that starts at about 30% and ends at about 10%. The second right-side y-axis (harvest to recirculation ratio) runs from 0.0 to 0.5 in intervals of 0.1, and applies to the line that starts at about 0.15% and ends at 0.3%. A vertical dashed line shows that AWS began on day 7. The darker line extending from the vertical dash line corresponds to the AWS power, and the lighter line extending from the vertical dashed line corresponds to the harvest to recirculation ratio. The white dots represent the AWS harvest, and the black dots represent the bioreactor.

Next, a device with an internal structure similar to FIG. 7 was used to examine AWS cell separation efficiency. FIG. 64 shows the viable cell density (left-side y-axis), AWS power (right-side y-axis), and harvest to recirculation ratio (right-side y-axis) over a period of about 28 days. The dark dots represent the bioreactor, while the light dots represent the AWS harvest. The system was operated with AWS beginning on day 7 through the end of the study. From day 7 to day 20, the system was operated at 30% AWS power, before being switched to 10% AWS power from day 20 to the end of the study. The harvest to recirculation ratio was about 15% from day 7 (start of AWS) to day 11, about 30% from day 11 to the end of the study.

Figure 65:
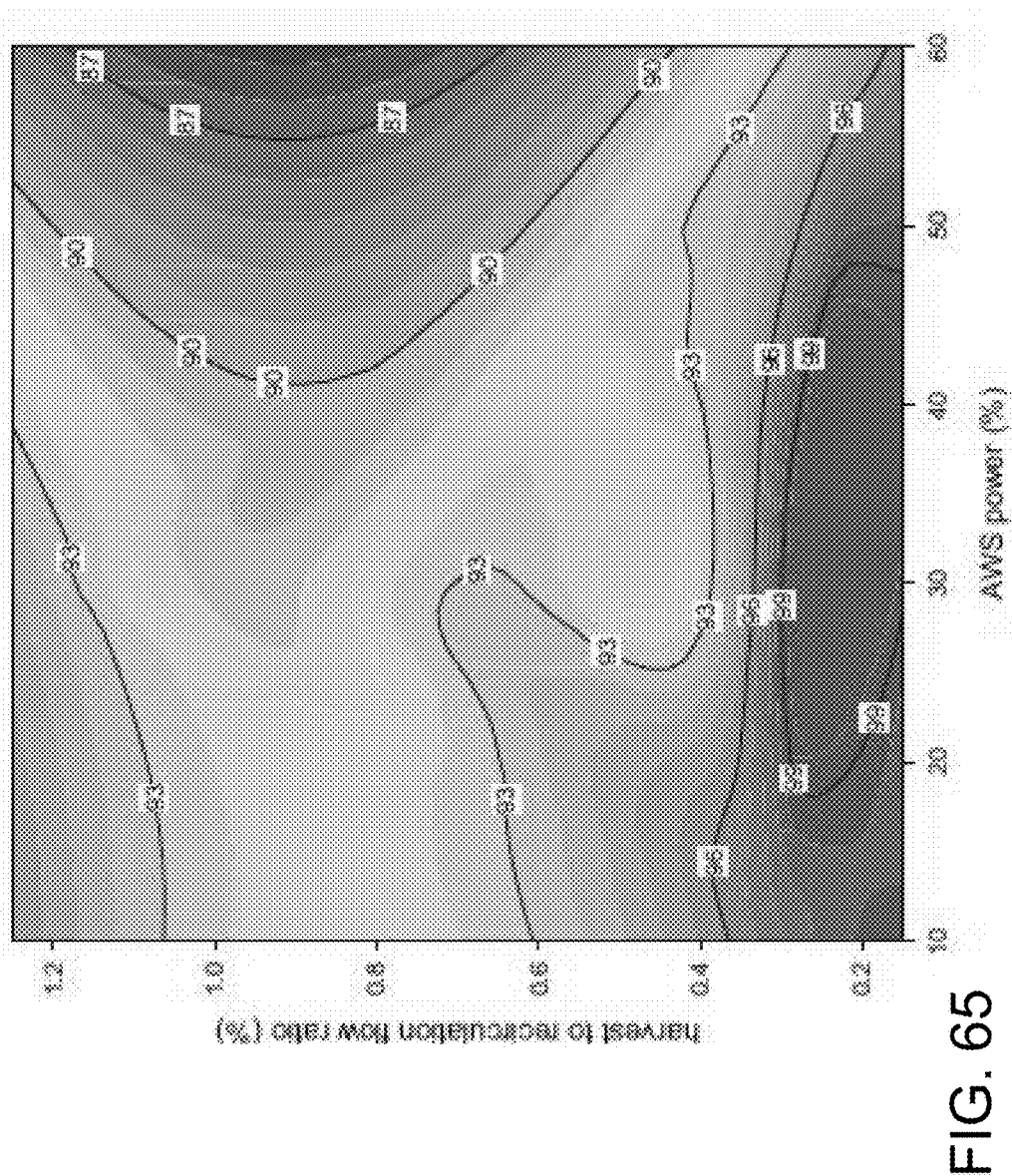
FIG. 65 is a space characterization of the harvest to recirculation flow ratio (%) versus the AWS power (%). The y-axis (harvest to recirculation flow ratio) runs from 0.2 to 1.2 in intervals of 0.2. The x-axis (AWS power) runs from 10 to 60 in intervals of 10.
Figure 66A:
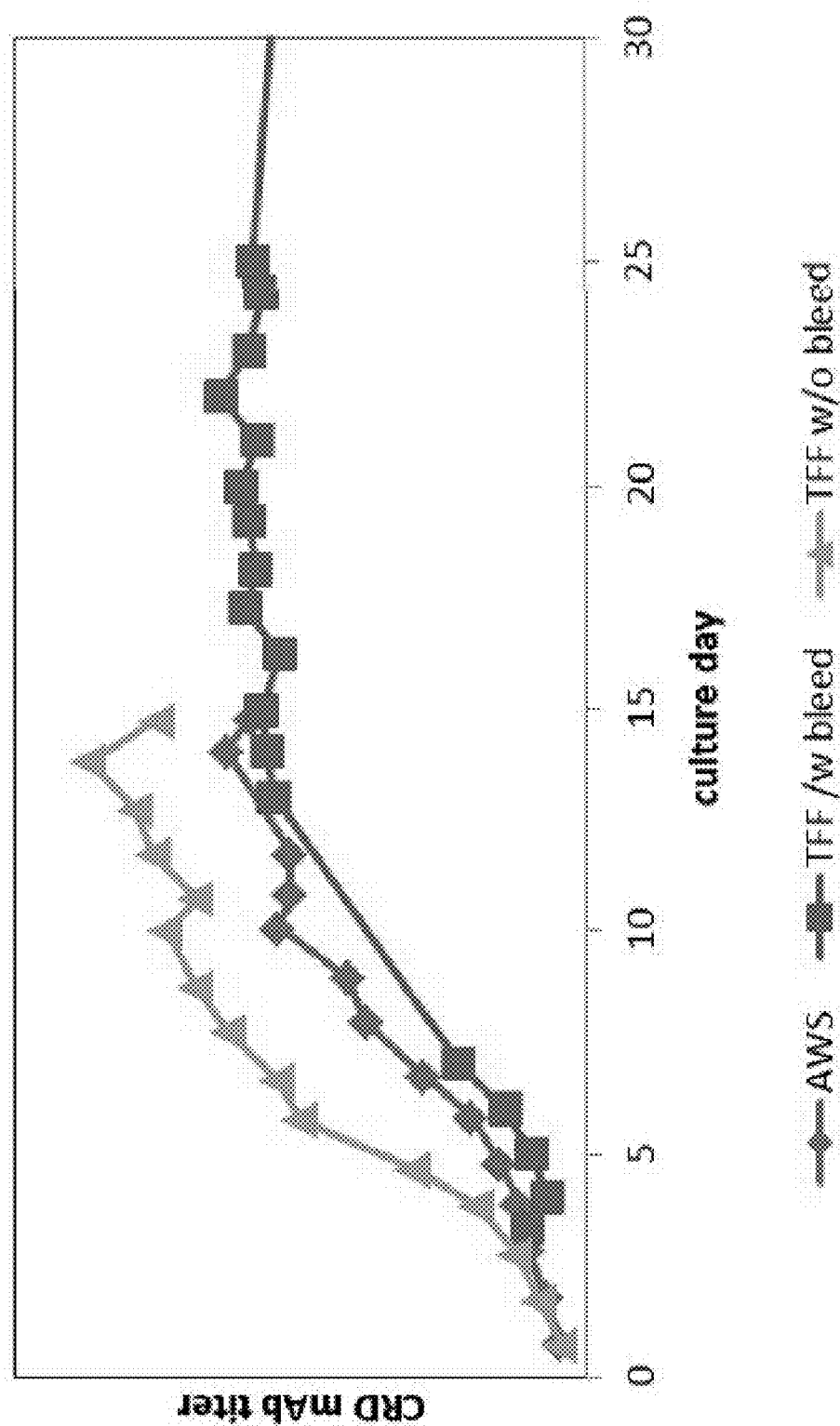
FIGS. 66A-66C are graphs of AWS versus TFF mAb titer and product transmission. In all three graphs, AWS is diamonds, TFF with bleed is squares, and TFF without bleed is triangles.
Figure 66B:
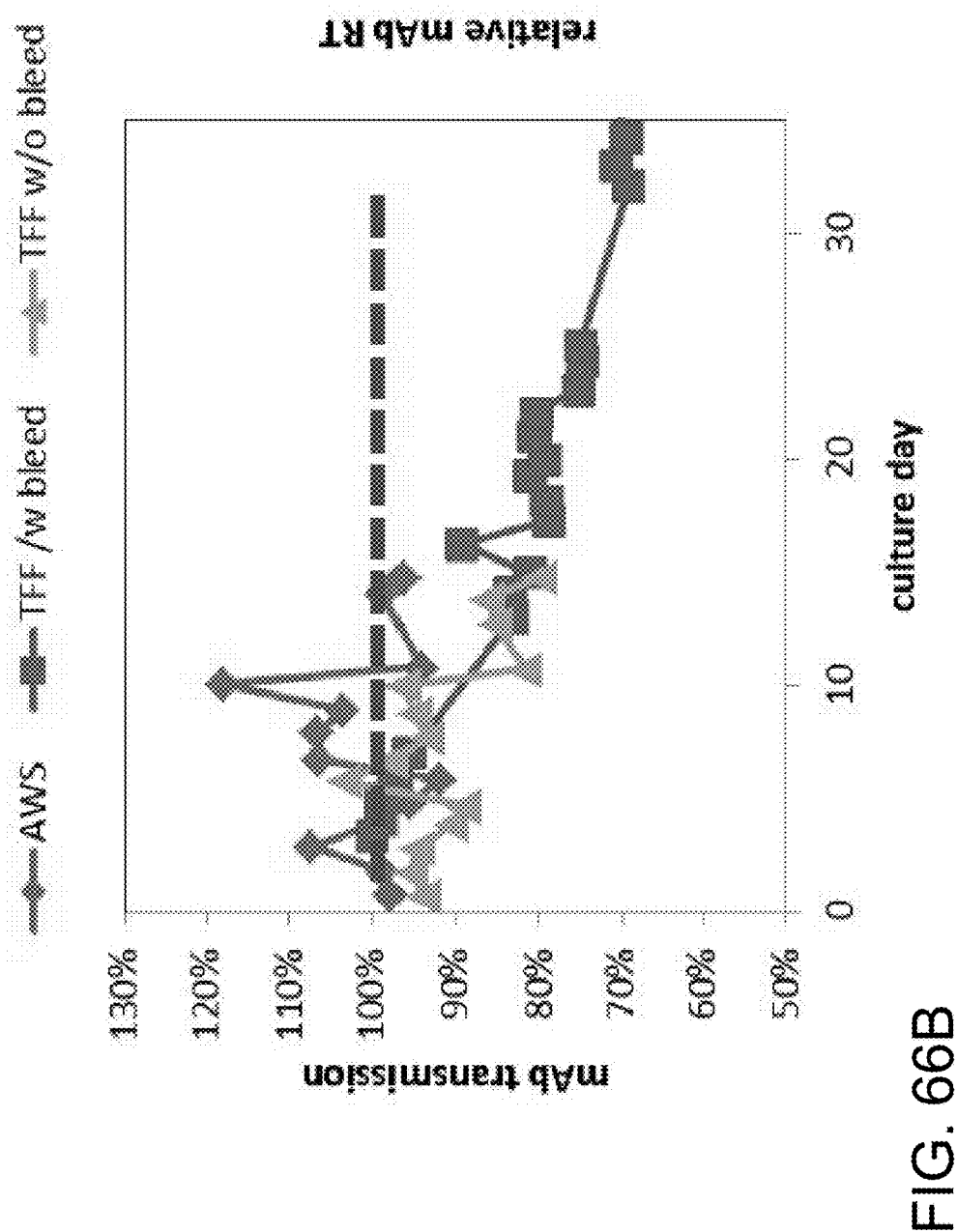
Figure 66C:
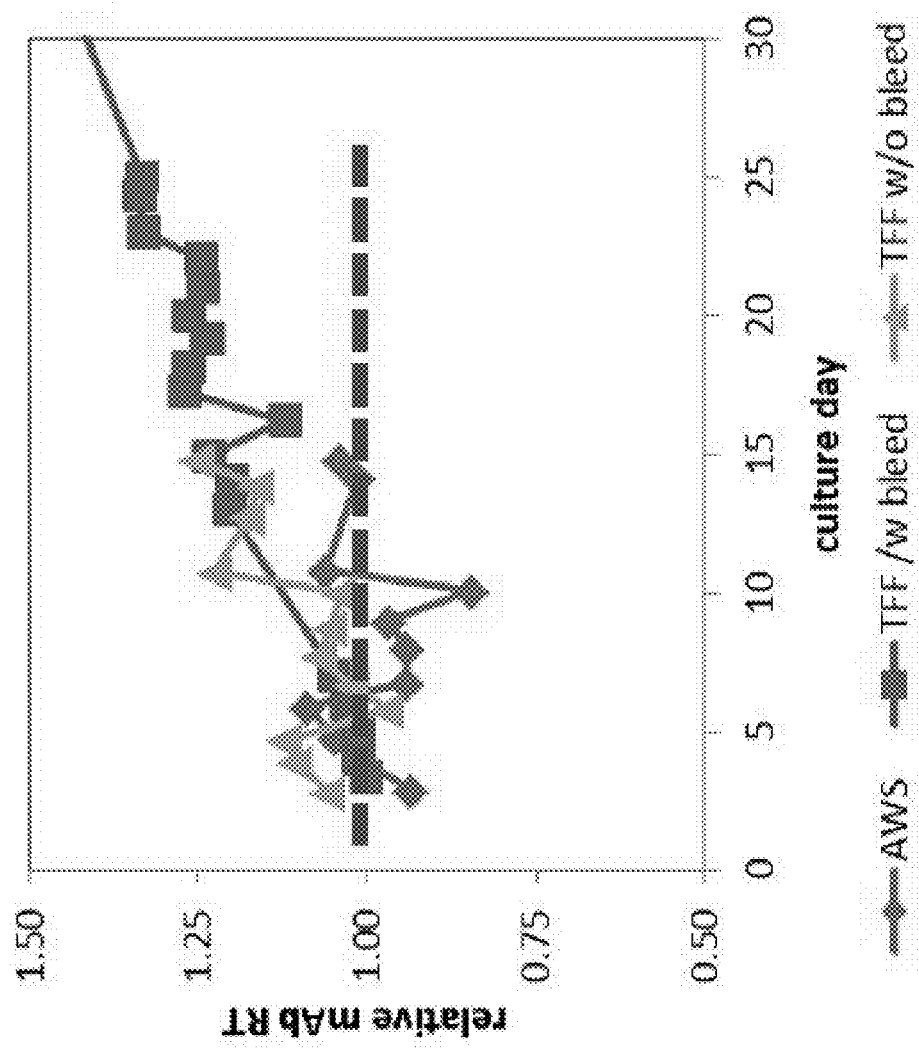
Figure 67:
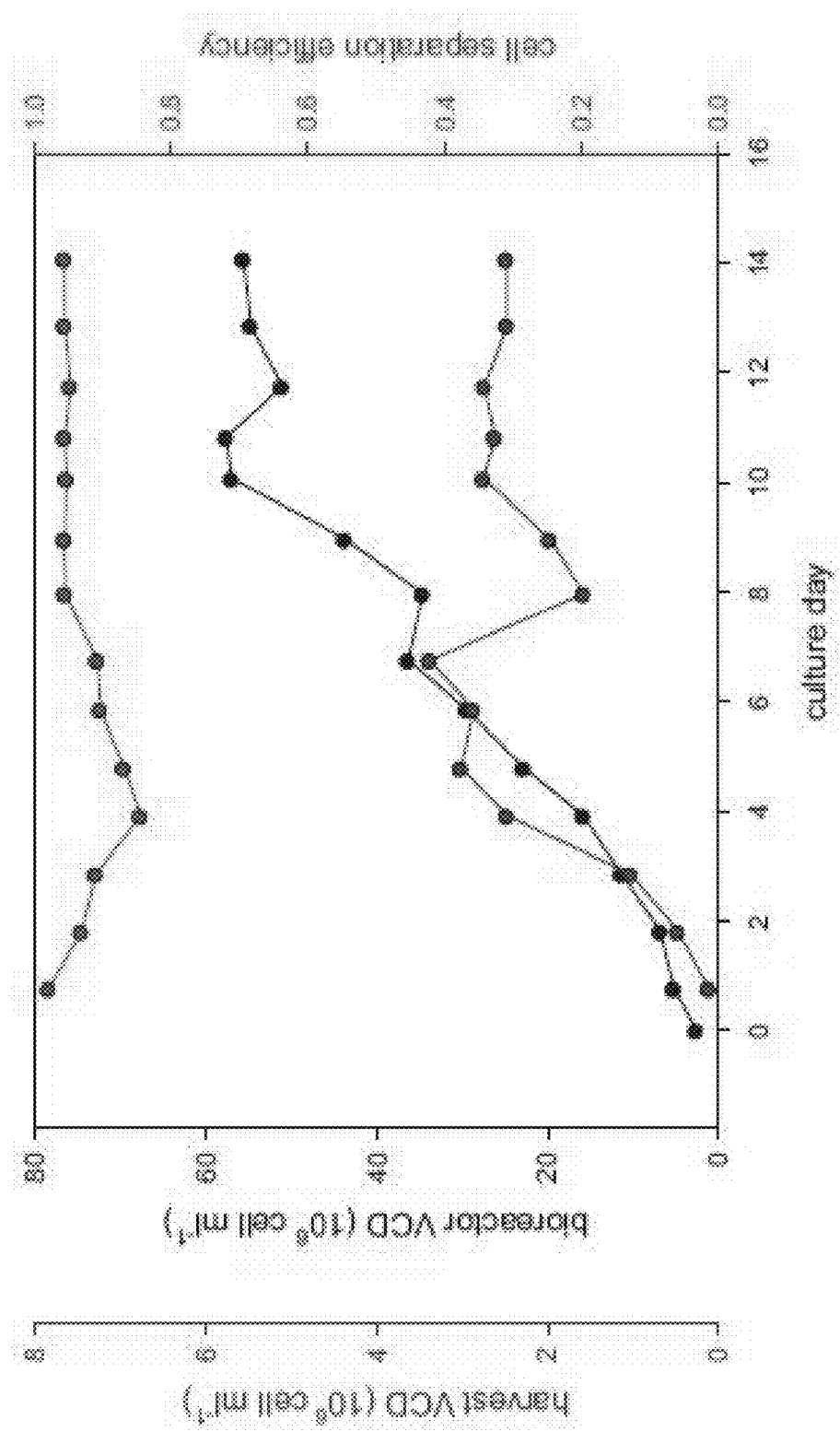
FIG. 67 is a graph of cell separation efficiency over time for AWS cell separation at a 10 L scale. The x-axis (culture day) runs from 0 to 16 days in intervals of 2 days, and is used for the middle line that starts at x=0 days. The first left-side y-axis (harvest VCD) runs from 0 to $8 \times 10^6$ cells/mL in intervals of 2, and is used for the bottom line that starts at roughly x=1 day. The second left-side y-axis (bioreactor VCD) runs from 0 to $80 \times 10^6$ cells/mL in intervals of 20. The right-side y-axis (cell separation efficiency) runs from 0.0 to 1.0 in intervals of 0.2, and is used for the top line. The cell separation efficiency is a percentage (i.e., 0.2 corresponds to 20% efficiency, 0.6 corresponds to 60% efficiency, 1.0 corresponds to 100% efficiency, etc.)

The cell separation efficiency was dominated by the harvest to recirculation flow ratio, as shown in FIG. 65 which compares the AWS power (x-axis) to the harvest to recirculation flow ratio (y-axis). The device was then paired with a 10 L bioreactor, and the AWS cell separation efficiency was again examined. FIGS. 66A-66C show similar volumetric productivity, improved product transmission, and improved product residence time for AWS versus TFF. FIG. 67 shows the cell separation efficiency (right-side y-axis), the harvest VCD (left-side y-axis), and bioreactor VCD (left-side y-axis) over a period of about 14 days. The system had a greater than 90% cell separation at 30% AWS power and a 1.25% harvest to recirculation ratio.

Overall, AWS separation was shown to not affect the quality between the bioreactor and the harvest, as shown in FIGS. 68A-68C. FIG. 68A graphically shows the relative abundance after size exclusion chromatography (SEC) of high molecular weight (HMW) species, monomer species, and low molecular weight (LMW) species of a monoclonal antibody (mAb). The darker bars represent the bioreactor, and the lighter bars represent the harvest. FIG. 68B graphically shows the relative abundance after ion exchange chromatography (IEX) of acidic, main peak, and basic species of a mAb. The darker bars represent the bioreactor, and the lighter bars represent the harvest. FIG. 68C shows glycosylation of the protein. The effects are the same for the protein that is from the bioreactor and for the protein that has passed through the acoustic separation device. These results show that acoustics do not affect the protein.

Figure 69A:
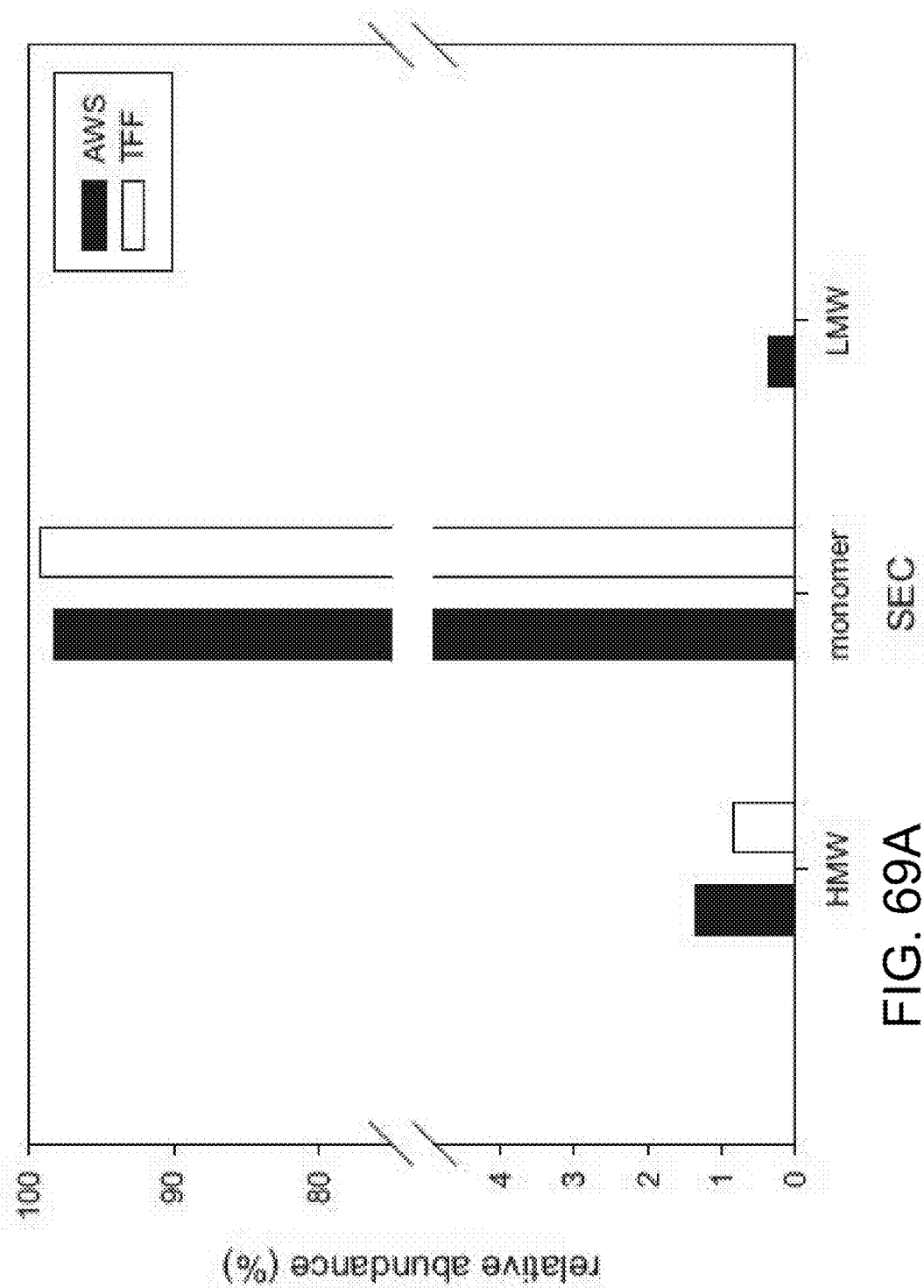
FIGS. 69A-69B are graphs comparing the AWS process to a tangential flow filtration (TFF) perfusion process using a 0.22 micron membrane. The darker bars represent AWS and the lighter bars represent TFF.
Figure 69B:
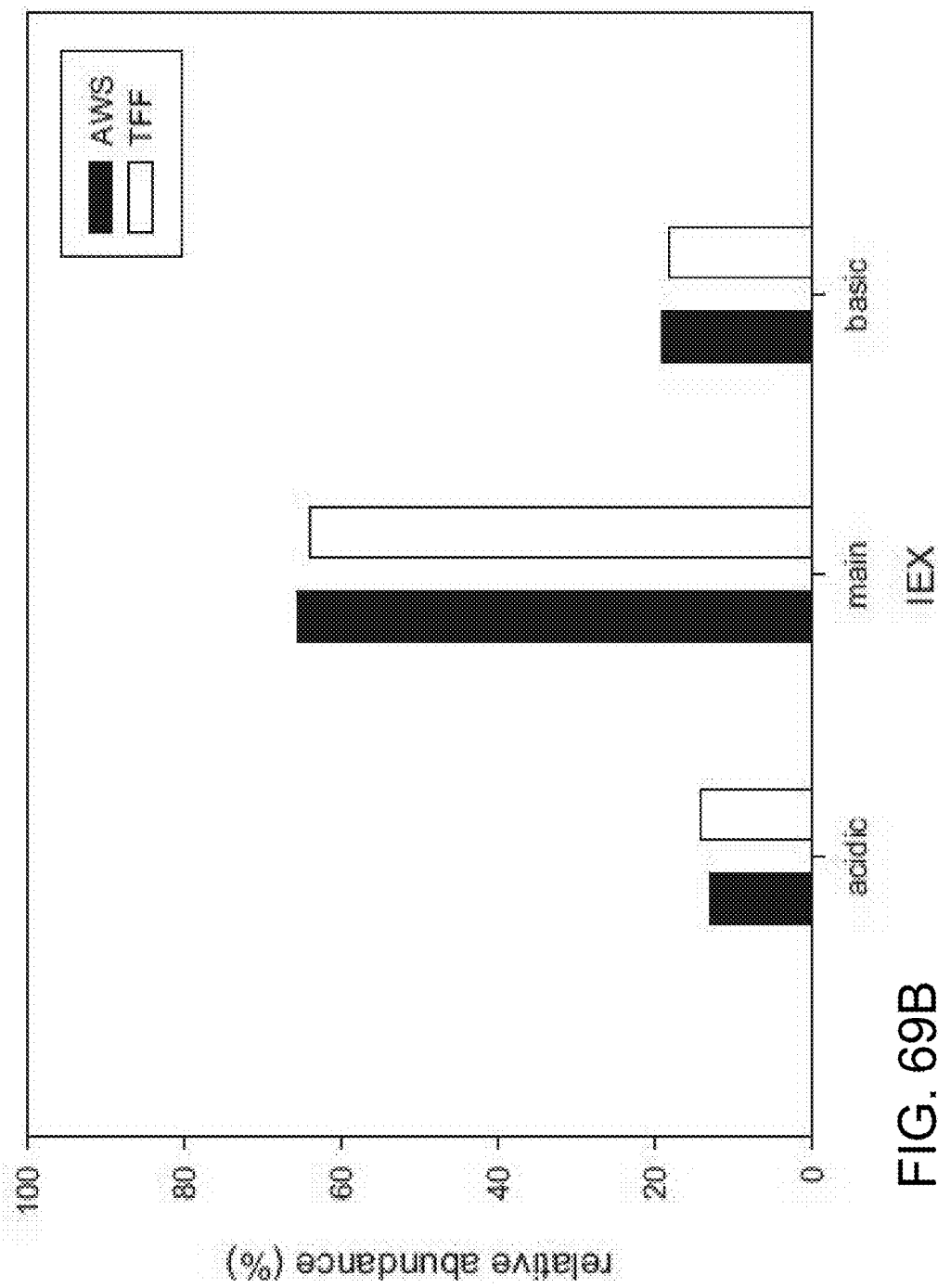

Finally, AWS separation was shown to have comparable quality to a TFF perfusion process using a 0.22 micron membrane, as shown in FIG. 69A and FIG. 69B. FIG. 69A graphically shows the relative abundance after size exclusion chromatography (SEC) of HMW species, monomer species, and LMW species of a monoclonal antibody (mAb). The darker bars represent AWS, and the lighter bars tangential flow filtration (TFF). FIG. 69B graphically shows the relative abundance after ion exchange chromatography (IEX) of acidic, main peak, and basic species of a mAb. The darker bars represent AWS, and the lighter bars represent TFF. As can be seen in FIG. 69A and FIG. 69B, there was a negligibly higher HWM species in AWS and similar charge variance profile between AWS and TFF.

Example 9

Figure 70:
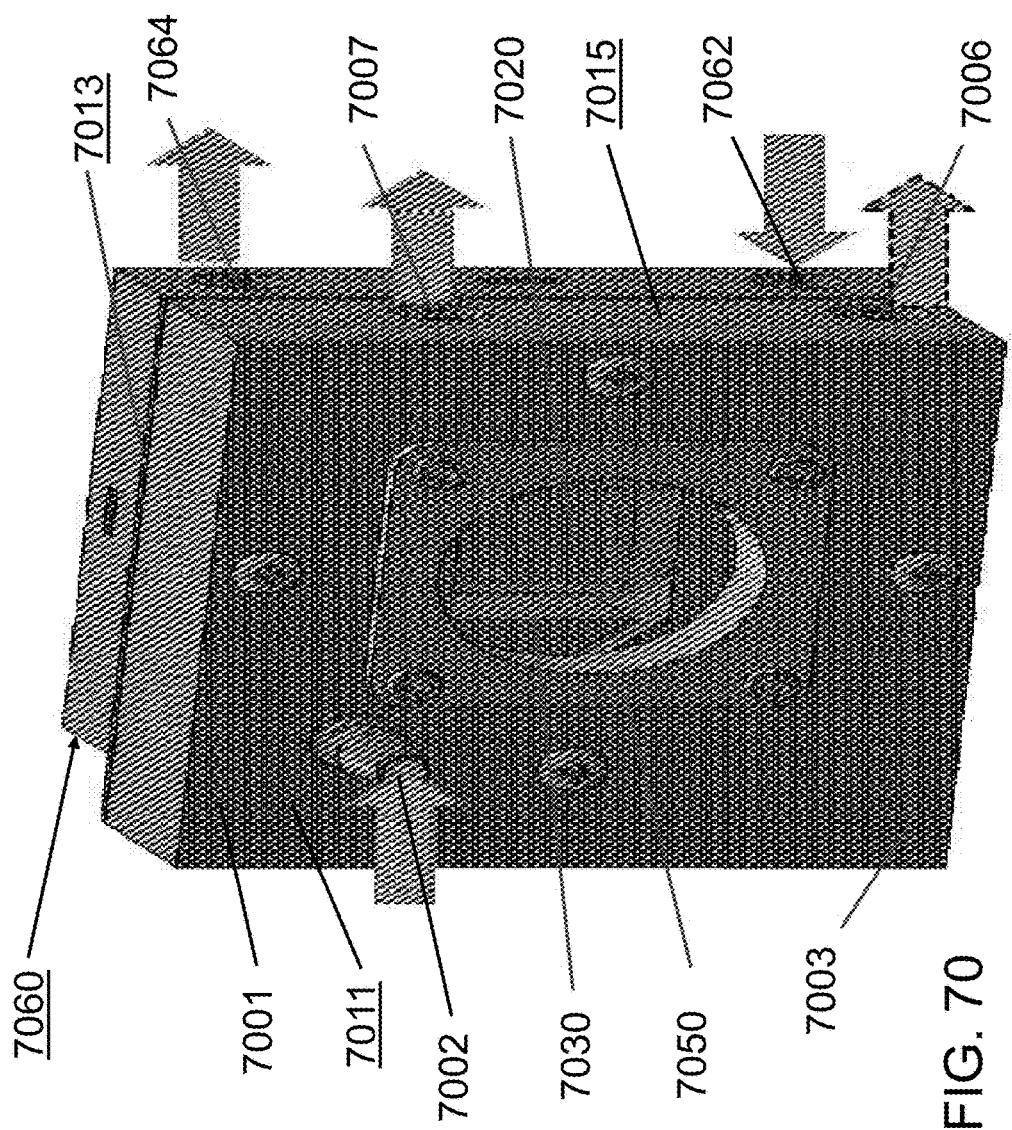
FIG. 70 is a perspective view of an eighth exemplary embodiment of an acoustic perfusion device of the present disclosure.

FIG. 70 depicts another device 7000 that can be used for acoustophoresis. Device 7000 includes a first inlet port 7002 along a front wall 7011 of the device near the top end 7001 of the device. A second inlet port (not shown) can be located along a rear wall 7013 of the device opposite the front wall 7011 thereof. A viewing window 7050 made of a transparent material is also present in the front wall 7011. Through the viewing window 7050, it can be seen that an ultrasonic transducer 7020 is also coupled to the rear wall 7013. In this embodiment, the viewing window 7050 acts as a reflector to generate the multi-dimensional acoustic standing wave(s). Both the reflector and the ultrasonic transducer are generally located below the inlet(s), such that the acoustic chamber is positioned below the inlet(s). In particular embodiments, the first and second inlets are located directly opposite one another in the device. A drain outlet 7006 is located near a bottom end 7003 of the device above the acoustic chamber, and here is located along a first sidewall 7015 of the device. The drain outlet generally serves as the outlet through which the concentrate fluid (retained material prevented from passing through the standing wave) is recovered from the device. A permeate outlet 7007, which generally serves as the outlet through which the permeate (material that passes through the standing wave) is recovered from the device, is located above the acoustic chamber, and as illustrated here is also located along the first sidewall 7015 of the device above the drain outlet 7006.

The device 7000 includes a cooling unit 7060 coupled to the rear wall 7013. The cooling unit 7060 includes an independent flow path that is separate from the flow path through the device containing the fluid that is to be exposed to the multi-dimensional acoustic standing wave. A coolant inlet 7062 is adapted to permit the ingress of a cooling fluid into the cooling unit. A coolant outlet 7064 serves as the outlet through which the coolant and waste heat exit the cooling unit. Here, the coolant inlet is located below the coolant outlet, though this path can be varied as desired. The coolant that flows through the cooling unit can be any appropriate fluid. For example, the coolant can be water, air, alcohol, ethanol, ammonia, or some combination thereof. The coolant can, in certain embodiments, be a liquid, gas, or gel. The coolant can be an electrically non-conductive fluid to prevent electric short-circuits. The cooling unit can be used to cool the ultrasonic transducer, which can be particularly advantageously when the device is to be run continuously with repeated processing and recirculation for an extended period of time (e.g., perfusion). The cooling unit can also be used to cool the host fluid running through the device 7000, if desired.

The performance of the device 7000 of FIG. 70 was tested using Jurkat T cells and compared to a device having a structure similar to device 900 of FIG. 9. The performance of each device is summarized in the table below.

| Device | Feed ($10^6$ cells/mL) | Trapped (%) | Collected (%) | Volume Reduction | Cell Concentrating |
|---|---|---|---|---|---|
| FIG. 9 | 0.90 | 65 | 49 | 5.7 | 2.8 |
| FIG. 9 | 0.76 | 84 | 74 | 2.6 | 1.9 |
| FIG. 70 | 0.77 | 86 | 71 | 11.9 | 8.4 |
| FIG. 70 | 0.70 | 75 | 72 | 11.3 | 8.2 |
| FIG. 70 | 0.77 | 87 | 77 | 11.4 | 8.9 |

The performance of the device was then tested using CHO cells and again compared to a device having a structure similar to device 900 of FIG. 9. The performance of each device is summarized in the table below.

| Device | Feed (10⁶ cells/mL) | Trapped (%) | Collected (%) | Volume Reduction | Cell Concentrating |
|---|---|---|---|---|---|
| FIG. 70 | 1.11 | 91 | 72 | 12.8 | 9.2 |
| FIG. 70 | 1.07 | 90 | 70 | 12.5 | 8.8 |
| FIG. 70 | 0.99 | 92 | 67 | 13.0 | 8.7 |

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method for separating a desired target material from a host fluid, the method comprising:
   flowing a mixture containing the host fluid, beads, and the target material through an acoustophoretic device, the acoustophoretic device comprising:
      a flow chamber including at least one inlet and at least one outlet;
      at least one ultrasonic transducer coupled to the flow chamber, the at least one ultrasonic transducer including a piezoelectric material configured to be driven to create a multi-dimensional acoustic standing wave in the flow chamber; and
      a reflector located opposite from the at least one ultrasonic transducer; and
   driving the at least one ultrasonic transducer to create the multi-dimensional acoustic standing wave, wherein a recirculating fluid stream that includes a tangential flow path is located substantially tangential to the multi-dimensional acoustic standing wave and separated therefrom by an interface region;
   wherein the beads attach to the target material and are held back from the multi-dimensional acoustic standing wave in the recirculating fluid stream at the interface region; and wherein the host fluid passes through the multi-dimensional acoustic standing wave.

2. The method of claim 1, wherein the at least one outlet includes (i) a permeate outlet through which the host fluid exits the flow chamber; and (ii) a concentrate outlet through which the target material exits the flow chamber.

3. The method of claim 1, wherein the beads are not functionalized.

4. The method of claim 1, wherein the beads are functionalized.

5. The method of claim 1, wherein the beads have a positive contrast factor.

6. The method of claim 5, wherein the beads are selected from the group consisting of polystyrene beads and glass beads.

7. The method of claim 1, wherein the beads have a negative contrast factor.

8. The method of claim 7, wherein the beads are selected from the group consisting of microbubbles and micro-glass spheres.

9. The method of claim 1, wherein the beads are polymeric.

10. The method of claim 1, wherein the beads are glass, hollow, or gas-filled.

11. The method of claim 1, wherein the beads are spherical, toroidal, cylindrical, or conical.

12. The method of claim 1, wherein the desired target material is microvesicles, viruses, proteins, recombinant proteins, or monoclonal antibodies.

13. The method of claim 12, wherein the microvesicles are exosomes or oncosomes.

14. The method of claim 1, wherein a pressure rise and an acoustic radiation force on cells are generated at the interface region to clarify the host fluid as the mixture passes through the multi-dimensional acoustic standing wave.

15. The method of claim 1, wherein the acoustophoretic device includes a cooling unit for cooling the at least one ultrasonic transducer.

16. The method of claim 1, wherein at least 95% of the cells pass through the multi-dimensional acoustic standing wave.

17. An acoustophoretic device, comprising:
   a flow chamber including at least one inlet port and at least one outlet;
   at least one ultrasonic transducer coupled to the flow chamber and at least one reflector opposite the at least one ultrasonic transducer, wherein the at least one ultrasonic transducer includes a piezoelectric material that is configured to be driven to create a multi-dimensional acoustic standing wave in the device; and
   a cooling unit for cooling the at least one ultrasonic transducer.

18. An acoustophoretic device, comprising:
   a flow chamber including at least one inlet and at least one outlet;
   at least one ultrasonic transducer coupled to the flow chamber, the at least one ultrasonic transducer including a piezoelectric material configured to be driven to create a multi-dimensional acoustic standing wave in the flow chamber;
   the flow chamber being configured to house a recirculating fluid stream that includes a tangential flow path located substantially tangential to the multi-dimensional acoustic standing wave and separated therefrom by an interface region; and
   the multi-dimensional acoustic standing wave and the recirculating fluid stream at the interface region being configured to prevent or permit passage of particles of a certain size.

19. The acoustophoretic device of claim 18, further comprising a controller configured to influence one or more of the fluid stream or the multi-dimensional acoustic standing wave to control the size of particles that are prevented or permitted passage through the multi-dimensional acoustic standing wave.

20. The acoustophoretic device of claim 19, wherein the controller is configured to control one or move of fluid flow rate, frequency of the at least one ultrasonic transducer or power applied to the at least one ultrasonic transducer.

21. A method for separating a desired target material from a host fluid from a perfusion bioreactor, the method comprising:
   flowing a mixture containing the host fluid and the target material through an acoustophoretic device, the acoustophoretic device comprising:
      a flow chamber including at least one inlet and at least one outlet;
      at least one ultrasonic transducer coupled to the flow chamber, the at least one ultrasonic transducer including a piezoelectric material configured to be driven to create a multi-dimensional acoustic standing wave in the flow chamber; and driving the at least one ultrasonic transducer to create the multi-dimensional acoustic standing wave, wherein a recirculating fluid stream that includes a tangential flow path is located substantially tangential to the multi-dimensional acoustic standing wave and separated therefrom by an interface region;

wherein the percentage of target material transmitted through the multi-dimensional acoustic standing wave is consistent over a plurality of culture days.

22. The method of claim 21, wherein the percentage of target material transmitted is at or near the target material content of the perfusion bioreactor.

23. The method claim 21, wherein the target material is one or more of monoclonal antibodies or recombinant proteins.

* * * * *

UNITED STATES PATENT AND TRADEMARK OFFICE
CERTIFICATE OF CORRECTION

PATENT NO. : 9,745,548 B2
APPLICATION NO. : 15/420073
DATED : August 29, 2017
INVENTOR(S) : Bart Lipkens et al.

Page 1 of 1

It is certified that error appears in the above-identified patent and that said Letters Patent is hereby corrected as shown below:

On the Title Page

On page 2, item (60), in Column 1, Line 26, delete "61/611,440" and insert -- 61/611,240 --.

Signed and Sealed this
Eleventh Day of August, 2020

Andrei Iancu
*Director of the United States Patent and Trademark Office*